(12) United States Patent
Blomenrohr et al.

(10) Patent No.: US 9,127,038 B2
(45) Date of Patent: Sep. 8, 2015

(54) KISSPEPTIDE-PENTASACCHARIDE CONJUGATES

(75) Inventors: Marion Blomenrohr, Oss (NL); Martin De Kort, Oss (NL); Miranda Maria Cornelia Van Der Lee, Oss (NL); Jeffry Abraham Jacobus Wisse, Oss (NL)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 14/236,694

(22) PCT Filed: Aug. 1, 2012

(86) PCT No.: PCT/EP2012/065061
§ 371 (c)(1),
(2), (4) Date: Mar. 21, 2014

(87) PCT Pub. No.: WO2013/017631
PCT Pub. Date: Feb. 7, 2013

(65) Prior Publication Data
US 2014/0206627 A1    Jul. 24, 2014

(30) Foreign Application Priority Data

Aug. 4, 2011    (EP) .................................... 11176518

(51) Int. Cl.
*C07K 9/00*    (2006.01)
*A61K 47/48*    (2006.01)

(52) U.S. Cl.
CPC ........... *C07K 9/001* (2013.01); *A61K 47/48092* (2013.01)

(58) Field of Classification Search
None
See application file for complete search history.

(56) References Cited

U.S. PATENT DOCUMENTS

| 7,625,869 | B2 | 12/2009 | Kitada et al. |
| 7,786,083 | B2 | 8/2010 | Asami et al. |
| 2008/0139459 | A1* | 6/2008 | Bos et al. ......................... 514/8 |

FOREIGN PATENT DOCUMENTS

| EP | 1886696 | A1 | 2/2008 |
| EP | 2314609 | A1 | 4/2011 |
| WO | 2005/117939 | A2 | 12/2005 |
| WO | 2006001499 | A2 | 1/2006 |
| WO | 2006082184 | A2 | 8/2006 |
| WO | 2008029278 | A2 | 3/2008 |
| WO | 2010013762 | A1 | 2/2010 |

(Continued)

OTHER PUBLICATIONS

Niida et al, "Design and synthesis of downsized metastin (45-54) analogs with maintenance of high GPR54 agonistic activity," Bioorganic & Medicinal Chemistry Letters 16 (2006) 134-137.*
R. C. Buijsman, et al., "Synthesis of a Pentasaccharide—Oligonucleotide Conjugate: A Novel Antithrombotic Agent", Chemistry—A European Journal, vol. 2, No. 12, pp. 1572-1577 (1996).
R. C. Buijsman, et al., "Design and Synthesis of a Novel Synthetic Napap-Pentasaccharide Conjugate Displaying a Dual Antithrombotic Action", Bioorganic & Medicinal Chemistry, vol. 9, pp. 2013-2018 (1999).

(Continued)

*Primary Examiner* — Thomas S Heard
(74) *Attorney, Agent, or Firm* — Anna L. Cocuzzo; Catherine D. Fitch

(57) ABSTRACT

The invention relates to kisspeptide-pentasaccharide conjugates having the general formula (I) wherein $Z_1$ is Tyr or D-Tyr; $Z_3$ is Trp, Hyp, Phe or Lys($R_2$); $Z_5$ is Thr, Aib or Ala; $Z_7$ is Gly or azaGly; $Z_8$ is Leu; or $Z_7$ and $Z_8$ together represent; $Z_{10}$ is Phe or Trp; n is 0 or 1; or $R_2$, when present, represents a pentasaccharide derivative having the formula (II) wherein R is methyl or $SO_3X$; X is a positively charged counterion; with the proviso that when $R_2$ is present, $R_1$ is H or ($C_{1-6}$) alkylcarbonyl; $R_3$ is H or ($C_{1-3}$)alkyl; and L represents a pharmacologically inactive linker moiety having 10-50 atoms; or a pharmaceutically acceptable salt thereof; to pharmaceutical compositions comprising the same as well as to the use of said kisspeptide-pentasaccharide conjugates in the treatment of female infertility.

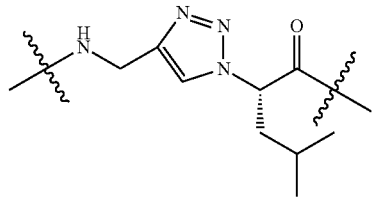

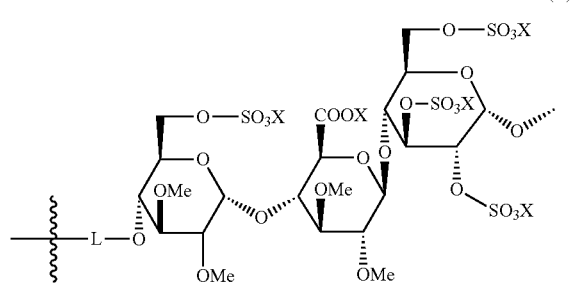

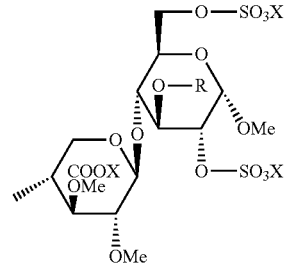

10 Claims, No Drawings

(56) References Cited

FOREIGN PATENT DOCUMENTS

| WO | 2010033207 A1 | 3/2010 |
|---|---|---|
| WO | 2010033224 A1 | 3/2010 |

OTHER PUBLICATIONS

M. deKort, et al., "Conjugation of ATIII-Binding Pentasaccharides to Extend the Half-Life of Proteins: Long-Acting Insulin", Chem. Med. Chem., vol. 3, pp. 1189-1193 (2008).

M. L. Gottsch, et al., "From KISS1 to kisspeptins: An historical perspective and suggested nomenclature", Peptides, vol. 30, pp. 4-9 (2009).

T. Huet, et al., "Long-Lasting Enfuvirtide Carrier Pentasaccharide Conjugates with Potent Anti-Human Immunodeficiency Virus Type 1 Activity", Antimicrobial Agents and Chemotherapy, vol. 54, pp. 134-142 (2010).

K. Knop, et al., "Poly(ethylene glycol) in Drug Delivery: Pros and Cons as Well as Potential Alternatives", Angew. Chem. Int. Ed., vol. 49, pp. 6288-6308 (2010).

J. Roa, et al., "Hypothalamic Expression of KiSS-1 System and Gonadotropin-Releasing Effects of Kisspeptin in Different Reproductive States of the Female Rat", Endocrinology, vol. 47, No. 6, pp. 2864-2878 (2006).

G. M. Vogel, et al., "Antithrombotic Properties of a Direct Thrombin Inhibitor With a Prolonged Half Life and At-Mediated Factor XA Inhibitory Activity", Journal of Thrombosis and Haemostasis, vol. 1, No. 9, pp. 1945-1954 (2003).

B. Yang, et al., "Goldfish kisspeptin: Molecular cloning, tissue distribution of transcript and stimulatory effects on prolactin, growth hormone and luteinizing hormone secretion and gene expression via direct actions at the pituitary level", General and Comparative Endocrinology, vol. 165, pp. 60-71 (2010).

International Search Report of PCT/EP2012/065061, mailed Jul. 11, 2012.

Best, et al., "Click Chemistry and Bioorthogonal Reactions: Unprecendented Selectivity in the Labeling of Biological Molecules", Biochemistry, vol. 48, pp. 6571-6584 (2009).

Jolck, et al., "Solid-Phase Synthesis of PEGylated Lipopeptides Using Click Chemistry", Bioconjugate Chem., vol. 21, pp. 807-810 (2010).

Kolb, et al., "Click Chemistry: Diverse Chemical Function from a few Good Reactions", Angew. Chem. Int. Ed., vol. 40, pp. 2004-2021 (2001).

Lutz, J., "1,3-Dopolar Cycloadditinos of Azides and Alkynes: A Universal Ligation Tool in Polymer and Materials Science", Angew. Chem. Int. Ed., vol. 46, pp. 1018-1025 (2007).

Tietze, et al., "Congugation of p-Aminophenyl Glycosides with Squaric Acid Diester to a Carrier Protein and the Use of Neoglycoprotein in the Histochemical Detection of Lectins", Bioconjugate Chem., vol. 2, pp. 148-153 (1991).

Ni, et al., "Synthesis of Maleimide-Activated Carbohydrates as Chemoselective Tags for Site-Specific Glycosylation of Peptides and Proteins", Bioconjugate Chem., vol. 14, pp. 232-238 (2003).

Shimokawa, et al., "Design, synthesis, and biological evaluation of biotin-labeled (-)ternatin, a potent fat-accumulation inhibitor against 3T3-L1 adipocytes", Bioorganic & Medicinal Chemistry Letters, vol. 19, pp. 92-95 (2009).

Walenga, et al., "Short- and long-acting synthetic pentasaccharides as antithrombotic agents", Expert Opin. Investig. Drug, vol. 14, No. 7, pp. 847-858 (2005).

Gandhi, et al., "Heparin/heparan sulphate-based drugs", Drug Discovery Today, vol. 15, Nos. 23/24, pp. 1058-1069 (2010).

\* cited by examiner

KISSPEPTIDE-PENTASACCHARIDE CONJUGATES

CROSS-REFERENCE TO RELATED APPLICATIONS

This application is a U.S. National Phase application under 35 U.S.C. §371 of PCT/EP2012/065061, filed Aug. 1, 2012, which claims priority from EP application 11176518.6, filed Aug. 4, 2011.

The present invention relates to kisspeptide-pentasaccharide conjugates, to pharmaceutical compositions containing said conjugates and to the use of the conjugates in the treatment of female infertility.

The most common cause of female infertility is ovulatory dysfunction. The most frequent being absent or irregular ovulation due to hypothalamic-pituitary dysfunction associated with normal basal levels of estradiol (WHO group II infertility) of which 80% of are known to be oligo/anovulatory due to polycystic ovarian syndrome (PCOS). The first line treatment for ovulation disorders comprises of a five day oral treatment regimen in the follicular phase of the menstrual cycle with the non-steroidal selective estrogen receptor modulator clomiphene citrate. Although ovulation rates are high after clomiphene citrate treatment (60%-90%), pregnancy rates are relatively low (20%-40%). The discrepancy is explained partly by prolonged anti-estrogenic effect of clomiphene citrate on endometrial receptivity and cervical mucus, due to the relatively long half-life of clomiphene citrate.

The KISS1-receptor (GPR54) plays a critical role in the central regulation of luteinizing hormone (LH) and follicle stimulating hormone (FSH) release (Roa et al, *Endocrinology* 147: 2864-2878, 2006). This has been validated by the infertile phenotype of KISS1R mutations in human and targeted disruption in the KISS1R gene in mice. On the other hand, activating mutations of KISS1R cause precocious puberty. KISS1R agonists lack anti-estrogenic activity and stimulate LH and FSH release, while the risk of overstimulation by kisspeptin is expected to be very low because the negative feedback at the pituitary level stays in tact. Therefore, KISS receptor agonists are perceived as potential new drugs for first line treatment of female infertility, such as ovulation induction (OI), with improved implantation rate compared to clomiphene citrate, the current standard of care.

Kiss1 gene products such as Metastin (Kiss-54) and the Kisspeptins (kisspeptin-14, -13 and -10; for nomenclature see: Gottsch et al *Peptides* 30, 4-9, 2009) are potent endogenous peptide ligands of the KISS1-receptor, but their half-lives are considered too short for therapeutic applications. Kisspeptin-10 derivatives (also named metastin-derivatives or kiss-peptide derivative) having improved stability in blood were disclosed in WO 2006/001499 (Takeda Pharm. Co. Ltd). While the half-lifes of these derivatives in human plasma was enhanced from ~10 minutes for the native kisspeptin-10 to up to several hours, this stabilisation is not considered sufficient for effective applications in treatment of infertility because the small size of these stabilized analogs (<2 kDa) does not prevent them from renal clearance, rendering them only effective after multiple repeated injections.

KISS1-peptide derivatives having enhanced half lifes resulting from covalent attachment of water soluble oligomers, such as polyethylene glycol (PEG), were disclosed in WO 2010/033224 (Nektar Therapeutics). Similarly, PEGylated metastin derivatives, such as kisspeptin-10 derivatives, having improved stability in blood were recently disclosed in WO 2010/013762 (Takeda Pharm. Co. Ltd.).

The in vivo use of PEGylated drugs, including proteins and peptides, is still associated with limitations such as the non-biodegradability of polyethylene glycol, the polydispersity of PEG, potential hypersensitivity reactions and unexpected change in pharmacokinetic behavior (Knop et al, "*Poly(ethylene glycol) in drug delivery: pros and cons as well as potential alternatives*"; Angew. Chem. Int. Ed. 49, 6288-6308, 2010).

An alternative method for the prolongation of the half life of a peptide or a protein consist in the conjugation to a synthetic sulfated oligosaccharide, in particular a pentasaccharide, which has affinity to antithrombin III (AT III) as disclosed in WO 2006/082184 (Akzo Nobel N.V.) and in WO 2008/029278 (Endotis Pharma). Antithrombin III is a serine protease inhibitor which is present in blood. The serum half-life of the oligosaccharide-peptide conjugates was found to be largely determined by the half-life of the pentasaccharide, which is based on its affinity to ATIII. This directing effect of ATIII as a plasma protein carrier on the pharmacokinetic properties of oligosaccharide-peptide conjugates has been confirmed in studies of conjugates of pentasaccharides derived from the anticoagulant idraparinux with the 51-peptide insulin (de Kort et al. "*Conjugation of ATIII-binding pentasaccharides to extend the half-life of proteins: long-acting insulin*"; ChemMedChem 3, 1189-1193, 2008) and with the 36-peptide antiretroviral fusion inhibitor enfuvertide (Huet et al. "*Long-lasting enfuvirtide carrier pentasaccharide conjugates with potent anti-human immunodeficiency virus type 1 activity*", Antimicrob. Agents Chemother. 54, 134-142, 2010).

There remains a need for kisspeptin derivatives having an enhanced in vivo half-life with retainment of potency and a predictable, safe and efficacious profile.

To that aim the present invention provides kisspeptide-pentasaccharide conjugates having the formula (I)

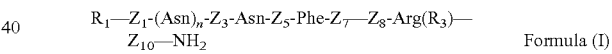

$$R_1-Z_1-(Asn)_n-Z_3-Asn-Z_5-Phe-Z_7-Z_8-Arg(R_3)-Z_{10}-NH_2 \quad \text{Formula (I)}$$

wherein $Z_1$ is Tyr or D-Tyr;

$Z_3$ is Trp, Hyp, Phe or Lys($R_2$);

$Z_5$ is Thr, Aib or Ala;

$Z_7$ is Gly or azaGly;

$Z_8$ is Leu; or $Z_7$ and $Z_8$ together represent

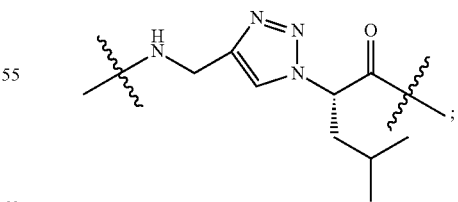

$Z_{10}$ is Phe or Trp;

n is 0 or 1;

$R_1$ or $R_2$, when present, represents a pentasaccharide derivative having the formula (II)

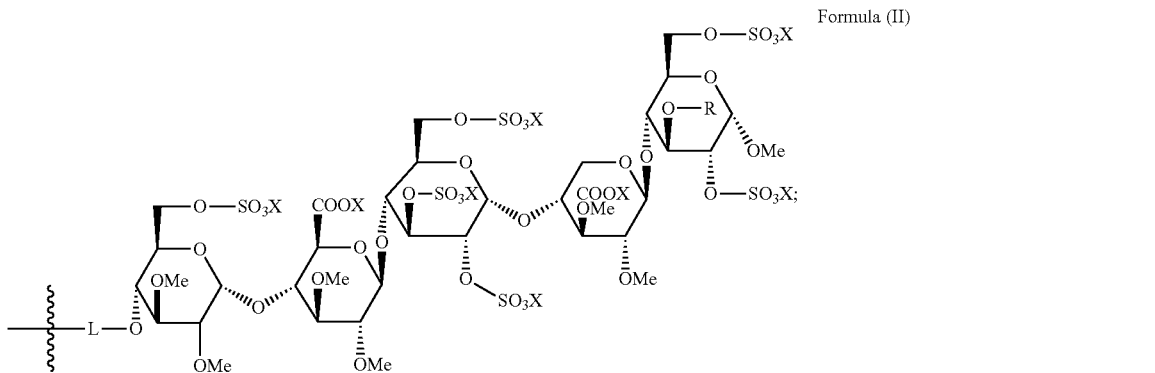

Formula (II)

wherein R is methyl or $SO_3X$;
X is a positively charged counterion;
with the proviso that when $R_2$ is present, $R_1$ is H or $(C_{1-6})$ alkylcarbonyl;
$R_3$ is H or $(C_{1-3})$alkyl; and
L represents a pharmacologically inactive linker moiety having 10-50 atoms; or a pharmaceutically acceptable salt thereof.

The kisspeptide-pentasaccharide conjugates of the invention display not only a vast prolonged half-life in human plasma, but are surprisingly found to retain their kisspeptin in vitro agonistic activity at the human KISS-1 receptor when measured in the presence of human serum (i.e. in the presence of ATIII) and to be extremely stabilized against metabolic degradation of the kisspeptide part of the conjugates of Formula (I).

The kisspeptide-pentasaccharide conjugates of the invention have a therapeutic circulating plasma level of <50 nM. Up to this concentration the ATIII mediated anticoagulant activity of the oligosaccharide is insignificant. Thus, the oligosaccharide used in the conjugates of the present invention has an anticoagulant activity which is of subtherapeutic level when compared to the pharmacological activity of the kisspeptin component of the conjugate.

The term $(C_{1-3})$alkyl as used in the definition of Formula (I) means a branched or unbranched alkyl group having 1-3 carbon atoms, like propyl, isopropyl, ethyl and methyl.

The term $(C_{1-6})$alkyl, as used in the term $(C_{1-6})$alkylcarbonyl, likewise means a branched or unbranched alkyl group having 1-6 carbon atoms, like hexyl, pentyl, butyl, isobutyl, tertiary butyl, propyl, isopropyl, ethyl and methyl.

The pharmacologically inactive linker moiety having 10-50 atoms as used in the definition of Formula (II) means a flexible linking (or spacer) moiety which has 10-50 atoms counted along the "backbone" of the spacer.

The term "pharmacologically inactive" as used herein means that the linker does not contain atoms or groups which show pharmacologically activity per se at the doses at which the compounds of the invention are therapeutically effective. Thus, at doses at which the compounds of the present invention are used as therapeutic drugs, the nature of the spacer does not lead to demonstrable pharmacological side-effects.

The linker structure covalently links the pentasaccharide derivative in Formula (II) at the 4-position of the non-reducing end to an amine function of the kisspeptin-10 peptide analog. This amine function can be the α-amino group of the amino acid residue $Z_1$ of Formula (I) or the ε-amino group of the compound of Formula (I) wherein $Z_3$ represents a residue of lysine.

The linker moiety can comprise 10-50 atoms, more preferably 10-35 atoms and even more preferably 15-30 atoms.

Suitable linkers L comprise one or more (oligo)ethylene glycol groups such as exemplified by:
—$(CH_2CH_2O)_n CH_2CH_2NHC(O)CH_2CH_2$-T-$(CH_2CH_2O)_m CH_2CH_2C(O)$—,
—$(CH_2CH_2O)_n CH_2CH_2NHC(O)CH_2CH_2$-T-$(CH_2CH_2O)_m CH_2C(O)$—,
—$(CH_2CH_2O)_n CH_2CH_2NHC(O)CH_2$—O—$(CH_2CH_2O)_q C(O)CH_2CH_2$-T-$(CH_2CH_2O)_m CH_2CH_2C(O)$—,
—$CH_2CH_2O)_n CH_2CH_2NHC(O)CH_2$—O—$(CH_2CH_2O)_q C(O)CH_2CH_2$-T-$(CH_2CH_2O)_m CH_2C(O)$—,
—$(CH_2CH_2O)_n CH_2CH_2NHC(O)CH_2CH_2$-T-$CH_2CH_2CH_2CH_2C(O)$—,
—$(CH_2CH_2O)_n CH_2CH_2NHC(O)CH_2CH_2SCH_2C(O)$—,
—$(CH_2CH_2O)_n CH_2CH_2NHC(O)CH_2CH_2SCH_2CH_2C(O)$—,
—$(CH_2CH_2O)_n CH_2CH_2NHC(O)CH_2$—O—$(CH_2CH_2O)_m C(O)CH_2CH_2SCH_2CH_2C(O)$—,
—$(CH_2CH_2O)_n CH_2CH_2NH$—U—,
—$(CH_2CH_2O)_n CH_2CH_2NH$—U—NH—$(CH_2CH_2O)_m CH_2CH_2C(O)$—,
—$(CH_2CH_2O)_n CH_2CH_2NHC(O)CH_2$—O—$(CH_2CH_2O)_m$—$CH_2CH_2NH$—U—
wherein m, n or q may be 0-30;
T is 1,2,3-triazol-1,4-diyl;
U is cyclobut-3-ene-1,2-dione-3,4-diyl; and wherein the left side of the linker as depicted is attached to the pentasaccharide part of Formula (II) and its right side is attached to the Kisspeptide part of Formula (I).

Preferred are linkers L selected from:
—$(CH_2CH_2O)_n CH_2CH_2NHC(O)CH_2CH_2$-T-$(CH_2CH_2O)_m CH_2CH_2C(O)$—,
—$(CH_2CH_2O)_n CH_2CH_2NHC(O)CH_2CH_2$-T-$(CH_2CH_2O)_m CH_2C(O)$—,
—$(CH_2CH_2O)_n CH_2CH_2NHC(O)CH_2$—O—$(CH_2CH_2O)_q C(O)CH_2CH_2$-T-$(CH_2CH_2O)_m CH_2CH_2C(O)$—,
—$CH_2CH_2O)_n CH_2CH_2NHC(O)CH_2$—O—$(CH_2CH_2O)_q C(O)CH_2CH_2$-T-$(CH_2CH_2O)_m CH_2C(O)$—,
—$(CH_2CH_2O)_n CH_2CH_2NHC(O)CH_2CH_2$-T-$CH_2CH_2CH_2CH_2C(O)$—,
wherein m, n or q may be 0-30; and
T is 1,2,3-triazol-1,4-diyl.

More preferred linkers are:
—$(CH_2CH_2O)_n CH_2CH_2NHC(O)CH_2CH_2$-T-$(CH_2CH_2O)_m CH_2CH_2C(O)$—,
—$(CH_2CH_2O)_n CH_2CH_2NHC(O)CH_2CH_2$-T-$(CH_2CH_2O)_m CH_2C(O)$—, —(CH$_2$CH$_2$O)$_n$CH$_2$CH$_2$NHC(O)CH$_2$—O—(CH$_2$CH$_2$O)$_q$C(O)CH$_2$CH$_2$-T-(CH$_2$CH$_2$O)$_m$CH$_2$CH$_2$C(O)—, —CH$_2$CH$_2$O)$_n$CH$_2$CH$_2$NHC(O)CH$_2$—O—(CH$_2$CH$_2$O)$_q$C(O)CH$_2$CH$_2$-T-(CH$_2$CH$_2$O)$_m$CH$_2$C(O)—, —(CH$_2$CH$_2$O)$_n$CH$_2$CH$_2$NHC(O)CH$_2$CH$_2$-T-CH$_2$CH$_2$CH$_2$CH$_2$C(O)—;

wherein n=2-10, m=2-10 and q=2-10; and
T is 1,2,3-triazol-1,4-diyl.

Particular preferred linkers are
—(CH$_2$CH$_2$O)$_n$CH$_2$CH$_2$NHC(O)CH$_2$CH$_2$-T-(CH$_2$CH$_2$O)$_m$CH$_2$CH$_2$C(O)—, —(CH$_2$CH$_2$O)$_n$CH$_2$CH$_2$NHC(O)CH$_2$CH$_2$-T-(CH$_2$CH$_2$O)$_m$CH$_2$C(O)— and —(CH$_2$CH$_2$O)$_n$CH$_2$CH$_2$NHC(O)CH$_2$CH$_2$-T-CH$_2$CH$_2$CH$_2$CH$_2$C(O)—;

wherein n=2-4 and m=0-4; and
T is 1,2,3-triazol-1,4-diyl.

There is a preference for kisspeptide-pentasaccharide conjugates of Formula (I), wherein $Z_5$ is Thr. Further preferred are the kisspeptide-pentasaccharide conjugates of Formula (I), wherein in addition $R_3$ is methyl. Also preferred are the conjugates of Formula (I) wherein also n is 0; $Z_1$ is D-Tyr; $Z_3$ is Hyp and $Z_{10}$ is Trp. Other preferred conjugates of the invention are those of Formula (I) wherein n is 1 and $Z_{10}$ is Phe. Further preferred are the kisspeptide-pentasaccharide conjugates of Formula (I), wherein R is methyl, corresponding to conjugates wherein the pentasaccharide derivative contains 6 sulfate groups. Conjugates of the invention wherein R is methyl generally have a diminished affinity of the conjugate for ATIII and a resulting enhancement in potency in the presence of serum, as compared with the conjugates of Formula (I) wherein R is SO$_3$X.

Specifically preferred kisspeptide-pentasaccharide conjugates of the invention are:

Conjugate C7
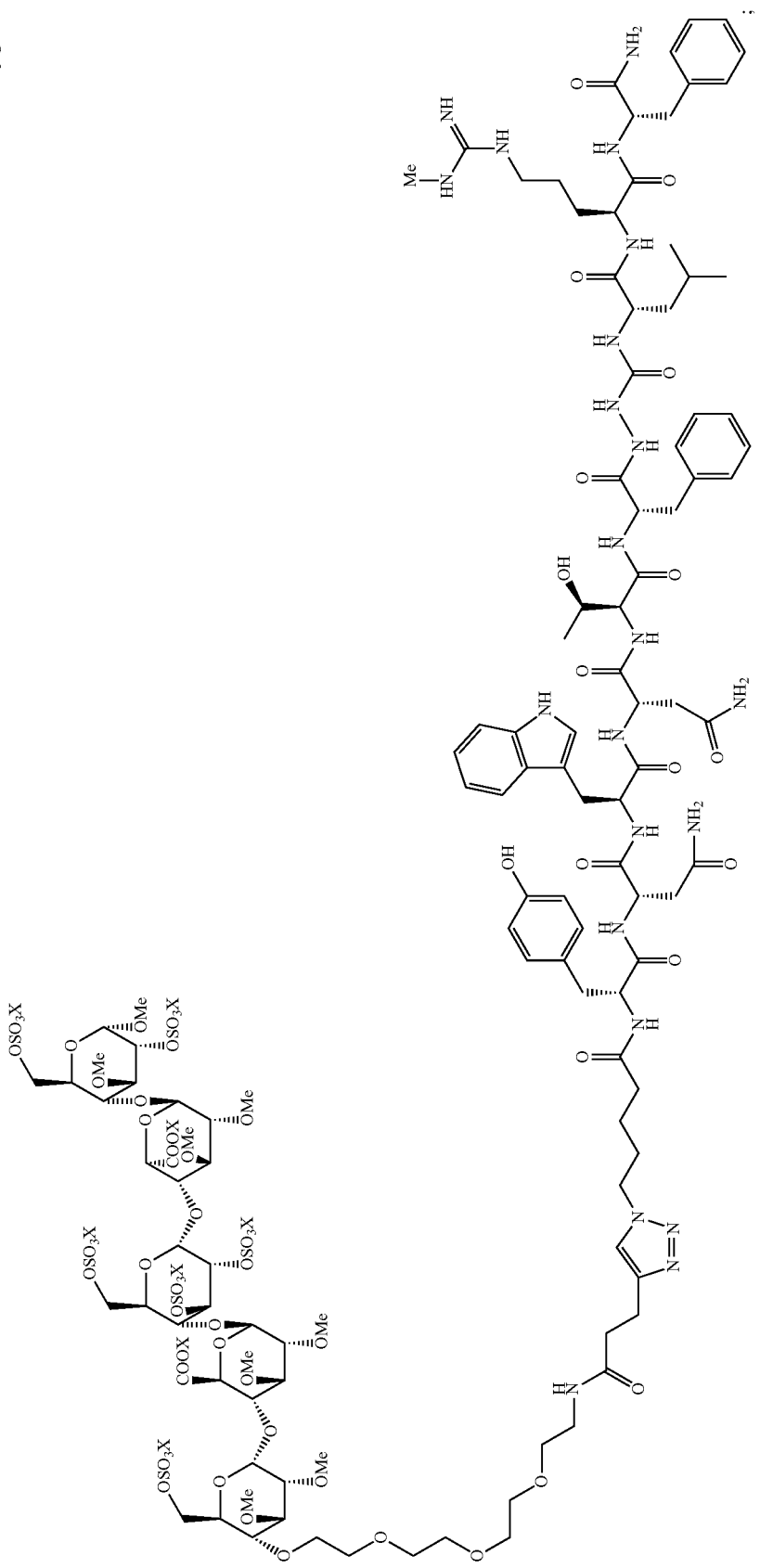

-continued
Conjugate C8
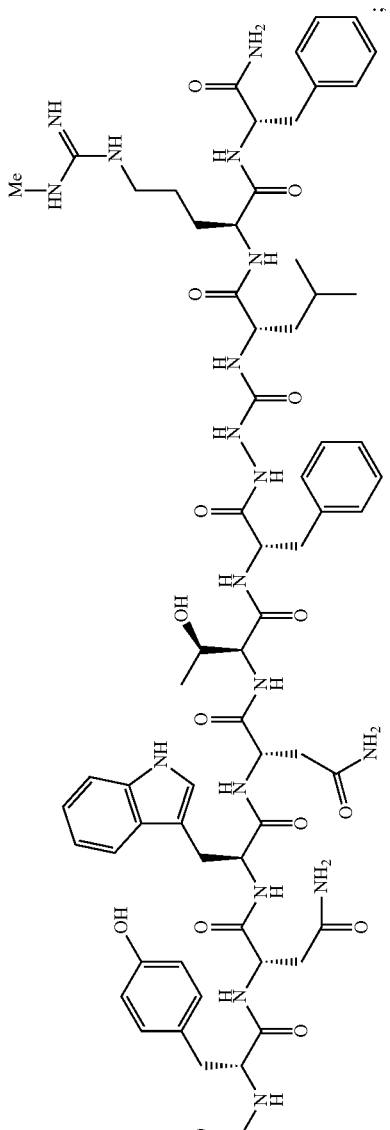
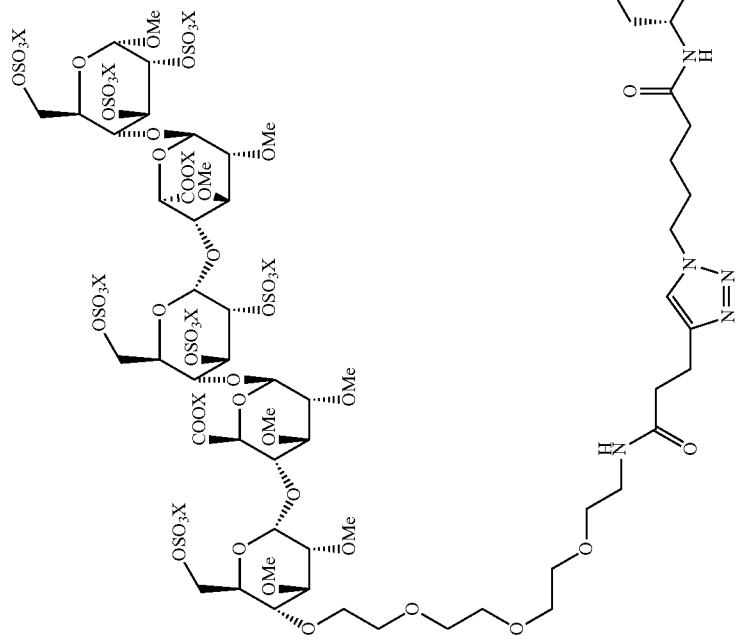
X = Na+

-continued
Conjugate C22
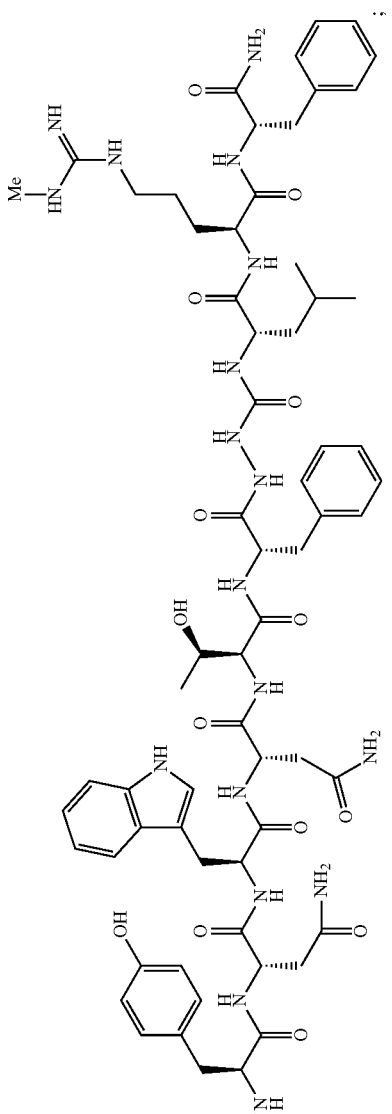
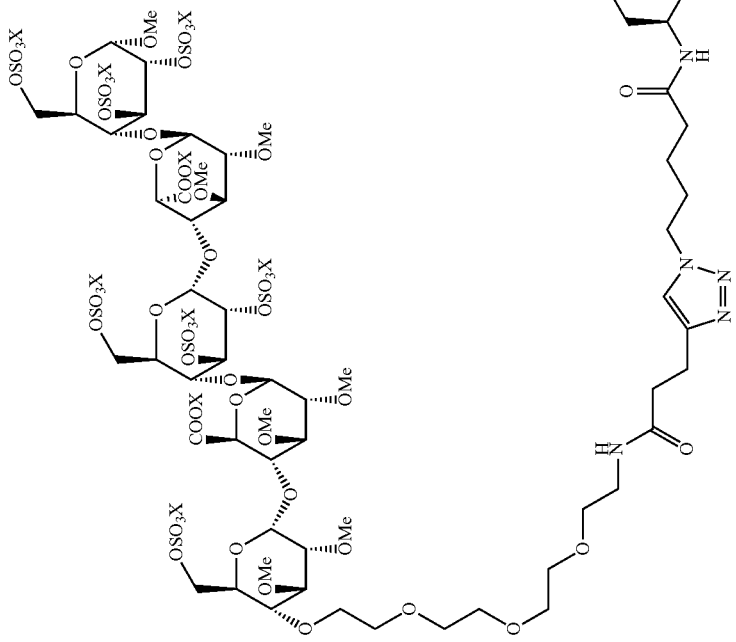
X = Na+

Conjugate C30
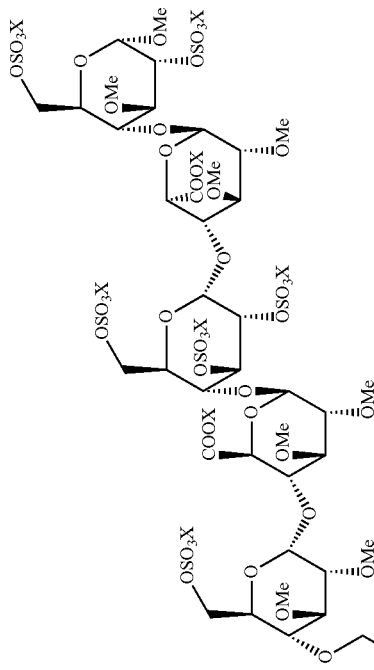
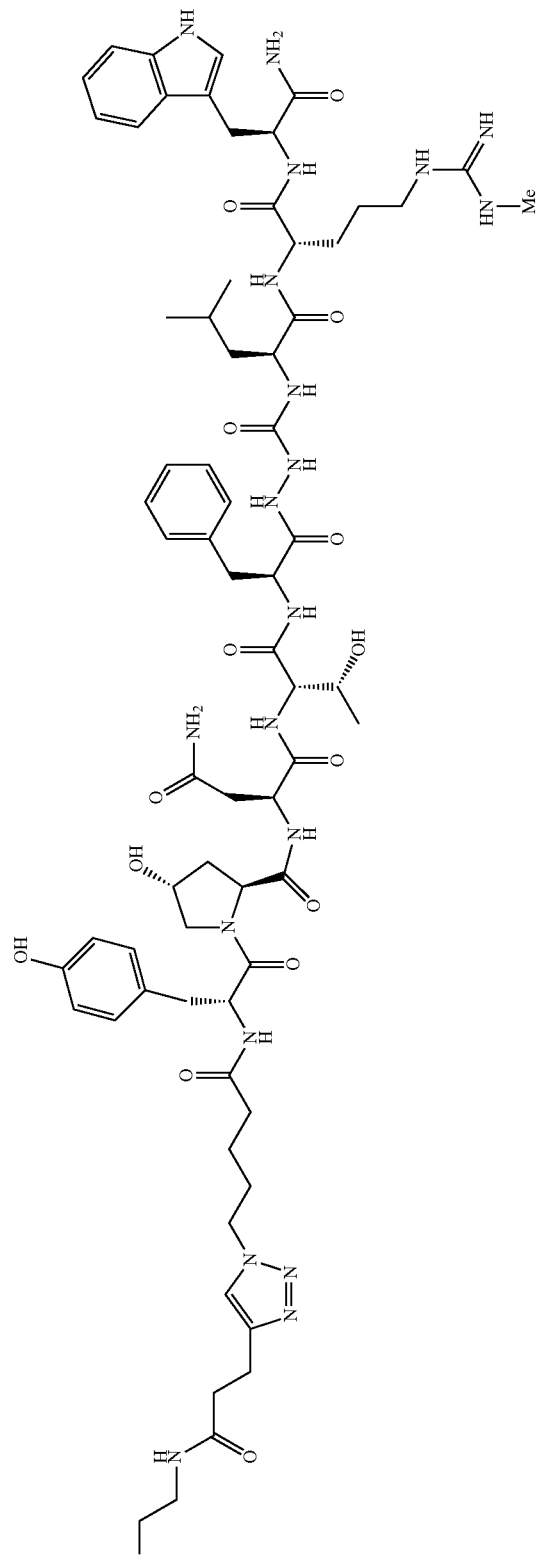
X = Na+

-continued
Conjugate C36
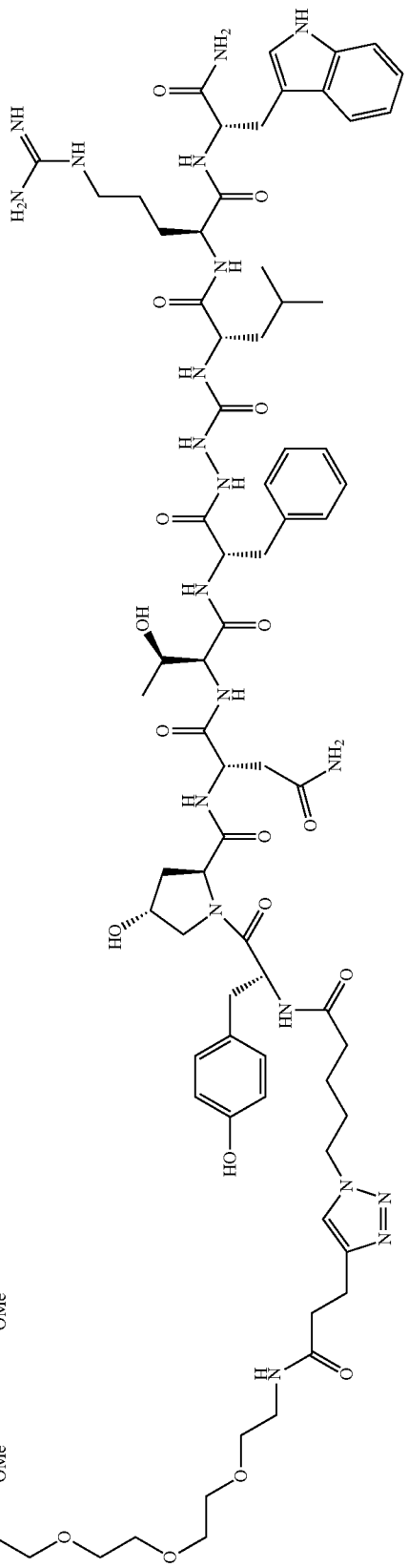
X = Na+

-continued
Conjugate C37
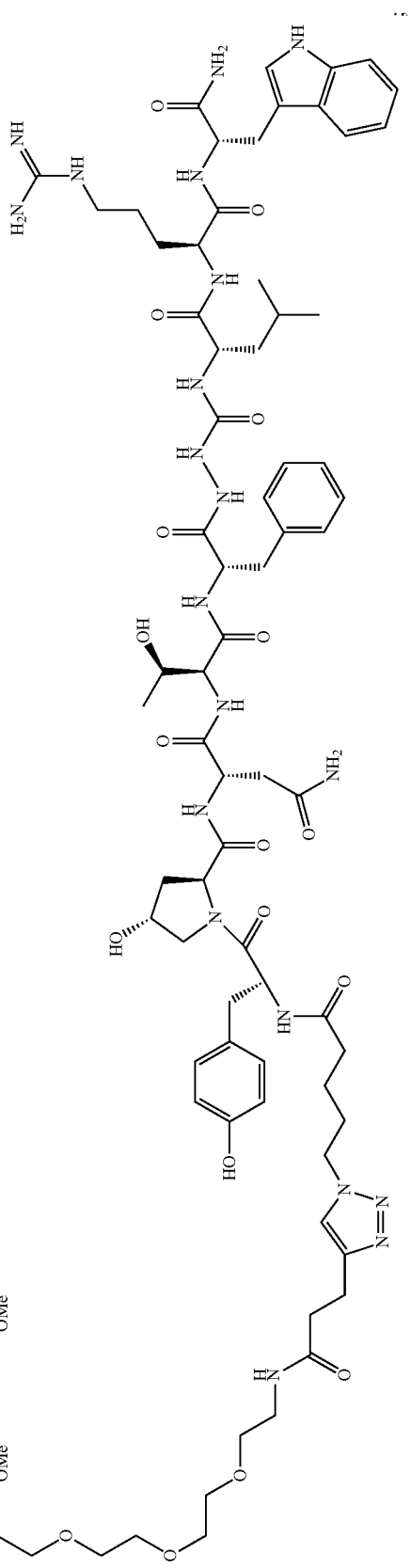
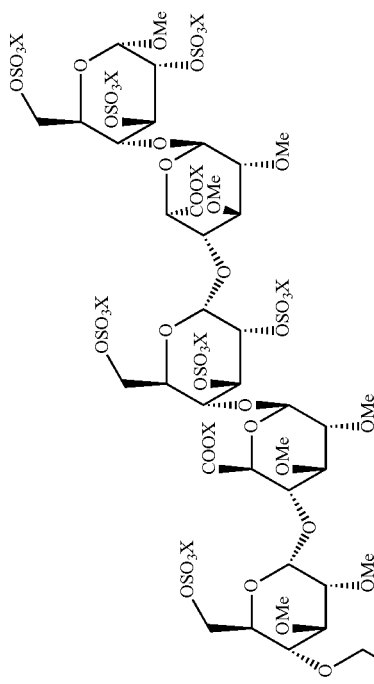
X = Na+

Conjugate C38
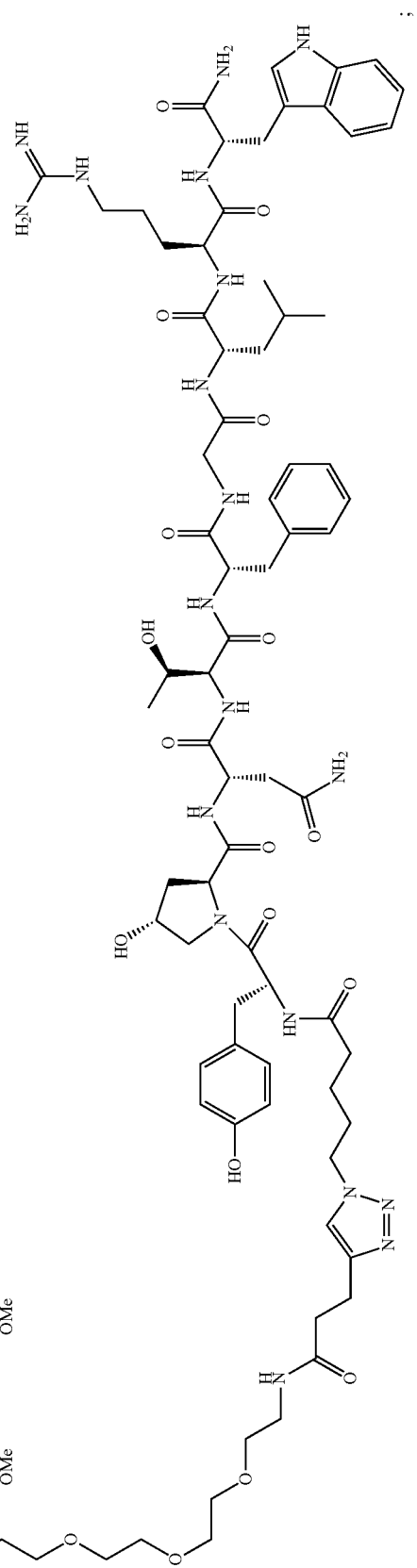

Conjugate C39
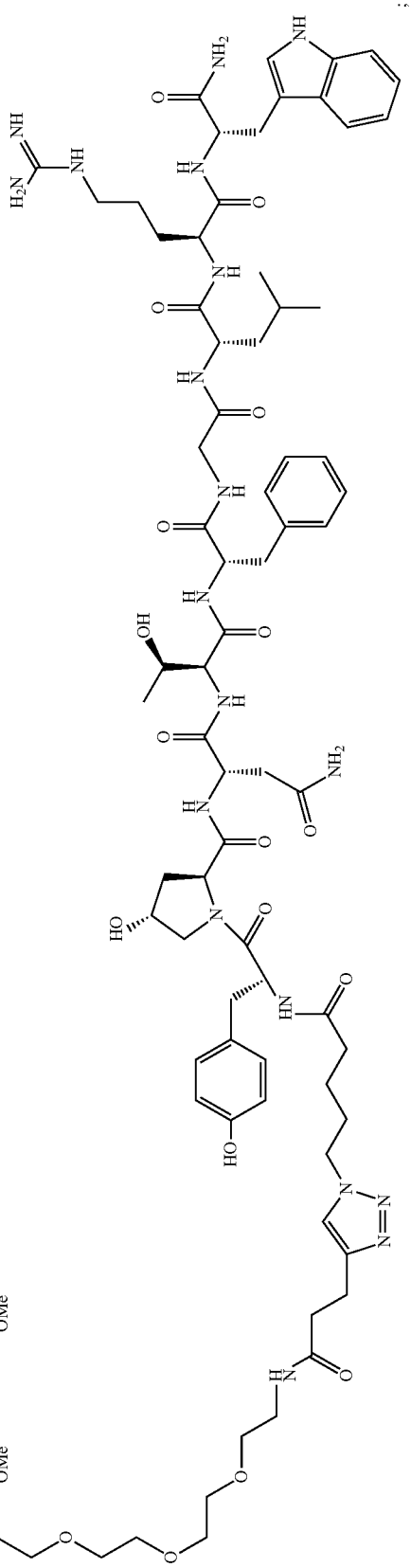
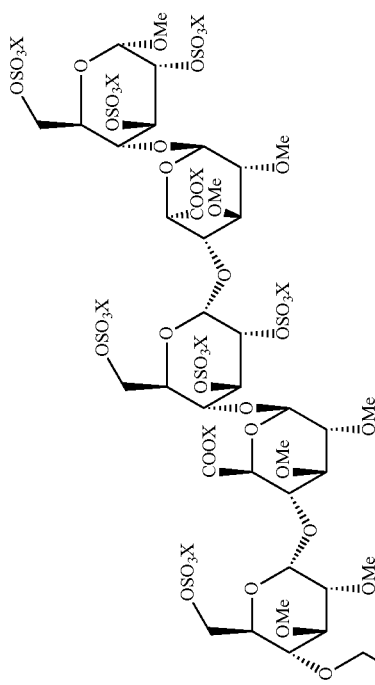

Conjugate C31
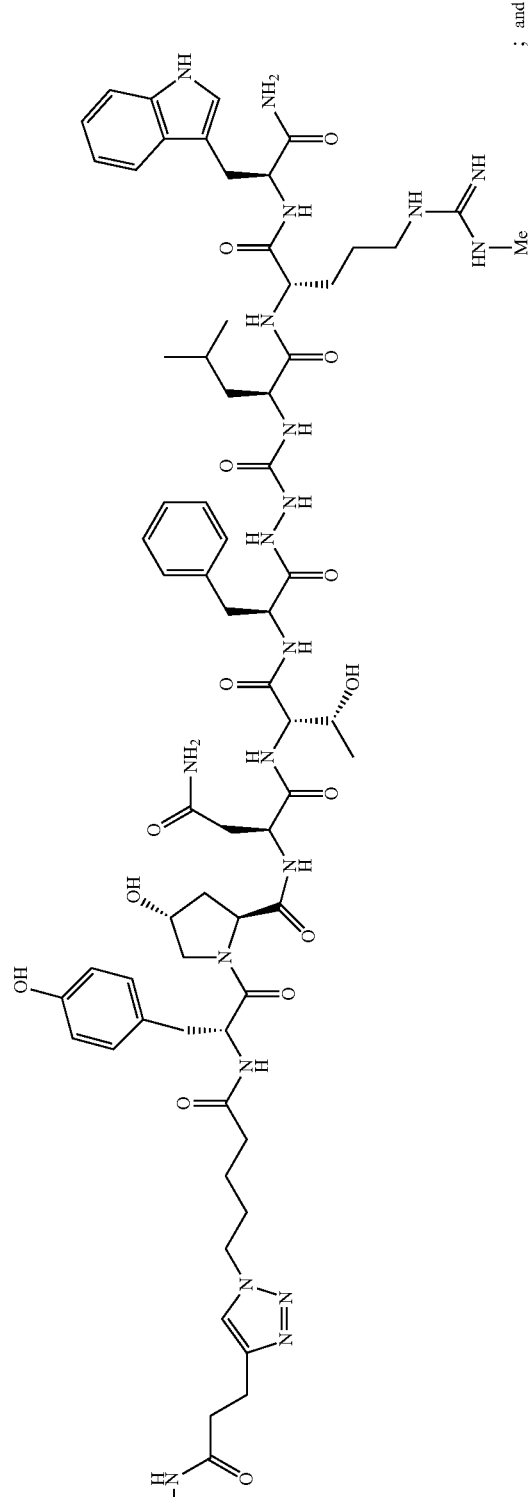
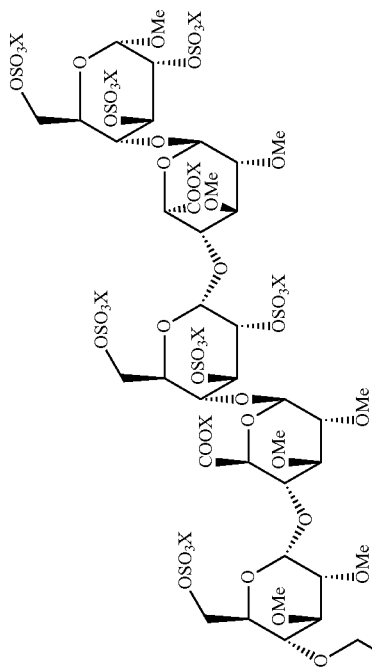
X = Na+ ; and

Conjugate C41
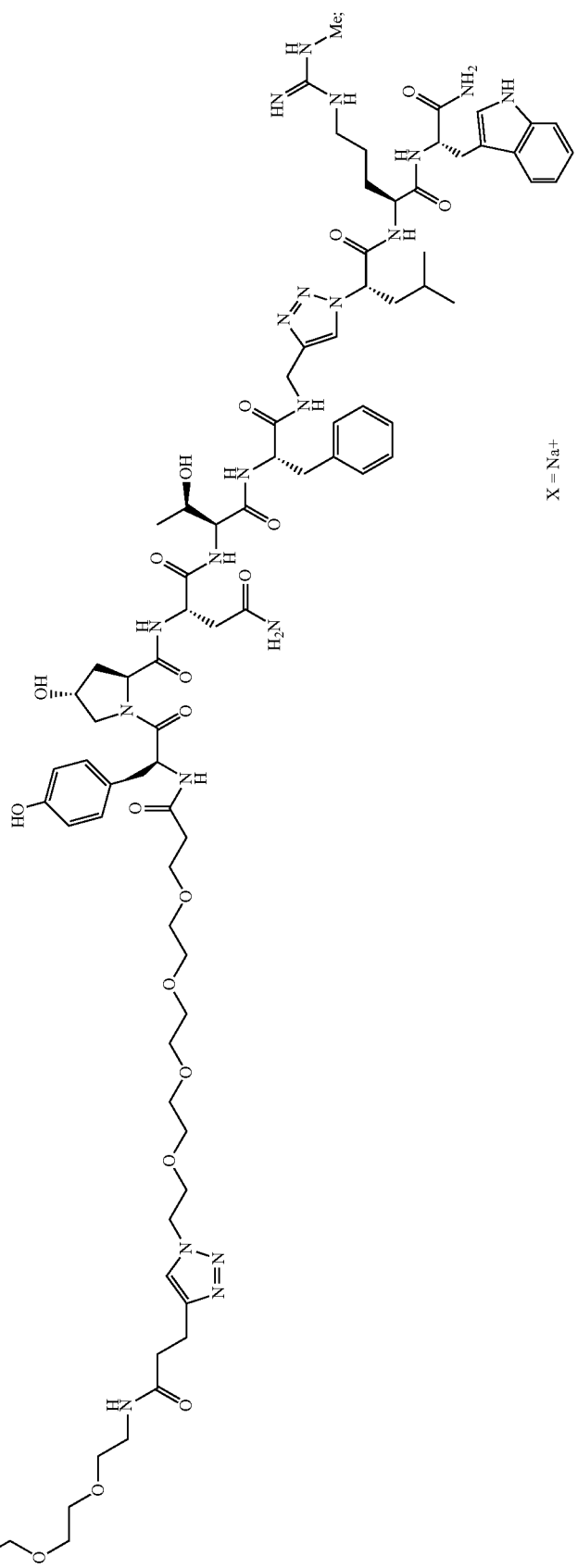

or a pharmaceutically acceptable salt thereof.

The kisspeptide-pentasaccharide conjugates of the invention may be prepared by methods known in the art of bioorganic chemistry in general.

The conjugates of the invention according to Formula (I) can be prepared by a stepwise assembly of an optionally modified kisspeptide (KP) analog and a synthetic pentasaccharide (PS) derivative, followed by a process in which the linker L is formed by a coupling step linking the kisspeptide analog and the pentasaccharide derivative by a covalent bond.

The synthetic pentasaccharide (PS) derivative can be represented by Formula (III), wherein R represents methyl or $SO_3X$; X is a positively charged counterion;

which the kisspeptide analog and the pentasaccharide derivative are linked by a coupling reagent.

Optional modifications of and processes for linking the kisspeptide analog and the pentasaccharide derivative can be accomplished by well known methods in the art. General synthetic methods for the production of bioconjugates are described in "*Bioconjugate Techniques*" by Greg T. Hermanson, 2nd edition, 2008, Academic Press and "*Bioconjugation Protocols*" by Christof M. Niemeyer, 2004, Methods in Molecular Biology, Vol. 283, Humana Press; "*Chemical Reagents for Protein Modification*" by Roger L. Lundblad, $3^{rd}$ edition, 2005, CRC Press; D. Crich, *Reagents for Glycoside, Nucleotide and Peptide Synthesis*, Wiley, Chichester,

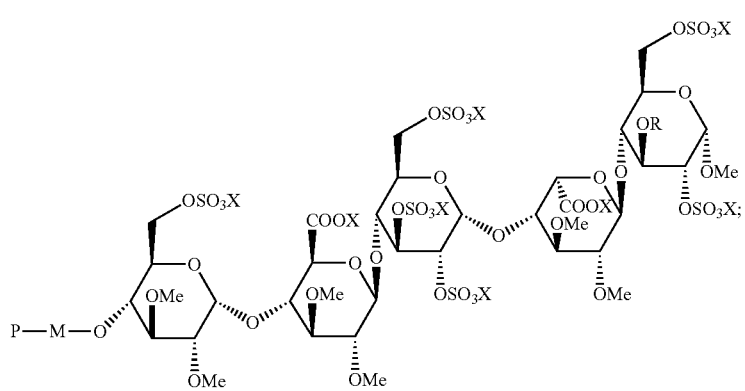

Formula (III)

M represents part of the pharmacologically inactive linker moiety L, where L has the meaning as earlier defined; and P is a functional group, such as $NH_2$, $N_3$, thiol, alkyn, bromoacetyl and the like, which can engage in a conjugation reaction with a modified kisspeptide (KP) analog of either Formula (IV) or Formula (V), wherein $Z_1$, $Z_3$, $Z_5$, $Z_7$, $Z_8$, $Z_{10}$, $R_3$, n and M have the earlier defined meanings and wherein $P_1$ and $P_2$ independently represents a functional group, such as $NH_2$, $N_3$, thiol, alkyne, bromoacetyl and the like.

$P_1$-M-$Z_1$-(Asn)$_n$-$Z_3$-Asn-$Z_5$-Phe-$Z_7$—$Z_8$-Arg($R_3$)—
$Z_{10}$—$NH_2$     (Formula IV);

$R_1$—$Z_1$-(Asn)$_n$-Lys(M-$P_2$)-Asn-$Z_5$-Phe-$Z_7$—$Z_8$-Arg
($R_3$)—$Z_{10}$—$NH_2$     (Formula V);

The conjugation method may comprise (a) an optional step wherein the kisspeptide analog is adapted for conjugation with a reactive group, (b) an optional step wherein the pentasaccharide derivative is adapted for conjugation with a reactive group and either (c) a coupling step wherein the optionally adapted kisspeptide analog is conjugated with the pentasaccharide-spacer molecule, wherein the pentasaccharide is extended at the non-reducing end with a spacer that is optionally modified with a reactive group, or (d) a step in 2005 and M. A. Gauthier et al. *Peptide/protein-polymer conjugates: synthetic strategies and design concepts Chem. Commun.* 2008, 2591-2611. In addition, a Staudinger ligation (such as described by K. L. Kiick et al. Proc. Nat. Acad. Sci. 2002; 99:19-24) may be considered for conjugation. Alternatively, enzymatic reactions such as the regioselective IgA protease mediated elongation of polypeptides at the N-terminus (as described by M. Lewinska et al. in Bioconjugate Chem. 2004; 15: 231-234) or the transglutaminase catalyzed introduction of amino spacer containing oligosaccharides (as described by M. Sato et al. in J. Am. Chem. Soc. 2004; 126: 14013-14022) can be adapted for conjugation of a pentasaccharide spacer residue to an optionally modified kisspeptide analog.

In one method of conjugation a pentasaccharide derivative having a (protected) thiol function is coupled to a kisspeptide analog that contains a halide function, such as a bromoacetyl group as described in P. Schelté et al. *Bioconjugate Chem.* 2000, 11, 118-123.

Thiol-bromide Conjugation Method (A)

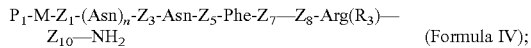

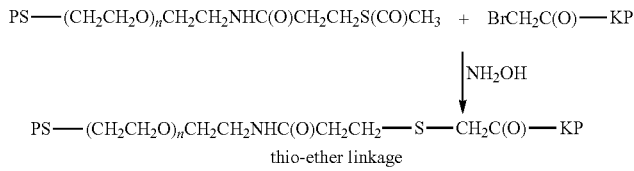

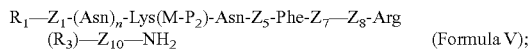
thio-ether linkage wherein PS represents the pentasaccharide part of Formula (II) and KP represents the Kisspeptide part of Formula (I).

In an alternative method of conjugation, a Huisgen's 1,3-dipolar cycloaddition to form a triazole linker is used for conjugation of a pentasaccharide derivative and a kisspeptide analog, that have been independently modified with an alkyne or azide functional group. The 1,3-dipolar cycloaddition can be accomplished in a copper(I) catalyzed fashion and can optionally be accelerated by the use of a tailored ligand such as described in S. I. Presolski et al. *J. Am. Chem. Soc.* 2010, 132, 14570-14576; and by Jean-Francois Lutz, "1,3-*Dipolar Cycloadditions of Azides and Alkynes A Universal Ligation Tool in Polymer and Materials*"; Angew. Chem. Int. Ed. 2007, 46, 1018-1025.

Cycloaddition Conjugation Method (C)

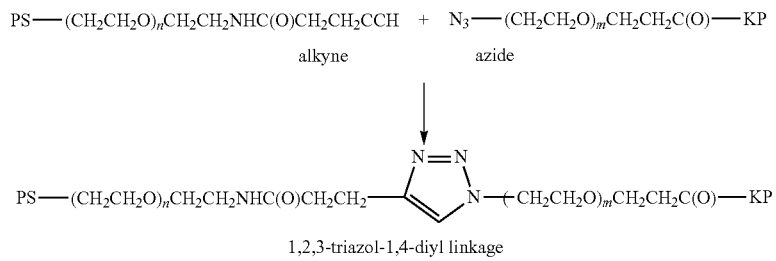

Alternatively, metal-free methods of triazole linker formation can be applied as described in M. F. Debets et al. Chem-BioChem 2010, 11, 1168-1184.

In another method of conjugation, a kisspeptide (KP) analog having a primary amine function and a synthetic pentasaccharide (PS) derivative having a primary amino function can be conjugated with the use of a homobifunctional reagent, such as for example 1,2-diethoxycyclobutene-3,4-dione (squaric acid diester; Lutz et al., Bioconjugate Chem. 2, 148-153, 1991).

Squarate Conjugation Method (B)

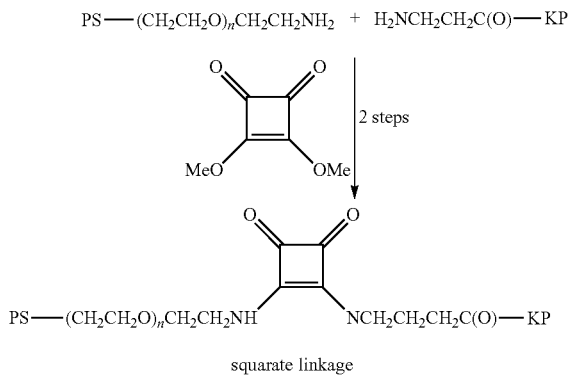

Further alternative bioorthogonal conjugation reactions were recently reviewed by Michael D. Best, "*Click Chemistry and Bioorthogonal Reactions: Unprecedented Selectivity in the Labeling of Biological Molecules*", Biochemistry 2009, 48, 6571-6584.

The required kisspeptide (KP) analog of either Formula (IV) or Formula (V) can be prepared by methods known in the art, such as solution phase peptide synthesis and manual or automated solid phase peptide synthesis (SPPS), or by a combination thereof.

The peptide coupling can be carried out by methods commonly known in the art for the coupling—or condensation—of peptide fragments such as by the azide method, mixed anhydride method, activated ester method, the carbodiimide method using DCC, or carbodiimide hydrochloride (ED-Cl.HCl); or, preferably, under the influence of ammonium/uronium salts like 2-(1H-benzotriazol-1-yl)-1,1,3,3-tetramethyluronium tetrafluoroborate (TBTU), especially with the addition of catalytic and racemisation suppressing compounds like N-hydroxy-succinimide, N-hydroxybenzotriazole and 7-aza-N-hydroxybenzotriazole (HOBt, HOAt, HOOBt, etc.). Overviews are given in The Peptides, Analysis, Synthesis, Biology, Vol. 3, E. Gross and J. Meienhofer, eds. (Academic Press, New York, 1981), Peptides: Chemistry and Biology, N. Sewald and H.-D. Jakubke (Wiley-VCH, Weinheim, 2002) and Chemistry of Peptide Synthesis, N. L. Benoiton (CRC Taylor & Francis, 2005).

SPPS is well known in the art (Merrifield, R. B. *J. Am. Chem. Soc.*, 85, 2149-2154 (1963), and is widely employed by commercial suppliers. (See also Sewald, N. *Peptides: Chemistry and Biology*, Wiley-VCH, 2003 and Bodanszky, *Principles of Peptide Synthesis*, Springer-Verlag, Heidelberg (1984)). There are several known variations on the general approach. (See, for example, "*Peptide Synthesis, Structures, and Applications*" 1995 by Academic Press, Chapter 3 and White (2003) *Fmoc Solid Phase Peptide Synthesis, A practical Approach*, Oxford University Press, Oxford).

Methods for obtaining a peptide in the form of a C-terminal amide, such as in peptide derivatives of Formula (I), include, for example, solid phase synthesis using resins (e.g Rink amide) for the formation of peptide amides. Alternatively, the carboxyl group of the terminal amino acid is first protected by amidation and the peptide chain is subsequently extended from the amino group side to a desired length.

In an alternative fashion, the peptide can be assembled by classical solution phase synthesis or in a combination of classical SPPS and solution phase synthesis, such as described in I. F. Eggen et al. *J. Peptide Sci.* 11, 633-641 (2005), I. F. Eggen et al. *Org. Proc. Res. Dev.,* 9, 98-101 (2005) and EP1277761.

After completion of the reaction on the solid support or in solution, the product may be purified and isolated by a combination of conventional purification methods such as solvent extraction, column chromatography, liquid chromatography, trituration and recrystallization. When the peptide obtained by the above methods is in a free form, the peptide can be converted into an appropriate salt; conversely when the peptide is obtained in a salt form, it can be converted into its free form or an alternative salt form by methods known in the art.

When the kisspeptide analog of the conjugate of the invention is present in the form of a configurational isomer, each diastereomer or conformer can optionally be isolated by separation and purification as mentioned above. In addition, when the compound of the present invention is racemic, it can be separated into its enantiomers by the conventional means of optical resolving.

The kisspeptide analog may optionally contain stabilizing and/or potency enhancing structural elements or the peptide isosteric replacements such as aza-glycine or triazole moieties. The preparation of azapeptides by SPPS or solution phase synthesis is well known in the art. For introduction of aza-glycine, 4-nitrophenyl chloroformiate and Fmoc-NH—NH$_2$.TFA can be used to extend the optionally immobilized tripeptide intermediate at the N-terminus as in Formula VI.

a) 4-NO$_2$PhOCOCl+H-Leu-Arg(R$_3$)—Z$_{10}$-
RinkResin→4-NO$_2$PhOC(O)-Leu-Arg(R$_3$)—
Z$_{10}$-RinkResin b) 4-NO$_2$PhOC(O)-Leu-Arg(R$_3$)—Z$_{10}$-RinkResin+
Fmoc-NH—NH$_2$.TFA→Fmoc-NH—NH—
CONH-L-R—F-RinkResin          Formula (VI)

Alternatively, the reagents in Formula (VII) can be prepared for introduction of the aza-glycine using phosgene according to *J. Org. Chem.* 64, 7388 (1999).

Formula (VII)

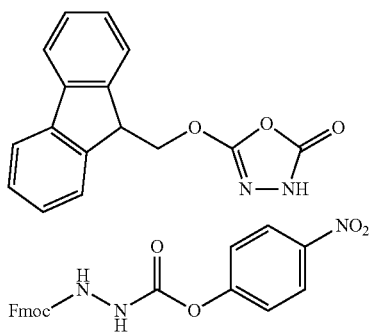

In addition, the aza-kisspeptide can be assembled in a chemoselective silver catalyzed coupling of a thioester derivative according to N. Olivier et al. Bioconjugate Chem. 2009, 20, 1397-1403. Subsequently, the Fmoc-protected aza-Gly intermediate can be converted into a nonapeptide or decapapetide kisspeptide analog by means of known methods for solution or solid phase peptide synthesis. Suitable aza-kisspeptide analogs for compounds of the present invention have been described in WO2004063221 or WO2006001499.

Peptide isosteric elements, such as the 1,4-(1,2,3-triazole) group in the definition of Formula (I) wherein Z$_7$ and Z$_8$ together represent

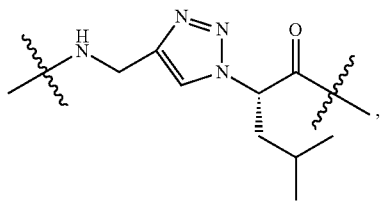 [SMILES: *NCc1cn([C@@H](CC(C)C)C(*)=O)nn1]

can be introduced by the condensations of azide and alkyne containing peptide fragments as in A. Brik et al. *Chem. Bio-*

*Chem* 6, 1167-1169 (2005) or J. Springer, et al. *Eur. J. Org. Chem.* 15, 2592-2600 (2008). Preferably, the azide is present at the N-terminal position of the growing peptide chain and the alkyne is present at the C-terminal end of the incoming peptide building block or peptide chain as in Formula (VII), wherein R$_5$ may be a suitable temporary amino protecting group (such as Fmoc or Boc) and R$_6$ is H, a suitably amide protecting group or a covalent linkage to a resin from which the kisspeptide analog is cleaved according to a process as described above. Similarly, the introduction and of the azide function and the subsequent cycloaddition can be accomplished as above. The growing triazole kisspeptide analog can then be further processed either by solution phase or solid phase peptide synthesis, or a combination thereof, into the peptide analogs as depicted in Formula (IV) and (V).

Formula (VIII)

AND Enantiomer

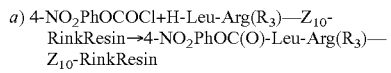

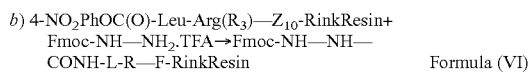

AND Enantiomer

The ATIII-binding pentasaccharide derivative according to Formula (III) can be prepared using methods described by Van Boeckel and Petitou in *Angew. Chem. Intl. Ed. Engl.* 32, 1671-1690 (1993) and by C. Chen et al. in *Biorg. Med. Chem. Lett.* 19, 3875-3879, 2009.

The kisspeptide-pentasaccharide conjugates of the present invention may be purified according to well-known methods as described in H. Ahmed, Principles and Reactions of Protein Extraction, Purification and Characterization, CRC Press, 2005, M.-I. Aguilar, HPLC of Peptides and Proteins, Methods and Protocols, Humana Press, New Jersey, 2004 and K. M. Gooding and F. E. Regnier, HPLC of Biological Macromolecules, Marcel Dekker Inc., New York, 2002. Preferred methods of purification involve anion and/or cation exchange chromatography, hydrophobic interaction chromatography, size exclusion chromatography and high performance liquid chromatography (HPLC). Most preferred methods of purification include anion exchange chromatography and HPLC.

Furthermore, the compounds of the invention, which may occur in the form of a free base, may be isolated from the reaction mixture in the form of a pharmaceutically acceptable salt. The pharmaceutically acceptable salts may also be obtained by treating the free base of Formula (I) with an organic or inorganic acid such as hydrogen chloride, hydrogen bromide, hydrogen iodide, sulfuric acid, phosphoric acid, acetic acid, propionic acid, glycolic acid, maleic acid, malonic acid, methanesulphonic acid, fumaric acid, succinic acid, tartaric acid, citric acid, benzoic acid, ascorbic acid and the like.

The kisspeptide-pentasaccharide conjugates of this invention or intermediates thereof may possess chiral carbon atoms, and may therefore be obtained as a pure enantiomer, or as a mixture of enantiomers, or as a mixture containing diastereomers. Methods for obtaining the pure enantiomers are well known in the art, e.g. crystallization of salts which are obtained from optically active acids and the racemic mixture, or chromatography using chiral columns. For diastereomers straight phase or reversed phase columns may be used.

The present invention further provides pharmaceutical compositions comprising a kisspeptide-pentasaccharide conjugates according to Formula (I), or a pharmaceutically acceptable salt thereof, in admixture with pharmaceutically acceptable auxiliaries, and optionally other therapeutic agents. The term "acceptable" means being compatible with the other ingredients of the composition and not deleterious to the recipients thereof. Compositions include e.g. those suitable for parenteral administration, such as intravenous, intraperitonial, subcutaneous, intramuscular, transdermal administration, and the like. Preferred routes of administration are the subcutaneous and intramuscular route.

Pharmaceutical compositions for parenteral administration may contain 0.01-25 mg/ml of a kisspeptide-pentasaccharide conjugate in an aqueous solution buffered at a pH between 3 and 8, preferably between 4-6. A preferred composition of the invention comprises an aqueous buffered solution comprising 5% (w/w/) mannitol and 6 mM sodiumacetate buffered at pH 5.

For parenteral administration, the pharmaceutical composition of the invention may be presented in unit-dose or multi-dose containers, e.g. injection liquids in predetermined amounts, for example in sealed vials and ampoules, and may also be stored in a freeze dried (lyophilized) condition requiring only the addition of sterile liquid carrier, e.g. water, prior to use. For parenteral administration, aqueous suspensions, isotonic saline solutions and sterile injectable solutions may be used, containing pharmaceutically acceptable dispersing agents and/or wetting agents, such as propylene glycol or butylene glycol, as described in the standard reference, Gennaro, A. R. et al, Remington: *The Science and Practice of Pharmacy* (20th Edition, Lippincott Williams & Wilkins, 2000, see especially Part 5: Pharmaceutical Manufacturing), The invention further includes a pharmaceutical composition, as hereinbefore described, in combination with packaging material suitable for said composition, said packaging material including instructions for the use of the composition for the use as hereinbefore described. The conjugates of the invention may be administered to humans in a unit dose comprising 0.01-10 mg of conjugate, preferably 0.1-5 mg and more preferred 0.1-2 mg. In a preferred regimen for the treatment of female infertility a single unit dose per menstrual cycle is applied subcutaneously.

The kisspeptide-pentasaccharide conjugates of the invention were found to be agonists of the KISS receptor.

In vitro assays to determine the biological activity of KISS receptor agonists are well-known in the art. In general, cells expressing the KISS receptor are incubated with the compound to be tested and the stimulation of a functional response is determined. To measure a functional response, isolated DNA encoding the KISS receptor gene, preferably the human receptor, is expressed in a suitable host cell-line. Such a host cell-line might be the Chinese Hamster Ovary (CHO) cell-line, but other cell-lines can also be used. Preferably, the host cells are of mammalian origin (Jia et al (1991) *Mol Endocrinol* 5, 759-776).

Methods to construct KISS receptor-expressing cell lines are well-known in the art (e.g., Sambrook et al., Molecular Cloning: A Laboratory Manual, Cold Spring Harbor Laboratory Press, latest edition). Heterologous expression of the receptor is obtained by transfection and expression of the DNA encoding the desired protein. Techniques for PCR and construction of suitable expression systems are also well-known in the art. The DNA encoding the desired protein can be constructed synthetically using standard solid phase techniques, preferably to include restriction sites for ease of ligation. Suitable control elements for transcription and translation of the included coding sequence can be provided to the DNA coding sequences. As is well-known, expression systems are available, which are compatible with a wide variety of hosts, including prokaryotic hosts such as bacteria and eukaryotic hosts such as yeast, plant cells, insect cells, avian cells, mammalian cells, and the like.

Cells expressing the receptor are then incubated with the test compound to determine stimulation of a functional response.

The KISS receptor is a family-A G-protein coupled receptor (GPCR) that couples via the $G_{\alpha q}$-protein to the Phospholipase C/Calcium$^{2+}$ signal transduction pathway. The generation of Calcium$^{2+}$ in the presence of a KISS agonists can be determined in the FLIPR assay, in which a Calcium$^{2+}$ sensitive fluorescent dye is used as a sensor for intracellular Calcium$^{2+}$ (Hansen KB and Bräuner-Osborne H (2009) *Methods Mol Biol* 552, 269-78). Upstream of Calcium$^{2+}$, the Inositol Phosphate cascade can be measured by detection of IP1 accumulation in cells using Homogeneous Time-Resolved Fluorescence (HTRF) assay (Cassutt K J et al (2007) *J of Biomol Screening* 12, 285-287).

In addition to the direct measurement of Calcium$^{2+}$ levels in the KISS receptor-expressing cell-line, cell-lines may be transfected with a second cDNA that encodes a reporter gene, of which the expression is dependent on the intracellular concentration of Calcium$^{2+}$. In general, reporter gene expression might be controlled by any response element reacting to changing levels of intracellular Calcium$^{2+}$ e.g. NFAT-response element. Suitable reporter genes are e.g. the genes encoding beta-galactosidase, alkaline phosphatase, firefly luciferase and green fluorescent protein. The principles of such transactivation assays are well-known in the art and are described for example in Stratowa et al (1995) *Curr Opin Biotechnol* 6, 574. Agonistic compounds may also be identified in assays that are based on receptor-induced recruitment of beta-arrestin to the agonist-occupied receptor (e.g., Transfluor® assay, PathHunter® and Tango™ beta-arrestin assays) or receptor internalization assays (e.g., PathHunter® endocytosis assays). Label-free assays may also be applicable to screen for KISS receptor agonists. These assays are based on receptor-induced dynamic mass redistribution of intracellular content or receptor-induced changes in cell morphology or adhesion (Van Koppen (2010) "*Generic Assays in G-protein-coupled Receptor Drug Discovery*"; Drug Discovery 7, 69-72).

The kisspeptide-pentasaccharide conjugates of the invention showed in vitro agonistic activity at the $G\alpha_q$-coupled human KISS receptor, as measured in the absence and in the presence of 20% human serum in a NFAT-regulated luciferase reporter gene assay. When tested at $10^{-8}$ M in the presence of 20% human serum the conjugates of the invention demonstrates more than 50% stimulation of the effect induced by Kisspeptin-10. A pEC$_{50}$ of higher than 8 in the presence of 20% human serum (in the presence of ATIII) indicates that the conjugates of the invention may be active in vivo at a human dose devoid of anti-coagulant activity.

The kisspeptide-pentasaccharide conjugates of the invention were found to be remarkably stable against proteolytic degradation upon in vitro stability testing in human serum (Tomita et al, (2008) *J. Med. Chem.* 51 (23), 7645-7649). Moreover the kisspeptide-pentasaccharide conjugates were also found to be stable in vivo as determined in pharmacokinetic studies.

Assays to detect levels of intact kisspeptide-pentasaccharide conjugates in human serum (both from in vitro serum stability testing and in vivo PK studies) are well-known in the art, such as assays method employing an antibody directed against the conjugate (e.g. in an Enzyme-linked immunosorbent assay, ELISA or Radio Immuno Assay, RIA, Dhillo W et al (2007) *J Clin Endocrinol Metab* 92, 3958-3966), in a competition assay with radioactive-labeled Kisspeptides (e.g. a KISS receptor binding assay or RIA), in a bio-activity assay (e.g. Calcium$^{2+}$ measurements in cells expressing the KISS receptor, see above) or by liquid chromatography-mass spectrometry (LC-MS, McCormack A L et al. (1997) *Anal. Chem.* 69 (4), 767-776).

Conjugates of the present invention are characterized by a potency that is sufficient to provide effective therapeutic plasma levels <50 nM and an in vitro serum stability of the conjugate that matches the in vivo half-life (>24-120 h in human).

The kisspeptide-pentasaccharide conjugates of the invention can be used in the treatment of female infertility. The conjugates can have further utility in the treatment of (metastatic) cancer (especially hormone-dependent cancers like prostate cancer and breast cancer) and in the treatment of endometriosis and hot flushes in breast cancer. In addition, the kisspeptide-pentasaccharide conjugates of the invention can also be used in other mammals than human.

EXPERIMENTAL

Abbreviations

Aib aminoisobutyric acid
ACN acetonitrile
Boc t-butyloxycarbonyl
BSA bovine serum albumin
CHO Chinese hamster ovary
CV column volume
DCM dichloromethane
DIEA diisopropyl ethyl amine
DIC diisopropyl carbodiimide
DMF N,N-dimethylformamide
$EC_{50}$ effective concentration resulting in 50% of the maximum response
EDCl 1-(3-dimethylaminopropyl)-3-ethylcarbodiimide hydrochloride
ESI electrospray ionization
Fmoc 9-fluorenylmethoxycarbonyl
HPLC high pressure liquid chromatography
HOBt 1-hydroxybenzotriazole
Hyp 3-hydroxyproline
(LC)MS (liquid chromatography) mass spectrometry
Mbs p-methoxybenzenesulfonyl
MTBE tert-butyl methyl ether
Mtr 4-methoxy-2,3,6-trimethylbenzenesulfonyl
Mts mesitylene-2-sulfonyl
NMM N-methyl morpholine
Np para-nitrophenol
Pbf 2,2,4,6,7-pentamethyldihydrobenzofuran-5-sulfonyl
Plmc 2,2,5,7,8-pentamethylchroman-6-sulfonyl
RP reversed phase
Sc subcutaneous
TBTU 2-(1H-benzotriazol-1-yl)-1,1,3,3-tetramethyluronium tetrafluoroborate
TFA trifluoroacetic acid
Tos tosyl
Trt trityl
UV ultraviolet
Vis visible
Z benzyloxycarbonyl Materials and Methods Analytical Methods HPLC Analysis

TABLE

LC methodology for purity determination (representative method A)

| | | | |
|---|---|---|---|
| Column | XBridge C18, 3.5 µm, 2.1 × 100 mm | | |
| Column Temp. (C.°) | 40 | | |
| Flow (ml/min) | 0.25 | | |
| Sample concentration | 0.5 mg/mL in H$_2$O | | |
| Injection volume | 10 | | |
| Detection (nm) | 210 | | |
| | T (min)* | 25 mM Ammonium-acetate in H$_2$O/ACN 1/9 | 25 mM Ammonium-acetate in H$_2$O/ACN 9/1 |
| Gradient: | 0 | 0 | 100 |
| | 30 | 50 | 50 |
| | 31 | 100 | 0 |
| | 34 | 100 | 0 |
| | 35 | 0 | 100 |
| | 37 | 0 | 100 |
| | 38 | 100 | 0 |
| | 40 | 100 | 0 |
| | 41 | 0 | 100 |
| | 43 | 0 | 100 |
| | 44 | 100 | 0 |
| | 46 | 100 | 0 |
| | 47 | 0 | 100 |
| | 48 | 0 | 100 |
| | 49 | 100 | 0 |
| | 51 | 100 | 0 |
| | 52 | 0 | 100 |
| | 60 | 0 | 100 |

Method B:
A: 25 mM NH$_4$Ac in H$_2$O+10% ACN, B: ACN+10% 25 mM NH$_4$Ac in H2O. 0→80% B in 30 min, flow 0.25 mL/min)

Method C:
A: 25 mM NH$_4$Ac in H$_2$O+10% ACN, B: ACN+10% 25 mM NH$_4$Ac in H$_2$O. 10->50% B in 30 min, flow 0.25 mL/min Method D:
A: 25 mM NH$_4$Ac in H$_2$O+10% ACN, B: 25 mM NH$_4$Ac in ACN/H2O 8/2. 10→50% B in 30 min, flow 0.25 mL/min Method E (Applied with LCMS):
A: 25 mM NH$_4$Ac in H$_2$O/ACN 9:1 v/v, B: 25 mM NH$_4$Ac in H$_2$O/ACN 1:9 v/v. 10→80% B in 30 min Mass Spectrometry Analysis Absorption spectra were recorded on a ATI Unicam Ltd. UV2 UV/Vis spectrometer. The spectrometer was controlled via Vision 3.4 software running on a personal computer. Typical experimental parameters were 2 nm resolution and using a computerized optimal scan time. High-resolution MS spectra were acquired on a Bruker Daltonics MicroTOF-Q time-of-flight mass spectrometer. Spectra were recorded using electrospray ionization (ESI) in positive ion mode unless indicated otherwise. The instrument was controlled via HyStar 3.2 software running on a personal computer.

Typical experimental parameters for MS were: 200° C. Dry Heater temperature. Nitrogen gas was used as both drying and nebulising gas, where the drying gas flow rate was 4.0 L·min−1 and the nebuliser pressure 1.4 bar. For positive ion mode, summation of 5000 spectra were acquired with a window of 300-3000 m/z. External calibration was obtained by infusing a mixture of Agilent tune mix 1:100 in ACN for 0.5 min at the end of the experiment. The nominal resolution of the instrument was 19000, FWHH, the accuracy <5 ppm. A Dionex Ultimate 3000 HPLC system was used for injection at a flow rate of 50 ul·min−1; for chromatographic method descriptions see below. Typical sample concentrations were 0.5 mg/ml.

Synthetic Methods

Pentasaccharide Synthesis

Scheme I. Preparation of pentasaccharide derivatives 1-10.
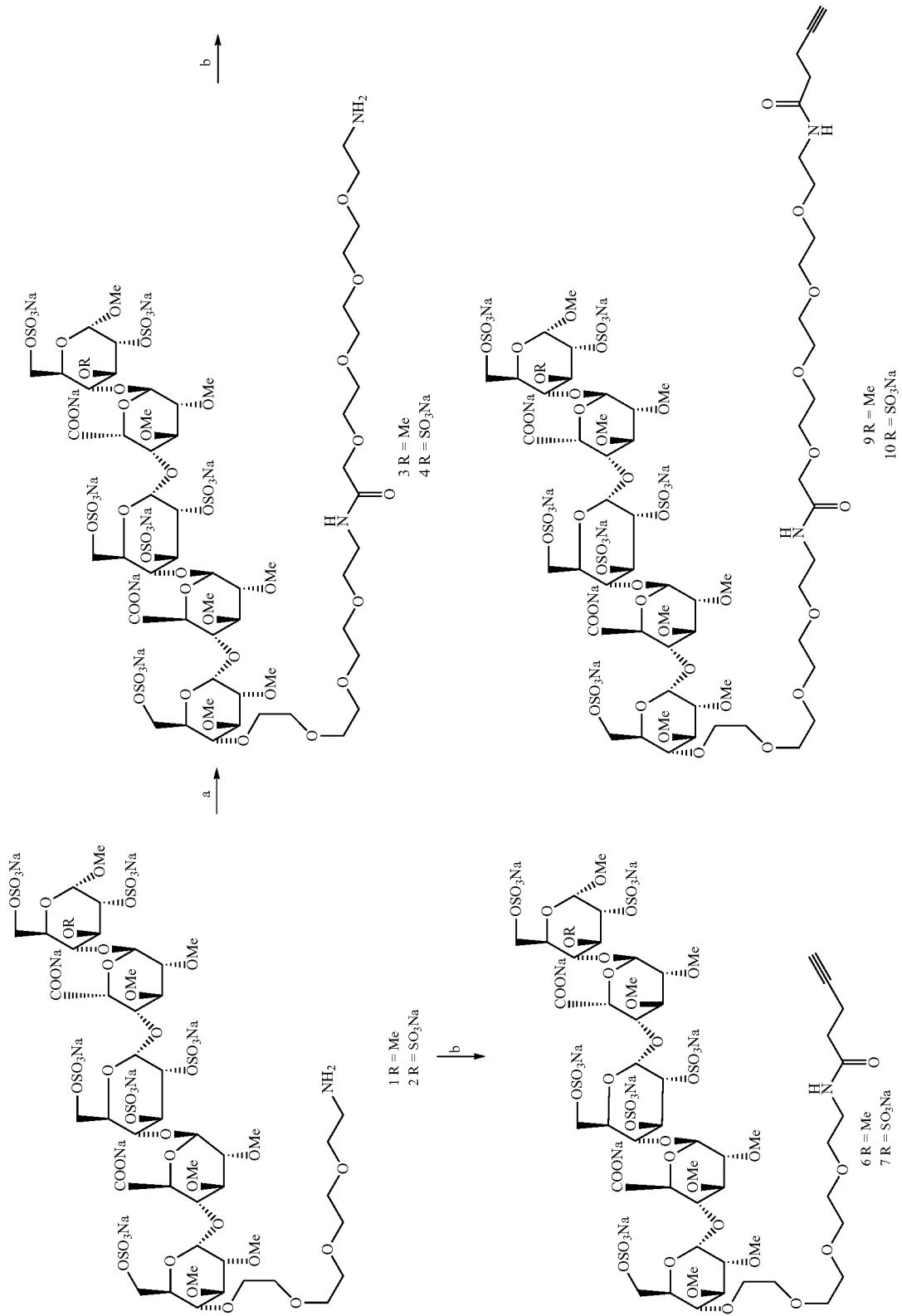

-continued
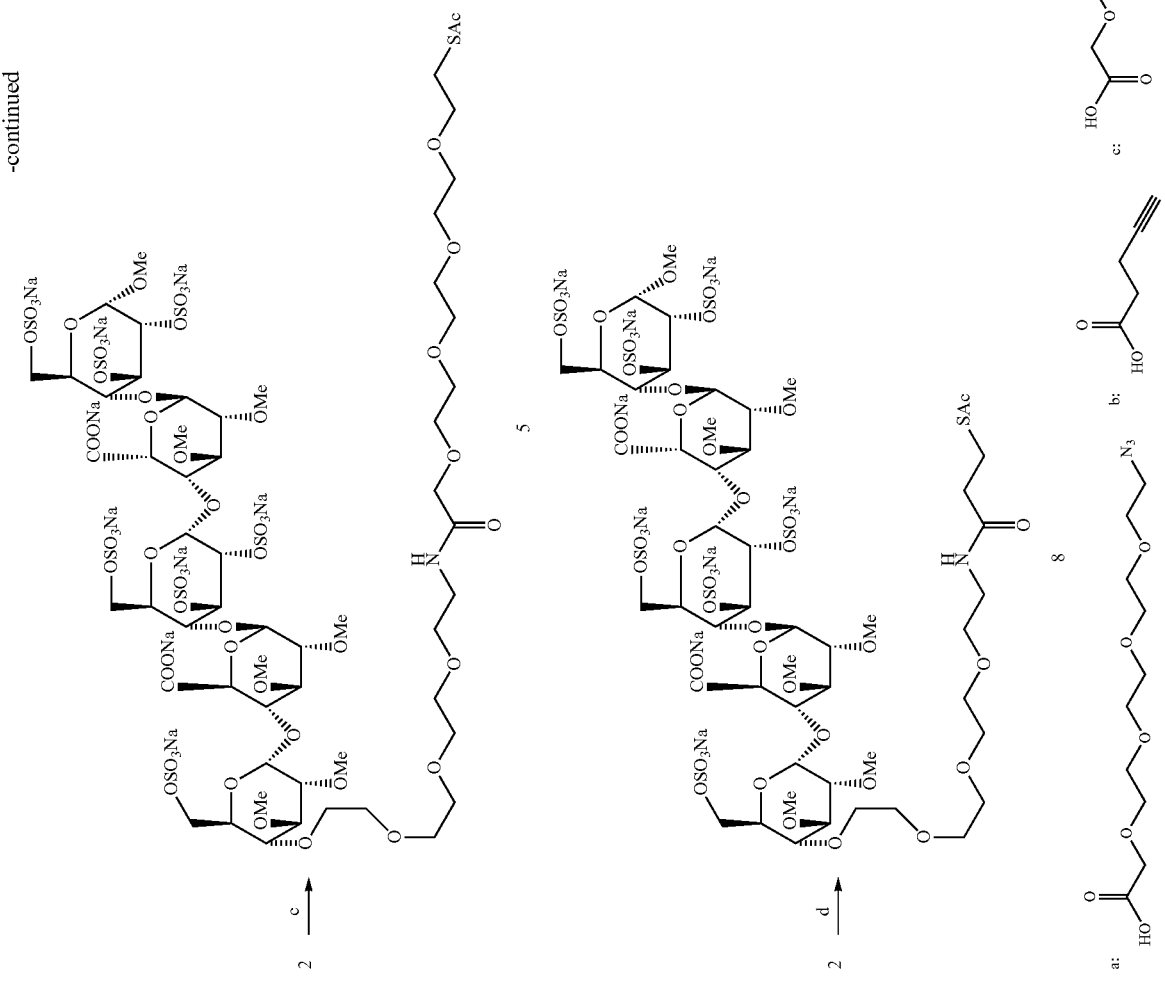

Pentasaccharides 1, 2 and 5 were prepared as described in International Patent Application WO2006/082184 (Akzo Nobel N.V.)

Pentasaccharide 3

14-azido-3,6,9,12-tetraoxatetradecan-1-oic acid (compound a, 0.581 mmol, 161 mg) was dissolved in 8 mL DMF and NMM (0.953 mmol, 0.105 ml, 96 mg) was added, followed by the addition of TBTU (0.572 mmol, 184 mg). The mixture was stirred for 20 min. Then Pentasaccharide 1 (0.318 mmol, 600 mg) was added as a solid. The mixture was stirred for another 2 h and was subsequently concentrated under reduced pressure. The residue was dissolved in water, filtered over PVDF 0.45 um filter and purified by Q-Sepharose® ion exchange chromatography. The fractions containing conjugated azide were collected and desalted by Sephadex® G-25 gel filtration chromatography. Yield: 650 mg (95%). Next, the conjugated azide (0.088 mmol, 190 mg) was dissolved in t-BuOH/water (1:1, v/v, 20 mL). The solution was degassed, placed under an atmosphere of nitrogen and Pd/C (0.422 mmol, 50 mg) was added. The heterogeneous mixture was degassed and placed under an atmosphere of hydrogen which was lead through the solution for 18 h. The hydrogen gas was replaced by nitrogen and the solution was filtered and concentrated under reduced pressure to give Pentasaccharide 3 as the free amine in 90% yield. Using the same procedure pentasaccharide 4 was prepared staring from pentasaccharide 2.

Pentasaccharide 6

Pentynoic acid (compound b; 1.455 g, 14.84 mmol, 1.5 eq) was dissolved in DMF (15 mL). HOBt (2.205 g, 16.32 mmol, 1.65 eq) and EDCl (2.84 g, 14.84 mmol, 1.5 eq) were added and stirred for 1 h at r.t. A solution of Pentasaccharide 1 (18.68 g, 9.89 mmol, 1 eq) in DMF (200 mL) was added drop wise the reaction mixture and stirred for 2 h. Water (300 mL) was added before the reaction mixture was extracted with DCM 3 times. The water layer was filtered and the remaining DCM was removed under reduced pressure. The remaining water layer was eluted on to a Q-Sepharose column (CV 450 mL) and eluted with 0.2 M NaCl(aq) (2 CV), 0.2 M to 1.0 M (20 CV) and 2.0 M (2 CV). The solution collected was concentrated under reduced pressure to a smaller volume before desalting on a Sephadex G25 column. After lyophilizing the solution, compound 6 (16.5 g, 8.38 mmol 85%) was isolated.

Using the same procedure pentasaccharide 7 was prepared staring from pentasaccharide 2.

Pentasccharide 9 or 10 were prepared from pentasaccharides 3 or 4, respectively, as described for the conversion of the pentasaccharide 1 or 2 into 6 or 7, respectively.

Synthesis of Kisspeptides:

Kisspeptide analogues of Formula (IV) and Formula (V) were prepared by using solid phase peptide synthesis by commercial suppliers. Kisspeptides analogues wherein $Z_7$=azaGly were prepared as described in WO2007072997, WO2006001499 or WO2004063221. Kisspeptide analogues of Formula (IV) or Formula (V) wherein $Z_7$ and $Z_8$ together represent

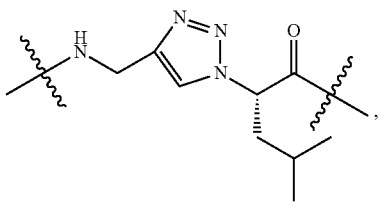 [SMILES: *NCc1cn([C@@H](CC(C)C)C(*)=O)nn1]

were prepared by incorporation of azidoleucine according to *Org. Lett.* 2001, 3, 781-783 or by conversion of leucine into azidoleucine according to Org. Lett. 2007, 9, 3797-3800, followed by formation of the triazole peptide according to *J. Org. Chem.* 2007, 72, 7963-7967 or *Org. Lett.* 2006, 8, 4505-4507. Kisspeptides analogues wherein $R_3$=Me were prepared by incorporation of Fmoc-Arg(Me,Pbf)-OH as a commercially available amino acid building block. Kisspeptides analogues wherein $Z_3$=azidolysine were prepared by incorporation of commercially available amino acid building block Fmoc-azido-lysine.

Introduction of the $P_1$-M group as defined in Formula (IV) was performed either as the penultimate step in the solid phase synthesis procedure by an acylation step with the appropriate commercially available linking reagent (e.g. azidopentanoic acid), or by subjecting the peptide in solution to the corresponding mixed anhydride derivative that was freshly prepared as described for instance in *Peptides* Volume 5, Issue 2, 1984, 167-168.

TABLE A

Formula (IV)

Kisspeptides analogues: $P_1$—M—$Z_1$-(Asn)$_n$-$Z_3$-Asn-$Z_5$-Phe-$Z_7$—$Z_8$-Arg($R_3$)—$Z_{10}$—NH$_2$

| Peptide | P$_1$—M | Z$_1$ | n | Z$_3$ | Z$_5$ | Z$_7$ | Z$_8$ | R$_3$ | Z$_{10}$ |
|---|---|---|---|---|---|---|---|---|---|
| P1 | BrCH$_2$(CO) | D-Tyr | 1 | Trp | Thr | azaGly | Leu | Me | Phe |
| P2 | [squarate-OMe] | D-Tyr | 1 | Trp | Thr | azaGly | Leu | Me | Phe |
| P3 | [squarate-OMe with NH—(CH$_2$CH$_2$O)$_4$—CH$_2$C(O)] | D-Tyr | 1 | Trp | Thr | azaGly | Leu | Me | Phe |

TABLE A-continued

Kisspeptides analogues: $P_1$—M—$Z_1$-(Asn)$_n$-$Z_3$-Asn-$Z_5$-Phe-$Z_7$—$Z_8$-Arg($R_3$)—$Z_{10}$—$NH_2$    Formula (IV)

| Peptide | $P_1$—M | $Z_1$ | n | $Z_3$ | $Z_5$ | $Z_7$ | $Z_8$ | $R_3$ | $Z_{10}$ |
|---|---|---|---|---|---|---|---|---|---|
| P4 | $N_3(CH_2)_4C(O)$ | D-Tyr | 1 | Trp | Thr | azaGly | Leu | Me | Phe |
| P5 | $N_3$—$(CH_2CH_2O)_4$—$CH_2C(O)$ | D-Tyr | 1 | Trp | Thr | azaGly | Leu | Me | Phe |
| P6 | $N_3$—$(CH_2CH_2O)_4$—$CH_2CH_2C(O)$ | D-Tyr | 1 | Trp | Thr | azaGly | Leu | Me | Phe |
| P7 | $N_3(CH_2)_{10}C(O)$ | D-Tyr | 1 | Trp | Thr | Gly | Leu | Me | Phe |
| P8 | $N_3(CH_2)_4C(O)$ | D-Tyr | 1 | Trp | Thr | Gly | Leu | Me | Phe |
| P9 | $N_3$—$(CH_2CH_2O)_4$—$CH_2CH_2C(O)$ | D-Tyr | 1 | Trp | Thr | Gly | Leu | Me | Phe |
| P10 | $N_3(CH_2)_4C(O)$ | D-Tyr | 1 | Trp | Thr | Gly | Leu | H | Trp |
| P11 | $N_3(CH_2)_4C(O)$ | D-Tyr | 1 | Trp | Thr | [triazole-linked structure] | | Me | Phe |
| P12 | $N_3$—$(CH_2CH_2O)_4$—$CH_2CH_2C(O)$ | D-Tyr | 1 | Trp | Thr | [triazole-linked structure] | | Me | Phe |
| P13 | $N_3(CH_2)_4C(O)$ | D-Tyr | 1 | Trp | Thr | azaGly | Leu | Me | Trp |
| P14 | $N_3(CH_2)_4C(O)$ | Tyr | 1 | Trp | Thr | azaGly | Leu | Me | Phe |
| P15 | $N_3$—$(CH_2CH_2O)_4$—$CH_2C(O)$ | Tyr | 1 | Trp | Thr | azaGly | Leu | Me | Phe |
| P16 | $N_3(CH_2)_4C(O)$ | Tyr | 1 | Trp | Aib | [triazole-linked structure] | | Me | Trp |
| P17 | $N_3$—$(CH_2CH_2O)_4$—$CH_2CH_2C(O)$ | Tyr | 1 | Hyp | Thr | Gly | Leu | Me | Phe |
| P18 | H | Tyr | 1 | azido-lysine | Thr | Gly | Leu | Me | Phe |
| P19 | H | Tyr | 1 | $N^\epsilon[N_3(CH_2CH_2O)_4$—$CH_2CH_2C(O)]Lys$ | Thr | Gly | Leu | Me | Phe |
| P20 | $N_3(CH_2)_4C(O)$ | Tyr | 1 | Phe | Thr | Gly | Leu | Me | Phe |
| P21 | $N_3(CH_2)_4C(O)$ | Tyr | 1 | Trp | Ser | Gly | Leu | H | Phe |
| P22 | $N_3(CH_2)_4C(O)$ | D-Tyr | 0 | Hyp | Thr | azaGly | Leu | Me | Trp |
| P23 | $N_3$—$(CH_2CH_2O)_4$—$CH_2CH_2C(O)$ | D-Tyr | 0 | Hyp | Thr | azaGly | Leu | Me | Trp |
| P24 | $N_3(CH_2)_4C(O)$ | D-Tyr | 0 | Hyp | Thr | azaGly | Leu | H | Trp |
| P25 | $N_3(CH_2)_4C(O)$ | D-Tyr | 0 | Hyp | Thr | Gly | Leu | H | Trp |
| P26 | $N_3$—$(CH_2CH_2O)_4$—$CH_2CH_2C(O)$ | Tyr | 0 | Hyp | Thr | azaGly | Leu | H | Trp |
| P27 | $N_3$—$(CH_2CH_2O)_4$—$CH_2CH_2C(O)$ | D-Tyr | 0 | Hyp | Thr | [triazole-linked structure] | | Me | Trp |
| P28 = Kisspeptin10 | H | Tyr | 1 | Trp | Ser | Gly-leu | | H | Phe |
| P29 = | H | D-Tyr | 1 | Trp | Thr | azaGly-Leu | | Me | Phe |

TABLE A-continued

Kisspeptides analogues: $P_1$—M—$Z_1$-(Asn)$_n$-$Z_3$-Asn-$Z_5$-Phe-$Z_7$—$Z_8$-Arg($R_3$)—$Z_{10}$—$NH_2$ Formula (IV)

| Peptide | $P_1$—M | $Z_1$ | n | $Z_3$ | $Z_5$ | $Z_7$ | $Z_8$ | $R_3$ | $Z_{10}$ |
|---|---|---|---|---|---|---|---|---|---|
| reference peptide | | Tyr | | | | | | | |

Representative Example P4

Modified kisspeptide analogue P4 was manufactured by solid phase peptide synthesis (SPPS) using the Fmoc (9-fluorenylmethyloxycarbonyl) strategy. All the deprotections were made with piperidine 35% in DMF. The C-terminal phenyl residue is coupled to the resin (p-methylbenzhydrylamine polystyrene-1% divinylbenzene) via a Rink amide linker. The other amino acid residues are incorporated by a succession of Fmoc deprotection and amino acid coupling cycles. The summary of coupling amino acids on a resin (coupling method, excess and the time of coupling) is described in table B below:

TABLE B

| Coupling step | Amino Acid Derivative | Coupling Method | Excess (equiv.) | Coupling time |
|---|---|---|---|---|
| 1 | Fmoc-Phe-OH | DIC/HOBT in DMF | 2.0 | 3 h |
| 2 | Fmoc-Arg(Me)Pbf-OH | DIC/HOBT in DMF | 1.25 | overnight |
| 3 | Fmoc-Leu-OH | DIC/HOBT in DMF | 2.0 | 3 h |
| 4 | Fmoc-NHNHCO$_2$Np | DIPEA in DMF/DCM | 3.0 | overnight |
| 5 | Fmoc-Phe-OH | PyBOP/HOBt/DIEA in DMF | 3.0 | 2 h |
| 6 | Fmoc-Thr(tBu)-OH | DIC/HOBT in DMF | 2.0 | overnight |
| 7 | Fmoc-Asn(Trt)-OH | DIC/HOBT in DMF | 2.0 | 2 h 30 |
| 8 | Fmoc-Trp(Boc)-OH | DIC/HOBT in DMF | 2.0 | overnight |
| 9 | Fmoc-Asn(Trt)-OH | DIC/HOBT in DMF | 2.0 | overnight |
| 10 | Fmoc-D-Tyr(tBu)-OH | DIC/HOBT in DMF | 2.0 | overnight |
| 11 | 1-azido-pentanoic acid | DIC/HOBT in DMF | 2.0 | 2 h |

After solid phase assembly, cleavage from the resin and concomitant side chain deprotection with a mixture of TFA/H$_2$O/thioanisole (90/5/5) during 2 h30 hours at room temperature yields directly to the crude peptide with the C-terminal amide. After concentration of ~⅓ of the volume of the crude product mixture, the crude product is precipitated in cold MTBE. The precipitated peptide is filtered, washed with MTBE and dried under vacuum. The use of TFA/H$_2$O/thioanisole gave the best results to reduce of the formation of peptide-Rink Linker and suppresses the conversion of the azide into an amino group. Purification is performed by preparative reverse phase HPLC in TFA buffer. The eluting fractions are analyzed. The pure fractions are pooled daily before lyophilisation. Each lot of purified peptide thus obtained is tested by HPLC against the specification before entering the final lot. The selected pools are mixed together to form a homogeneous solution in water before freeze drying. Optional ion exchange into an acetate salt is performed on a Dowex resin after which the final solution is freeze dried and packaged. Purification is performed by a preparative reverse phase HPLC. 1 g of crude peptide was injected per run (dissolved in 100 mL of AcOH/H$_2$O/ACN 10/60/30). After filtration this mixture was loaded on the column. Buffer A=0.1% of TFA in water. Buffer B=ACN/buffer A (60/40 v/v). Stationary phase: C18 120 Å 15 µm. Column: 200×50 mm. Flow rate: 100 mL/min. UV detection: 210 nm. Linear gradient from 40 to 65% B in 30 min. The fractions are classified into waste, semi pure or pure fractions (waste: <70%, pure: >97%, front and back impure: 70% to <97%). Front and back impurities were collected and repurified with the same strategy.

Purity Analysis:

Equipment: Kontron software KS2000, column: Waters Symmetry C18, 250×4.6 mm, 5 µm, 100 Å. Flow rate: 1 ml/min, Temperature: 60° C., Wavelength: 210 nm Eluants: A: 0.1% TFA in MilliQ water (1 ml trifluoracetic acid in 1 l of water); B: 0.1% TFA in acetonitrile (1 ml trifluoracetic acid in 1 l of acetonitrile); Gradient: 20-80% in 30 min. Injection volume: 20 µl of a solution at 0.5 mg/ml in 30% of acetonitrile.

Amino Acid Analysis:

Protocol: the peptide is first converted into its constituent amino acids by hydrolysis in constant boiling propionic acid, at 110° C., for 20 hours. Determination of amino acids, based on reversed-phase HPLC, is then performed according to the precolumn method derivatization with OPA reagent for primary amines and Fmoc-Cl reagent for secondary amines with UV detection at 338 nm and 262 nm. Results were in agreement with the proposed amino acid composition.

Conjugation Methods

Method A: Thiol-Bromide Coupling

Pentasaccharide 5 or 8 was dissolved in DMF (10 mg/mL) and hydroxylamine was added (25 equiv.). The solution was stirred for 10 minutes and was subsequently added to a solution of peptide P1 in DMF (3 mg/mL). EDTA, disodium salt (5 equiv.) was added and the mixture was stirred overnight at room temperature under a nitrogen atmosphere. The solution was diluted with water (3×) and purified by ion exchange chromatography on a Q Sepharose (Q FF HiTrap™ 5 mL) column). Fractions were analyzed with MonoQ ion exchange chromatography. Appropriate fractions containing conjugated kisspeptide were collected and purified by hydrophobic interaction chromatography (HIC Phenyl FF HiTrap™ high sub 5 mL column) using 3M NaCl as eluent. The combined fractions containing the conjugate were desalted by gel filtration chromatography on a G-25 sephadex column using water. Appropriate fractions were collected, filtered over a sterile 0.22 µm filter and lyophilized to yield the conjugate as a white solid.

Method B: Squarate Coupling

Boric acid (3.09 g), KCl (2.61 g) and KOH (0.84 g) were dissolved in 100 mL water and the pH was adjusted to 9.0 by addition of solid KOH. Subsequently, peptide P2 or P3 was dissolved in a 1:1 mixture of MeOH and the aforementioned borate buffer (5 mg/mL). Next, pentasaccharide 3 or 4 (1.5 equiv.) was added as a solution water (30 mg/mL). After 1 hour solids started to appear in the reaction mixture and ACN was added until a clear solution was obtained. After overnight stirring the organic solvents were removed by evaporation under vacuum and water was added.

Purification of the conjugate was performed as described in Method A.

Method C: Coupling by a Cycloaddition Reaction

Compound P4 (0.50 g, 0.33 mmol) was dissolved in DMF (20 mL). NMM (0.054 mL, 0.494 mmol, 1.5 eq) was added under a nitrogen atmosphere, followed by a solution of pentasaccharide 7 (0.65 g, 0.33 mmol) in water (10 mL). Nitrogen was bubbled through the solution for 5 min. Then sodium ascorbate (32.7 mg, 0.165 mmol, 0.5 equiv.) was added, followed by TBTA (17.5 mg, 0.165 mmol, 0.5 eq) and copper sulfate (26.3 mg, 0.165 mmol, 0.5 eq). The solution was stirred 30 minutes at r.t. A solution of EDTA disodium salt (380 mg, 1.13 mmol) in water (10 mL) was added and stirred for 30 minutes before drop wise addition of ACN (200 mL). After stirring for 20 minutes the precipitate was filtered off and washed with ACN. The residue was dried for 30 minutes before flushed with water (200 mL) and captured in a clean flask. The solution was eluted on a RP18 lichroprep column (70 mL) followed by water (600 mL). Then the column was eluted with a mixture of ACN and water (1/9, 1800 mL) and captured in fraction of 20 mL. The fractions containing product were collected and lyophilized to yield compound C8 (608 mg, 0.178 mmol, 53.8%).

This method is also representative for conjugation of kisspeptide derivatives P5-P27 to pentasaccharides 6, 7, 9 and 10.

TABLE C

Kisspeptide-pentasaccharide conjugates: Conjugation methodology and analytical data

| Conjugate | Peptide | Penta-saccharide | Conjugation Method | Retention time Rt | Analytical Method |
|---|---|---|---|---|---|
| C1 | P1 | 5 | A | 18.4 | A |
| C2 | P1 | 8 | A | 10.1 | B |
| C3 | P2 | 4 | B | 8.4 | E |
| C4 | P2 | 2 | B | 7.8 | E |
| C5 | P3 | 2 | B | 10.2 | B |
| C6 | P4 | 10 | C | 8.4 | E |
| C7 | P4 | 6 | C | 13.9 | C |
| C8 | P4 | 7 | C | 14.6 | C |
| C9 | P5 | 7 | C | 8.9 | E |
| C10 | P6 | 6 | C | 19.9 | C |
| C11 | P6 | 7 | C | 16.7 | A |
| C12 | P7 | 6 | C | 21.2 | C |
| C13 | P7 | 7 | C | 21.1 | C |
| C14 | P8 | 7 | C | 14.5 | A |
| C15 | P9 | 7 | C | 17.6 | A |
| C16 | P9 | 6 | C | 18.0 | A |
| C17 | P10 | 7 | C | 15.2 | A |
| C18 | P11 | 6 | C | 17.6 | A |
| C19 | P12 | 6 | C | 18.7 | A |
| C20 | P12 | 7 | C | 18.5 | A |
| C21 | P13 | 7 | C | 14.8 | C |
| C22 | P14 | 7 | C | 14.9 | A |
| C23 | P15 | 7 | C | 8.7 | E |
| C24 | P16 | 7 | C | 18.4 | C |
| C25 | P17 | 6 | C | 11.7 | C |
| C26 | P17 | 7 | C | 11.5 | A |
| C27 | P18 | 7 | C | 11.0 | A |
| C28 | P19 | 7 | C | 12.1 | A |
| C29 | P20 | 7 | C | 16.1 | D |
| C30 | P22 | 6 | C | 14.5 | A |
| C31 | P22 | 7 | C | 11.9 | C |
| C32 | P23 | 9 | C | 12.9 | C |
| C33 | P23 | 10 | C | 12.8 | C |
| C34 | P23 | 6 | C | 12.4 | A |
| C35 | P23 | 7 | C | 12.2 | C |
| C36 | P24 | 6 | C | 11.2 | C |
| C37 | P24 | 7 | C | 11.5 | C |
| C38 | P25 | 6 | C | 15.8 | A |
| C39 | P25 | 7 | C | 15.6 | A |
| C40 | P26 | 6 | C | 14.9 | A |
| C41 | P27 | 6 | C | 13.2 | C |
| C42 | P21 | 7 | C | 9.9 | A |

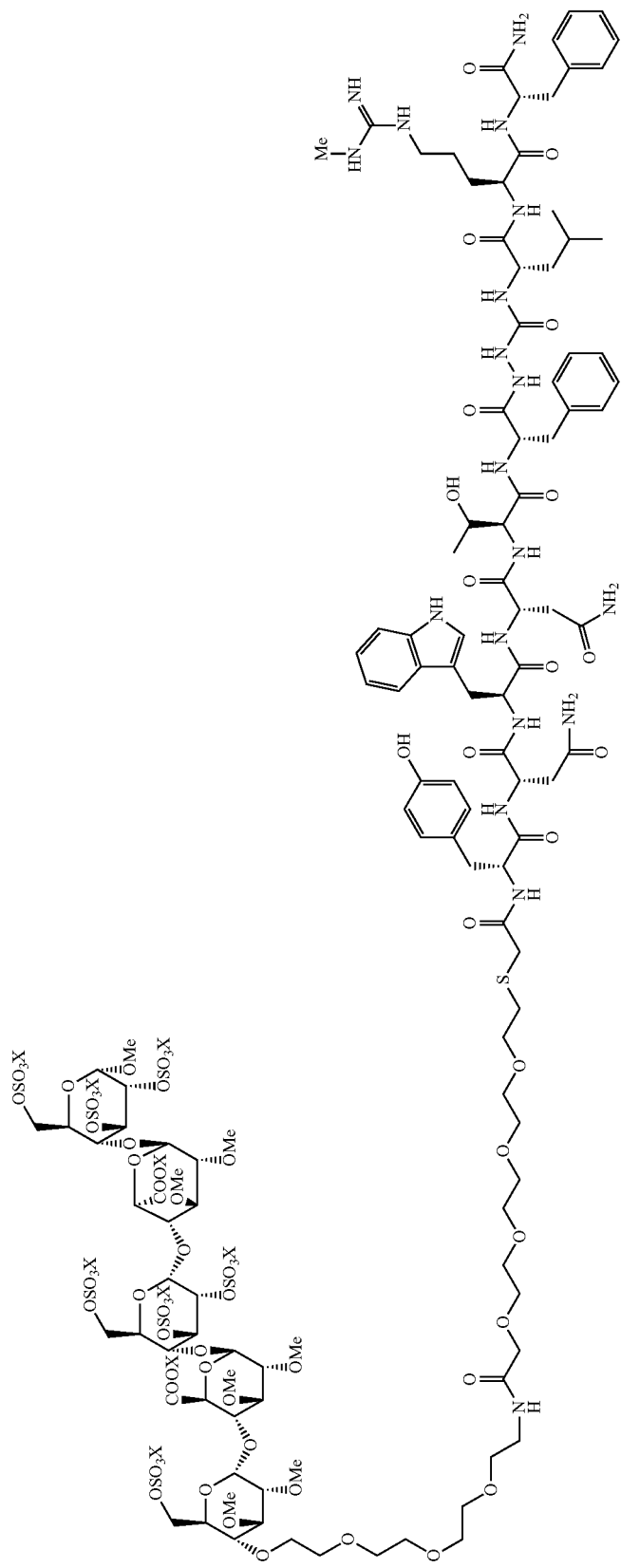

P1 (2.2 mg, 1.5 umol, 1 equiv.) was conjugated to pentasaccharide 5 (4.3 mg, 2.0 umol, 1.3 equiv.) according to method A. Yield: 1.1 mg (21%).
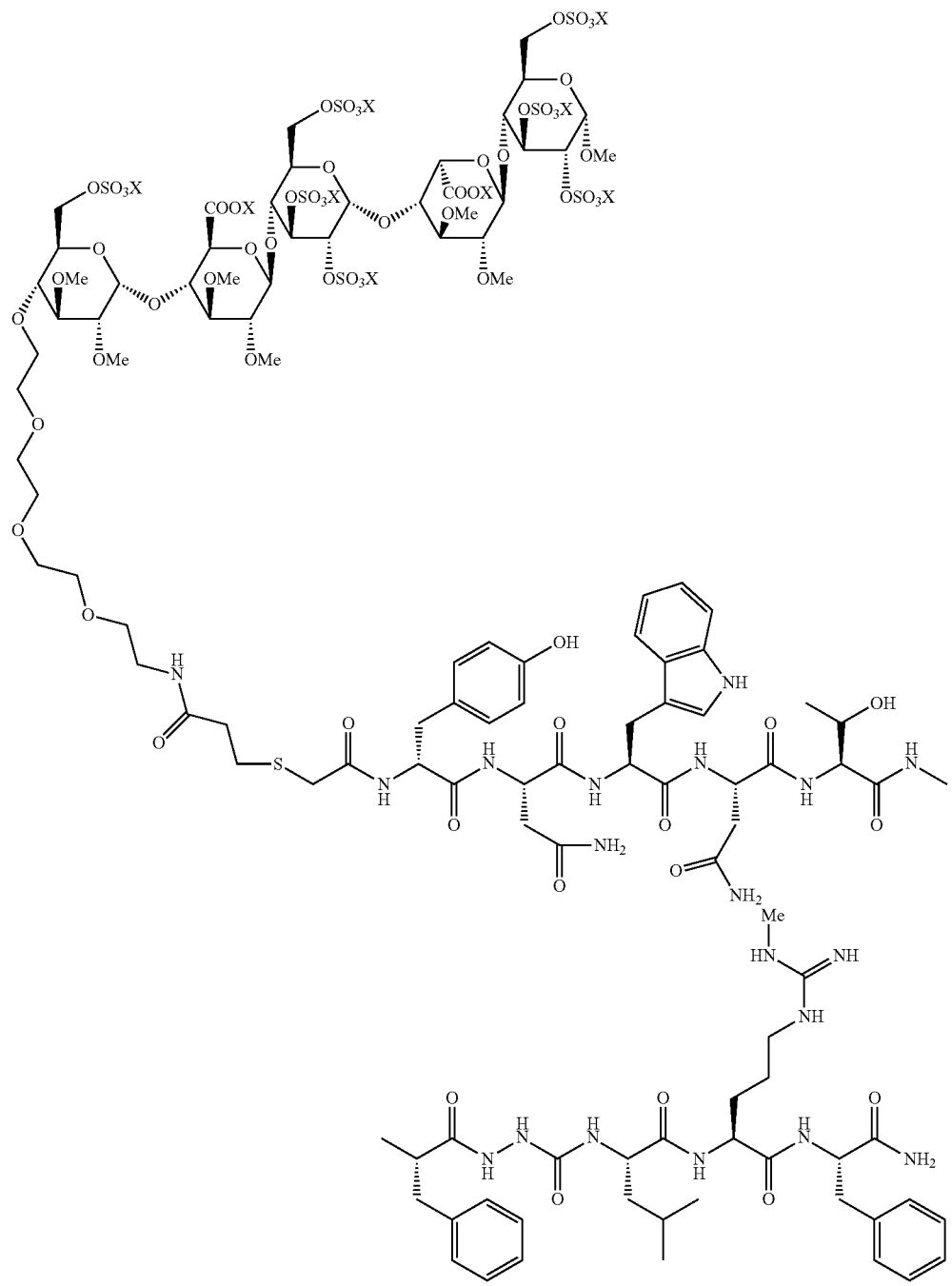
Conjugate C2
X = Na⁺
P1 (1.9 mg, 1.3 umol, 1 equiv.) was conjugated to pentasaccharide 8 (3.4 mg, 1.7 umol, 1.3 equiv.) according to method A. Yield: 0.5 mg (10%). Theoretical mass: 3348. MS results: MIM=3148 observed in the form of ammonium adducts for (M2+, M3+, M4+ and [M-SO3]$_n$*).

Conjugate C3
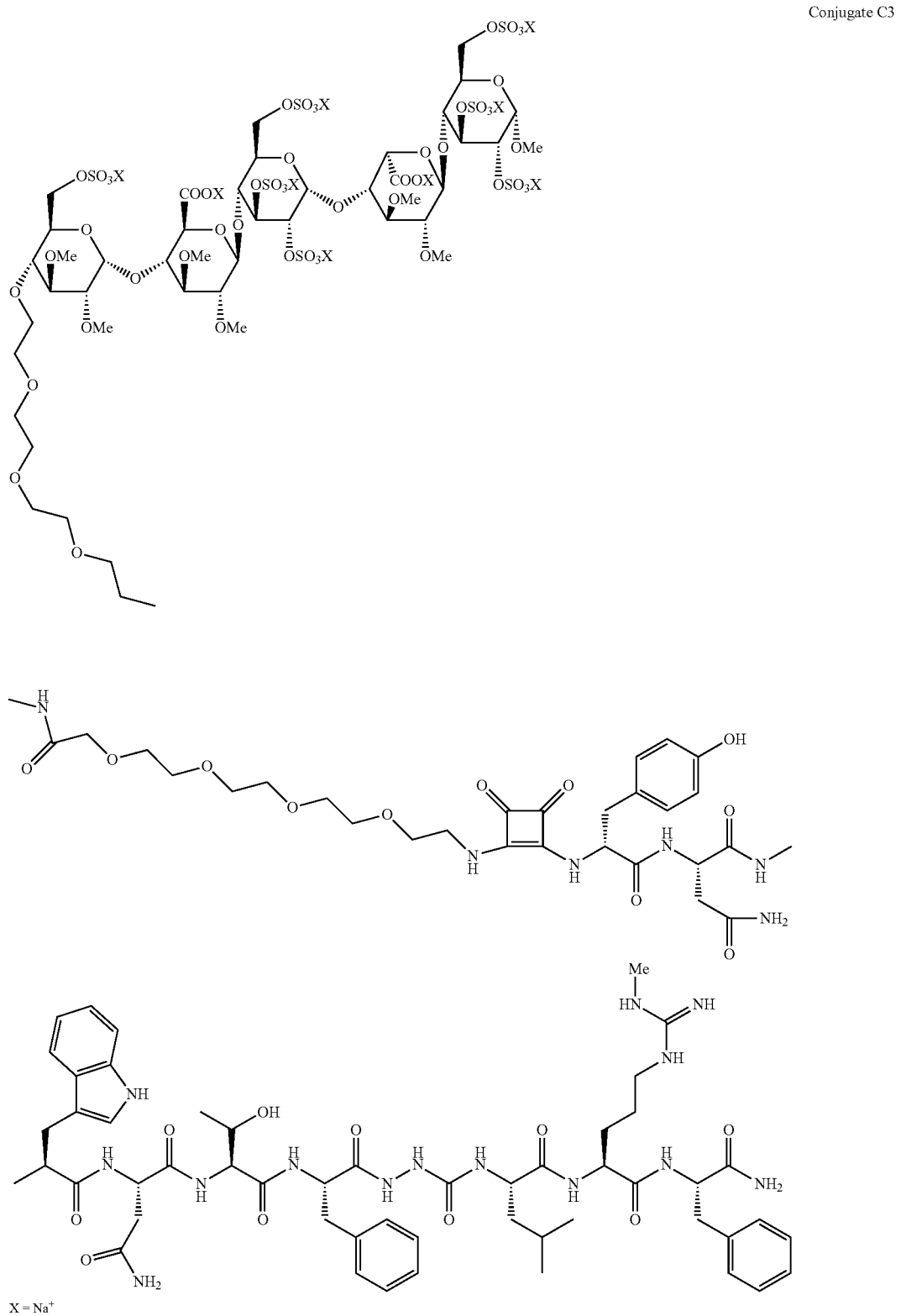
X = Na⁺
Peptide P2 (5.6 mg, 3.9 umol, 1 equiv.) was conjugated to pentasaccharide 4 (8.8 mg, 4.2 mmol, 1.06 equiv.) according to method B. Yield: 3.5 mg (26%). Theoretical mass: 3531. MS results: ammonium adducts of MIM 3330.9 (M-9 Na).

Conjugate C4
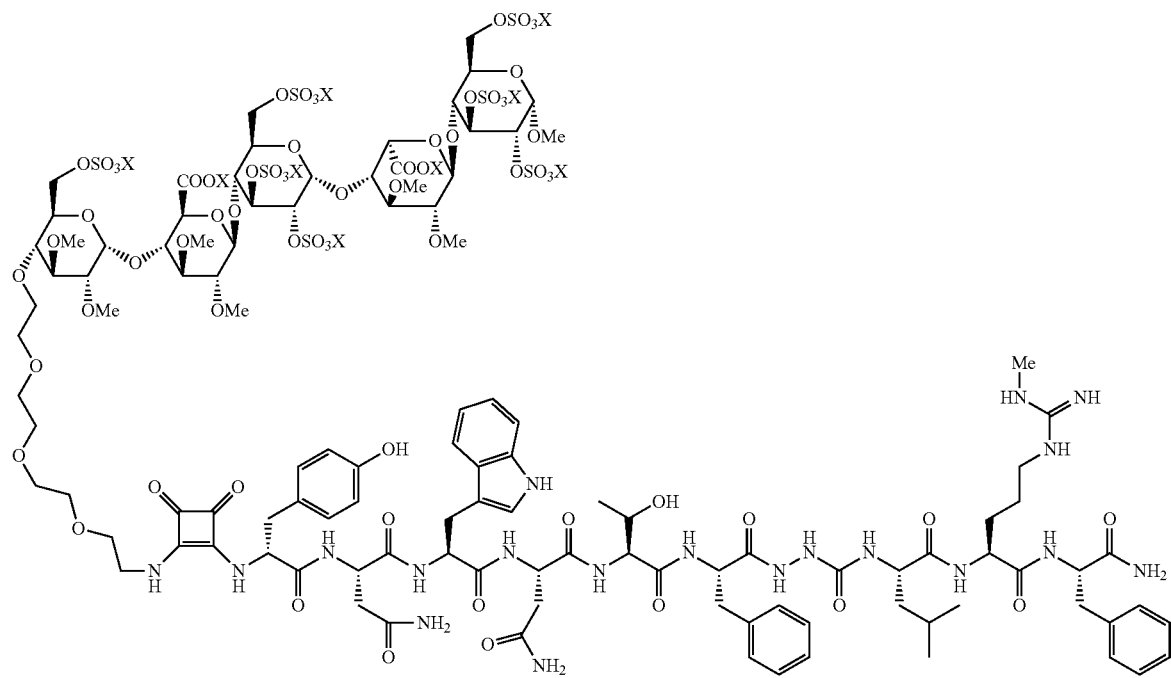
Peptide P2 (5.5 mg, 3.8 umol, 1 equiv.) was conjugated to pentasaccharide 2 (7.2 mg, 3.8 mmol, 1 equiv) according to method B. Yield: 1.5 mg (12%). Theoretical mass: 3298. MS results: ammonium adducts of MIM 3087(M-9 Na).

Conjugate C5
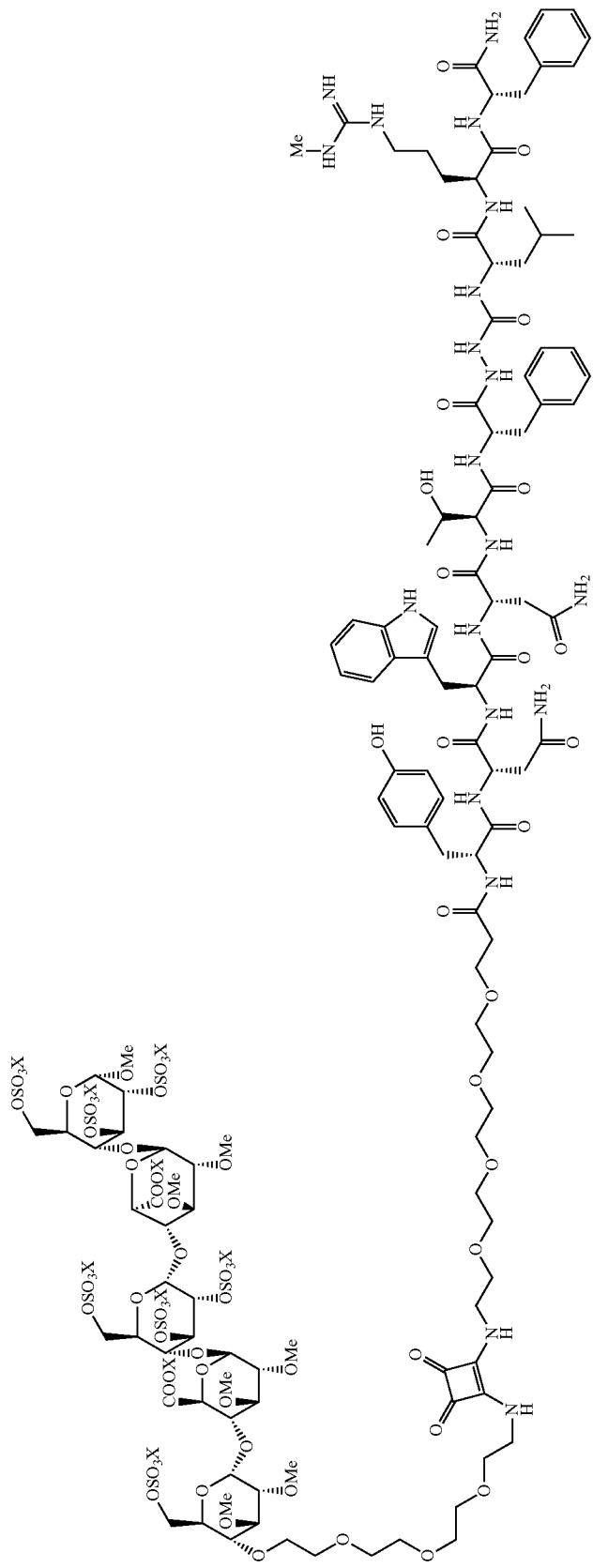
X = Na+

Peptide P3 (2 mg, 1.18 umol, 1 equiv.) was conjugated to pentasaccharide 2 (3 mg, 1.6 umol, 1.35 equiv.) according to method B. Yield: 1.7 mg (41%).
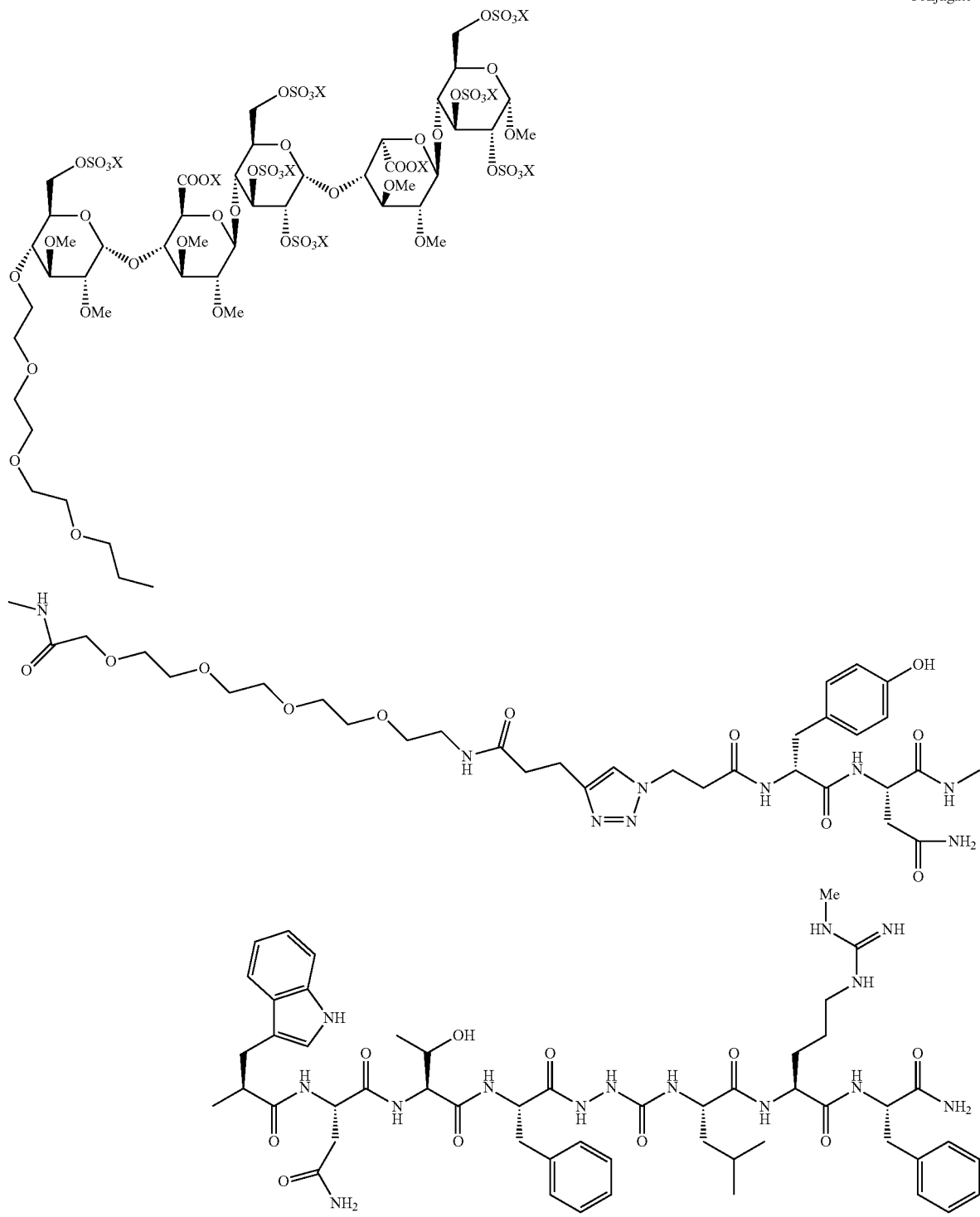
Conjugate C6
X = Na$^+$
Peptide P4 (3.2 mg, 2.2 mmol, 1 equiv.) was conjugated to pentasaccharide 10 (5.8 mg, 2.6 mmol, 1.2 equiv.) according to method C. Yield: 2 mg (26%). Theoretical mass: 3658. MS results: ammonium adducts of MIM 3458(M-9 Na).

Conjugate C7
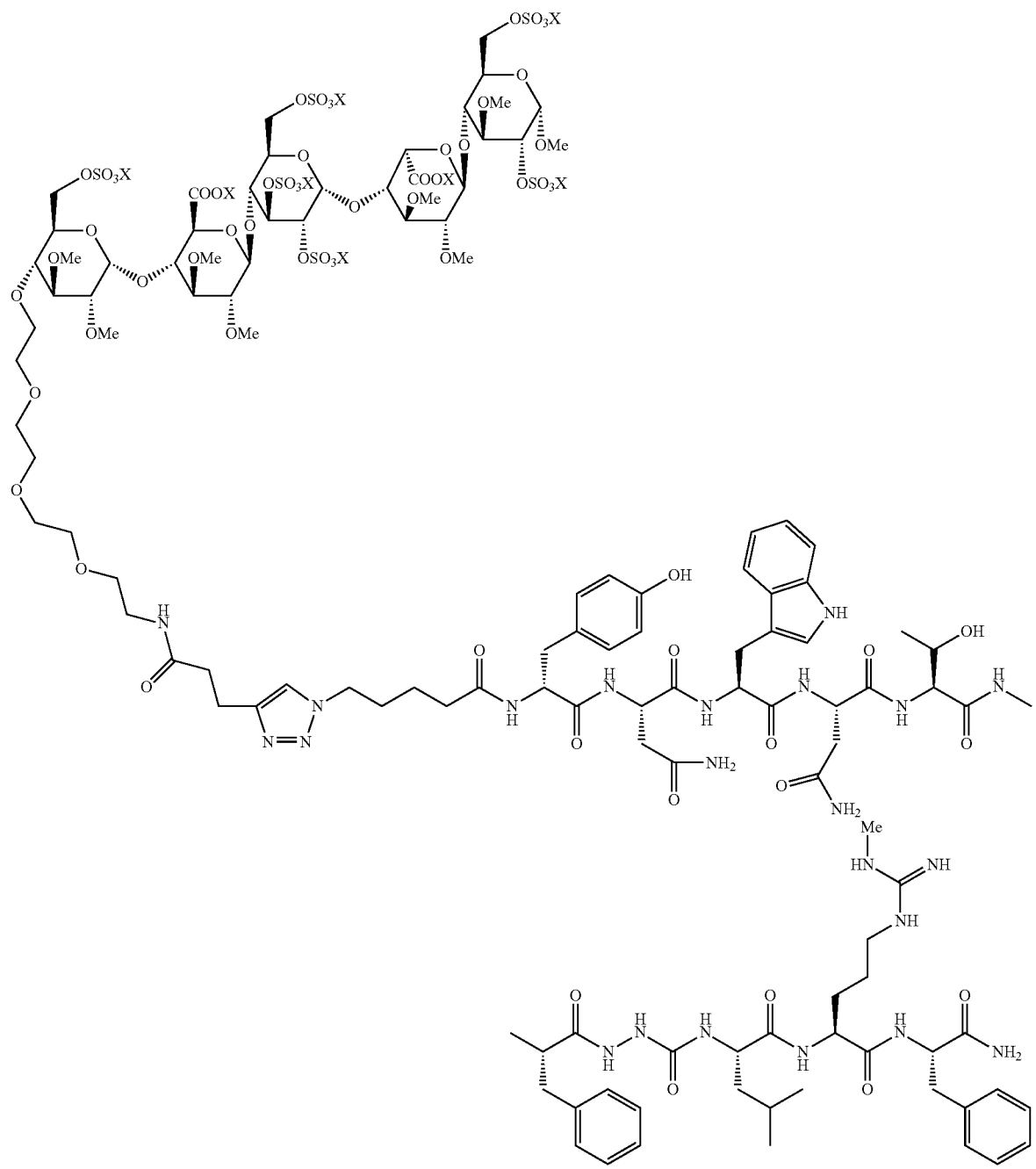
X = Na+
Peptide P4 (32 mg, 0.019 mmol, 1 equiv.) was conjugated to pentasaccharide 6 (77 mg, 0.041 mmol, 2 equiv.) according to method C. Yield: 15 mg (24%). Theoretical mass: 3337. MS results: ammonium adducts of MIM 3158.9 (M-8 Na)

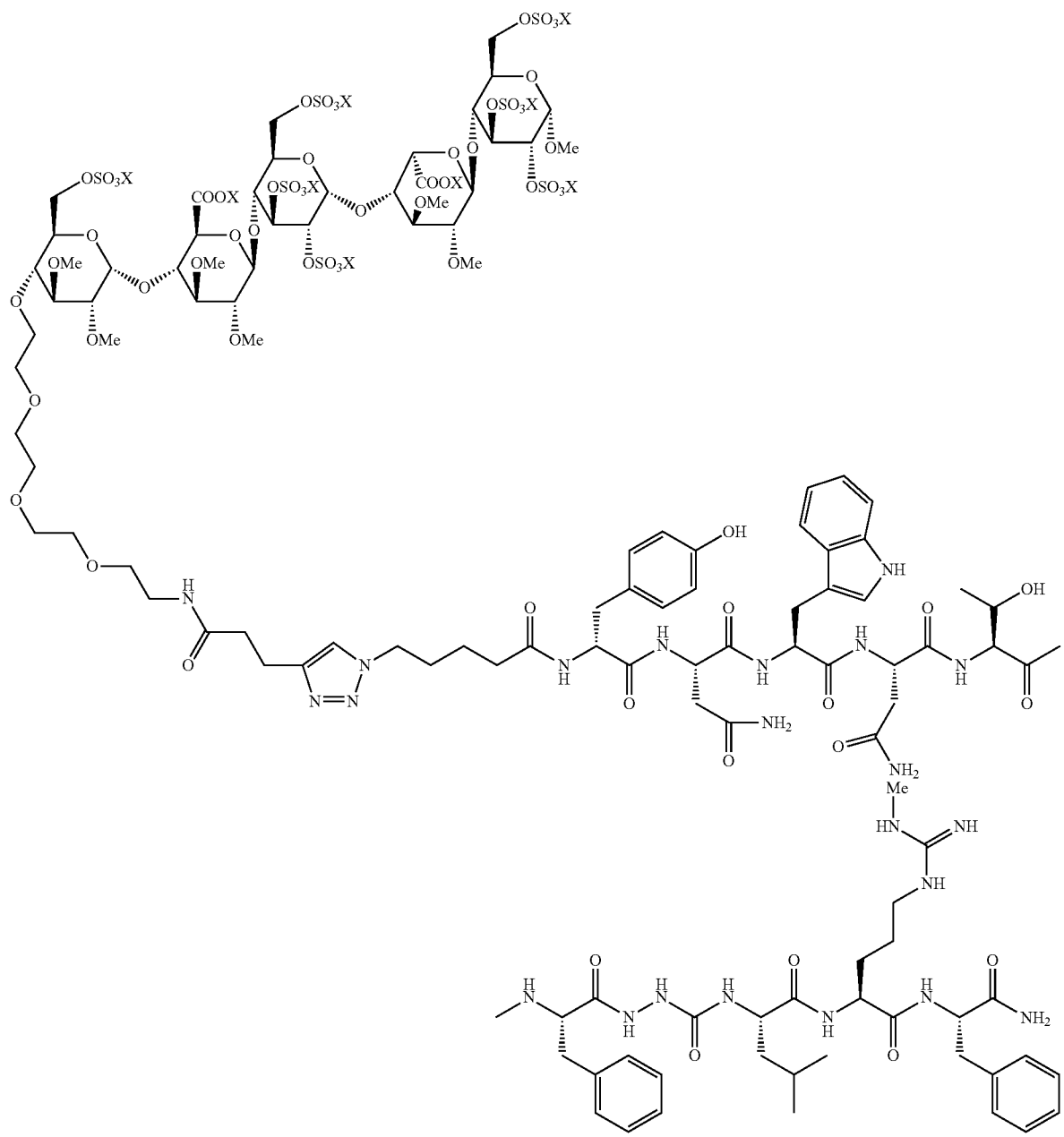
Conjugate C8
X = Na+
Peptide P4 (50 mg, 0.033 mmol, 1 equiv.) was conjugated to pentasaccharide 7 (65 mg, 0.033 mmol, 1.0 equiv.) according to method C. Yield: 61 mg (54%). Theoretical mass: 3224.8.

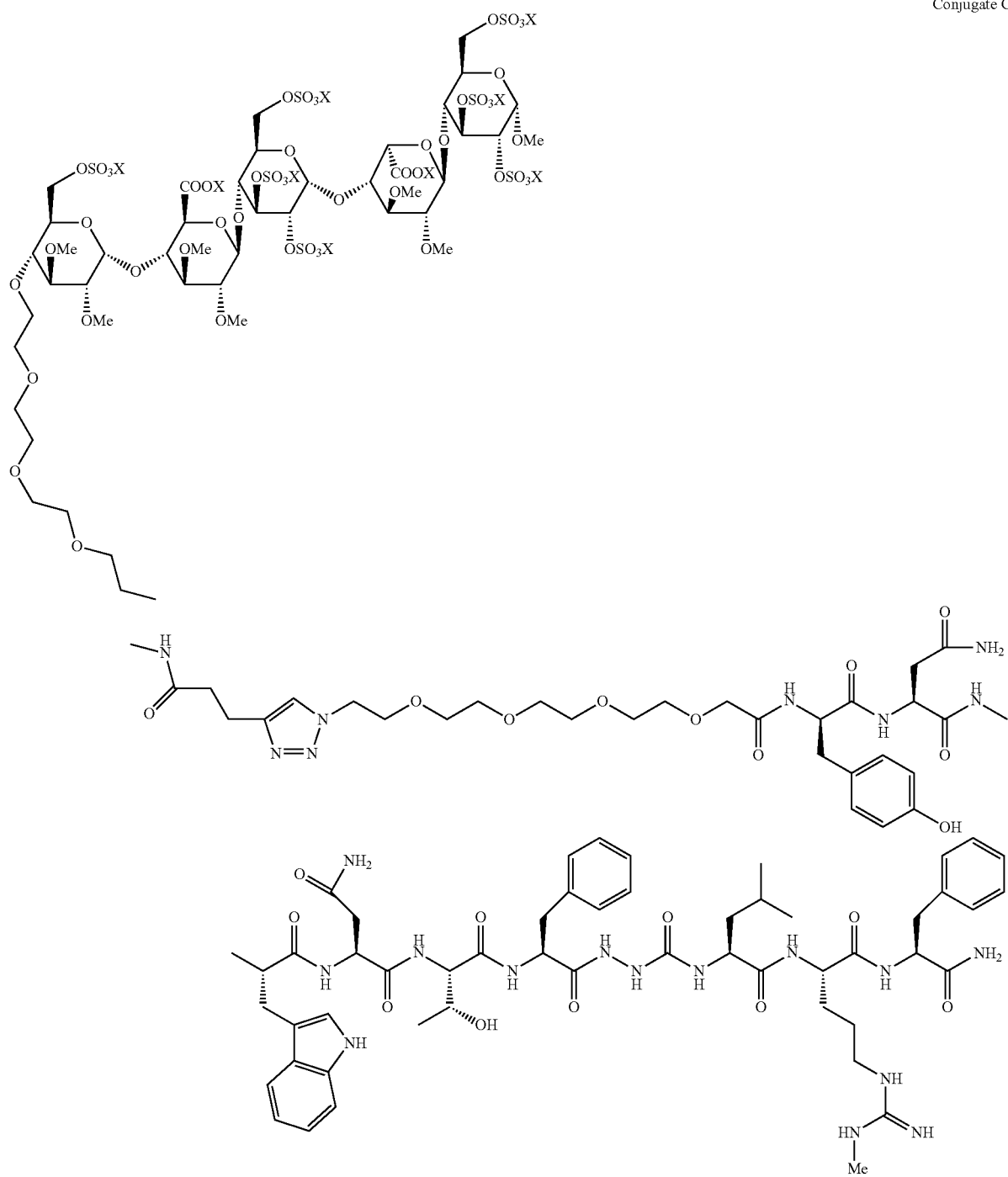
Conjugate C9
X = Na⁺
Peptide P5 (3.5 mg, 2.2 mmol, 1 equiv.) was conjugated to pentasaccharide 7 (5.8 mg, 2.6 mmol, 1.2 equiv.) according to method C. Yield: 1 mg (12%). Theoretical mass: 3792.5. MS results: ammonium adducts of MIM 3592(M-9 Na).

Conjugate C10
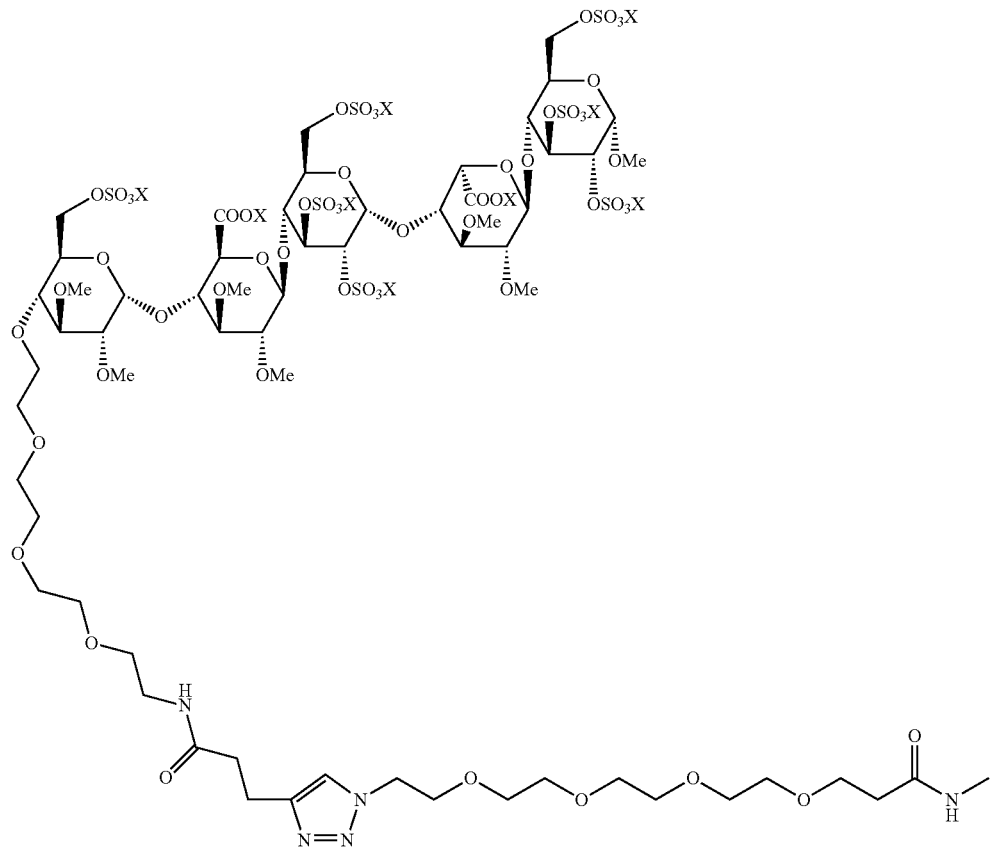
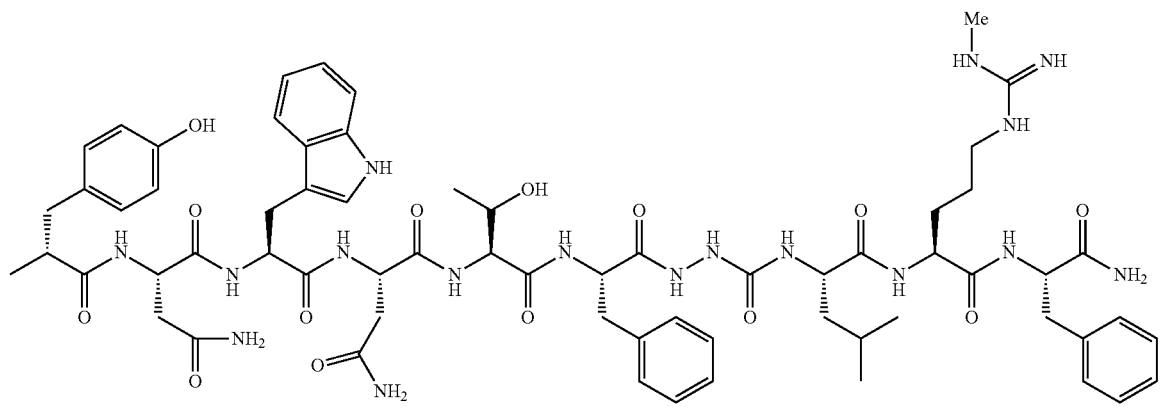
X = Na+
Peptide P6 (43.3 mg, 27 umol, 1 equiv.) was conjugated to pentasaccharide 6 (70.0 mg, 41 umol, 1.5 equiv) according to method C. Yield: 3.0 mg (10%). Theoretical mass: 3485. MS results: MIM 3307.

Conjugate C11
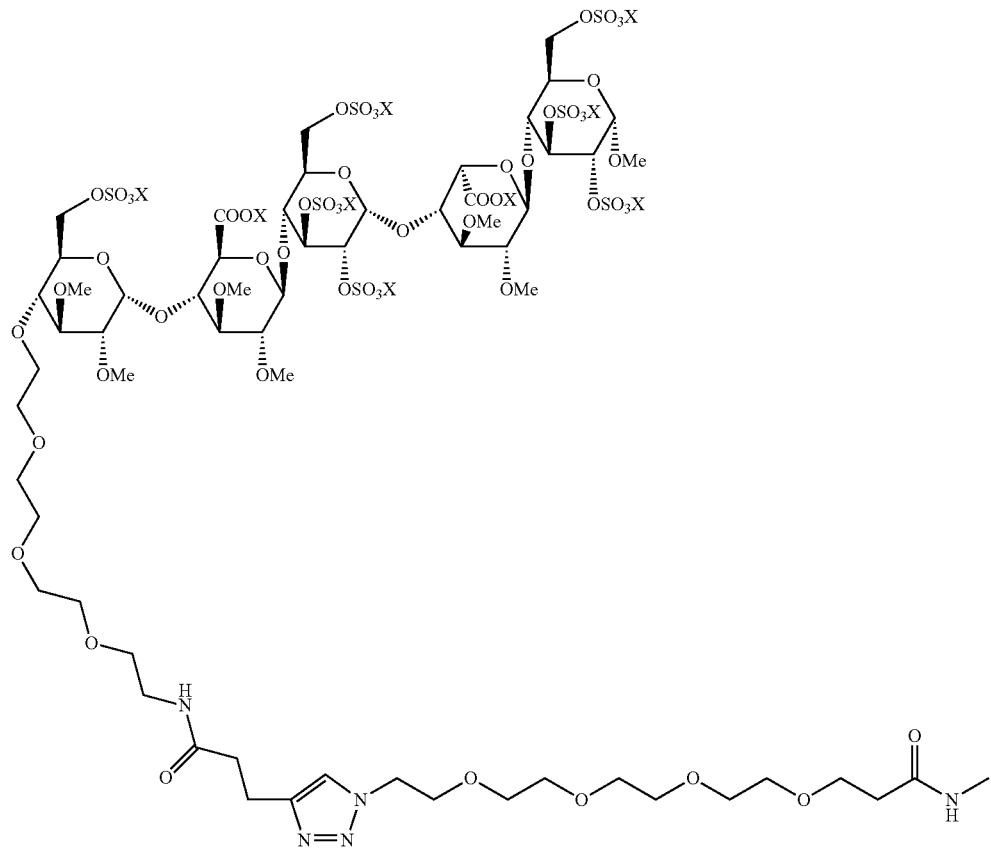
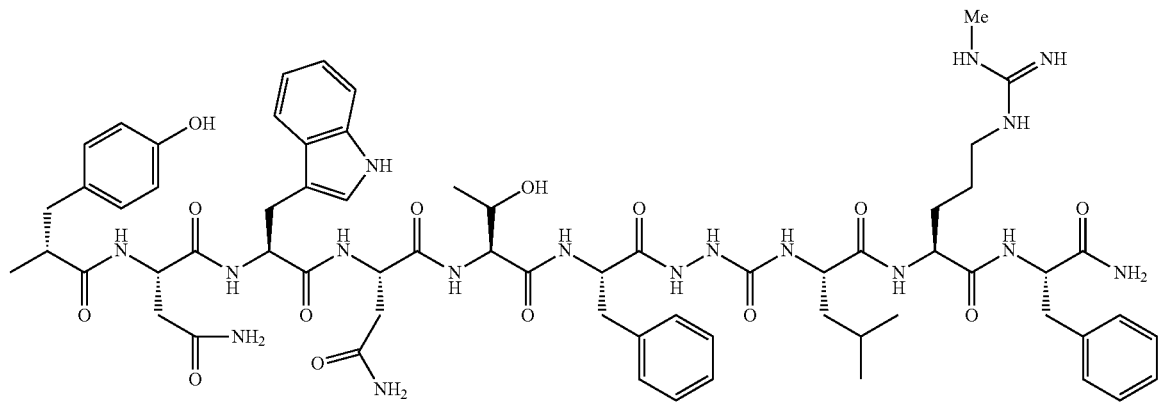
X = Na+
Peptide P6 (20.6 mg, 13 umol, 1 equiv.) was conjugated to pentasaccharide 7 (25.2 mg, 13 umol, 1.0 equiv.) according to method C. Yield: 24.1 mg (56%).

Conjugate C12
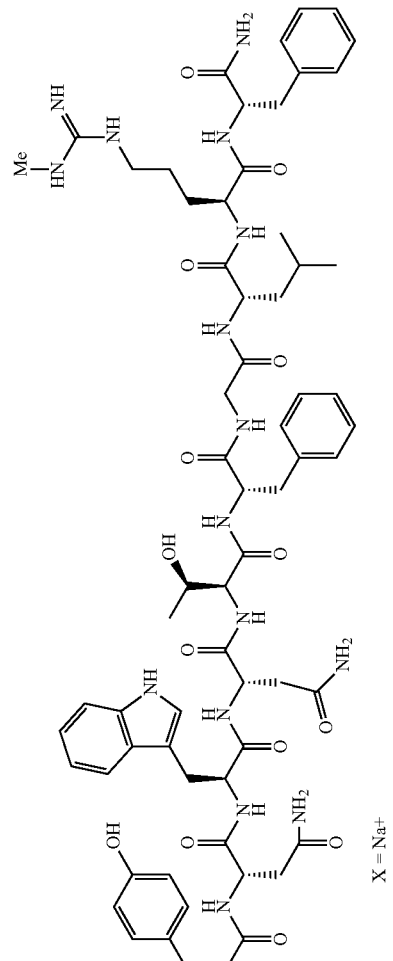
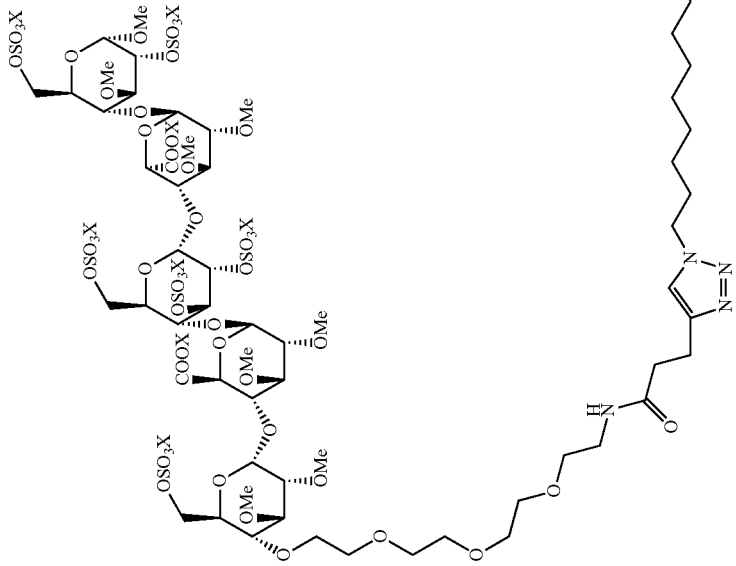
X = Na+

Peptide P7 (5.9 mg, 3.8 umol, 1 equiv.) was conjugated to pentasaccharide 6 (9.8 mg, 5.7 umol, 1.5 equiv.) according to method C. Yield: 5.4 mg (41%).

Conjugate C13
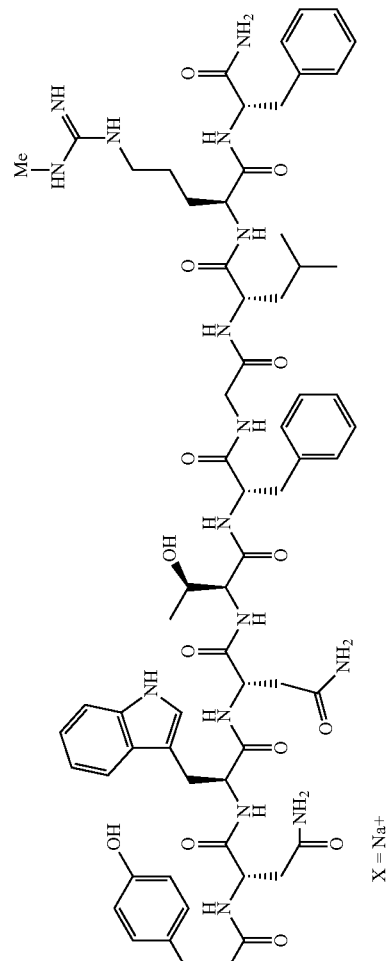
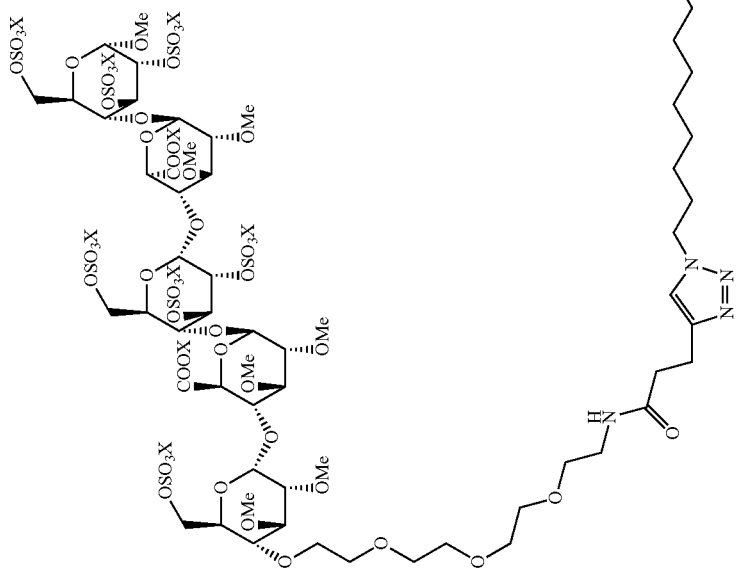
X = Na+

Peptide P7 (5.5 mg, 3.6 umol, 1 equiv.) was conjugated to pentasaccharide 7 (9.8 mg, 5.5 umol, 1.5 equiv.) according to method C. Yield: 3.5 mg (29%).

Conjugate C14
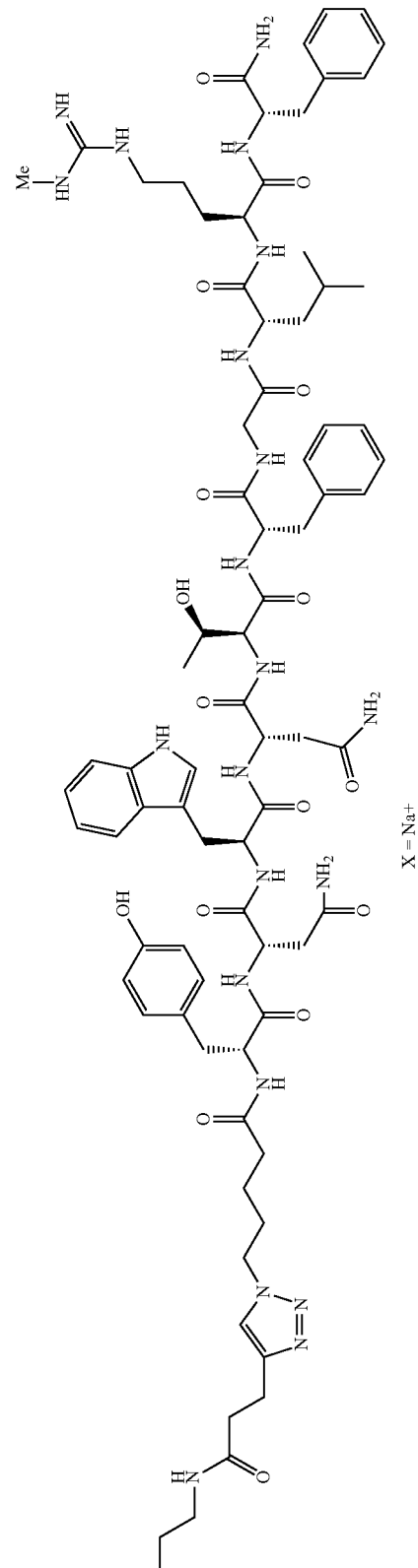
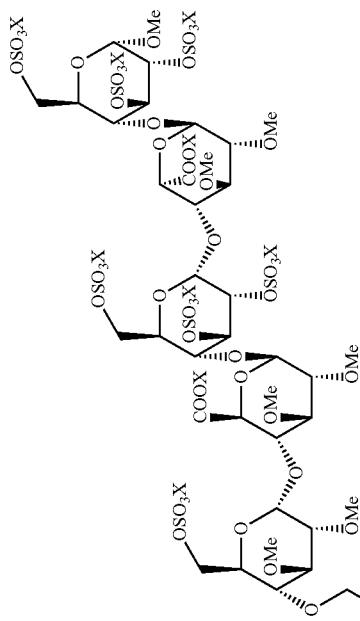
X = Na+

Peptide P8 (17.7 mg, 0.012 mmol, 1 equiv.) was conjugated to pentasaccharide 7 (32.2 mg, 0.018 mmol, 1.5 equiv.) according to method C. Yield: 11.9 mg (29%). MS results: MIM=3223.8.

Conjugate C15
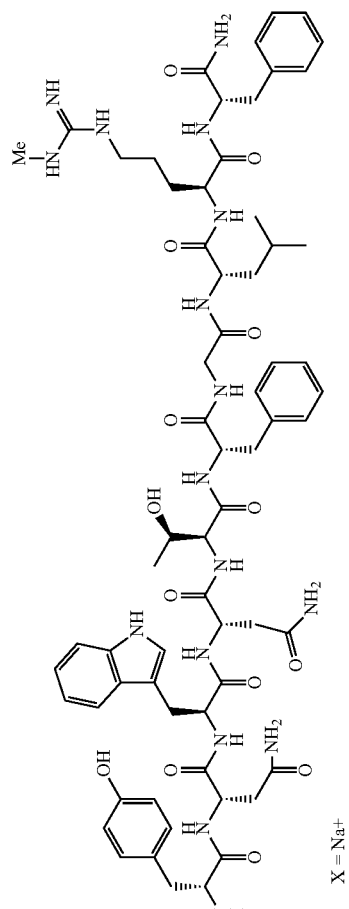
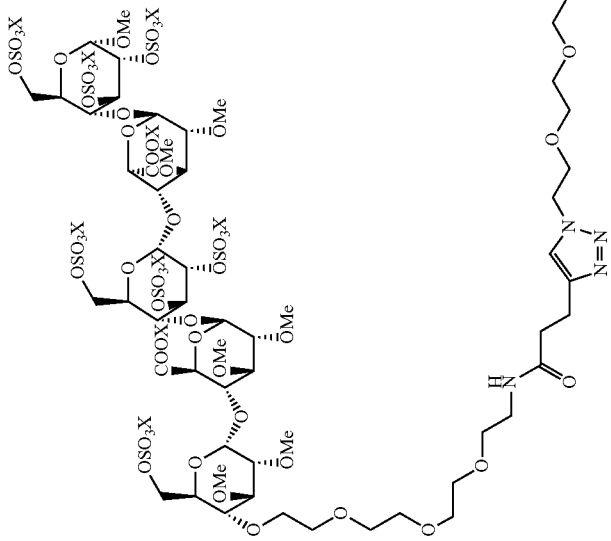
X = Na+

Peptide P9 (8.75 mg, 5.5 umol, 1 equiv.) was conjugated to pentasaccharide 7 (11.3 mg, 5.7 umol, 1.05 equiv.) according to method C. Yield: 3.3 mg (18%).

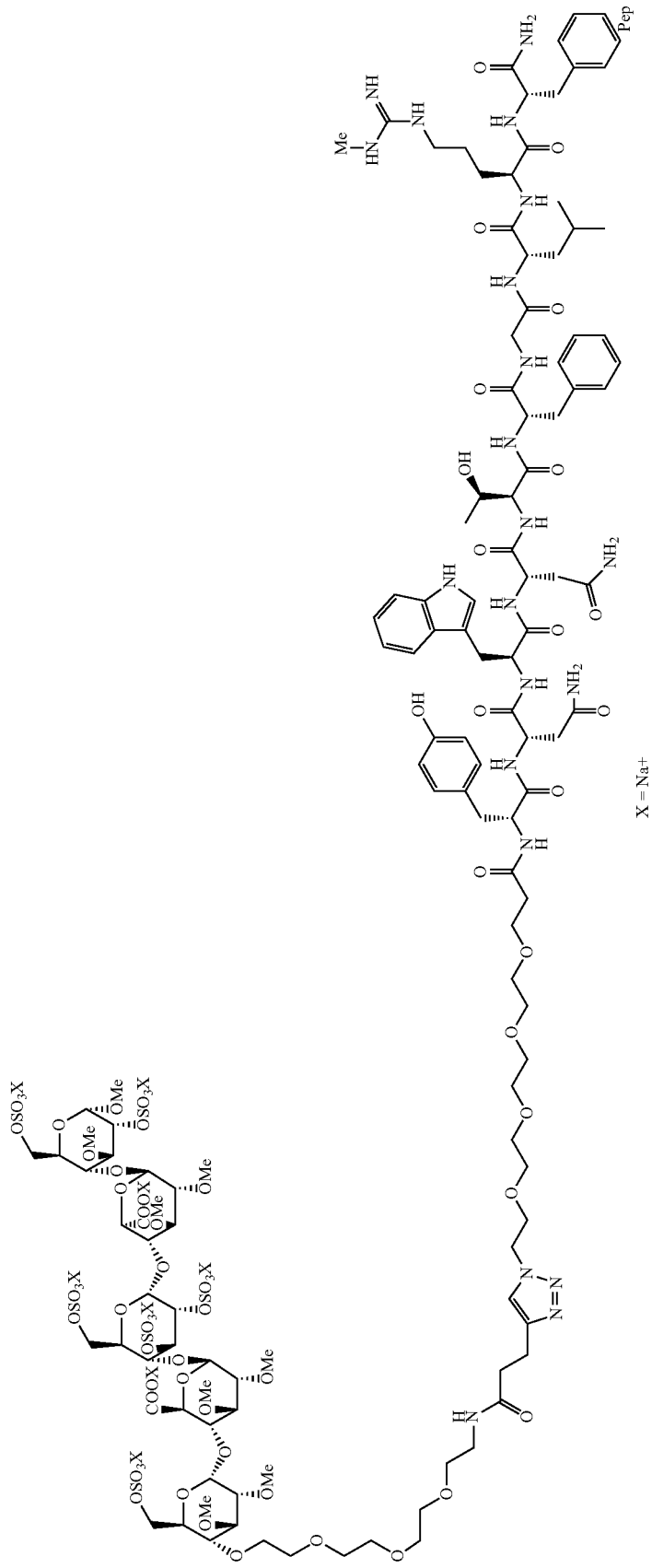

Peptide P9 (8.75 mg, 5.5 umol, 1 equiv.) was conjugated to pentasaccharide 6 (10.8 mg, 5.7 umol, 1.05 equiv.) according to method C. Yield: 2.9 mg (16%).

Conjugate C17
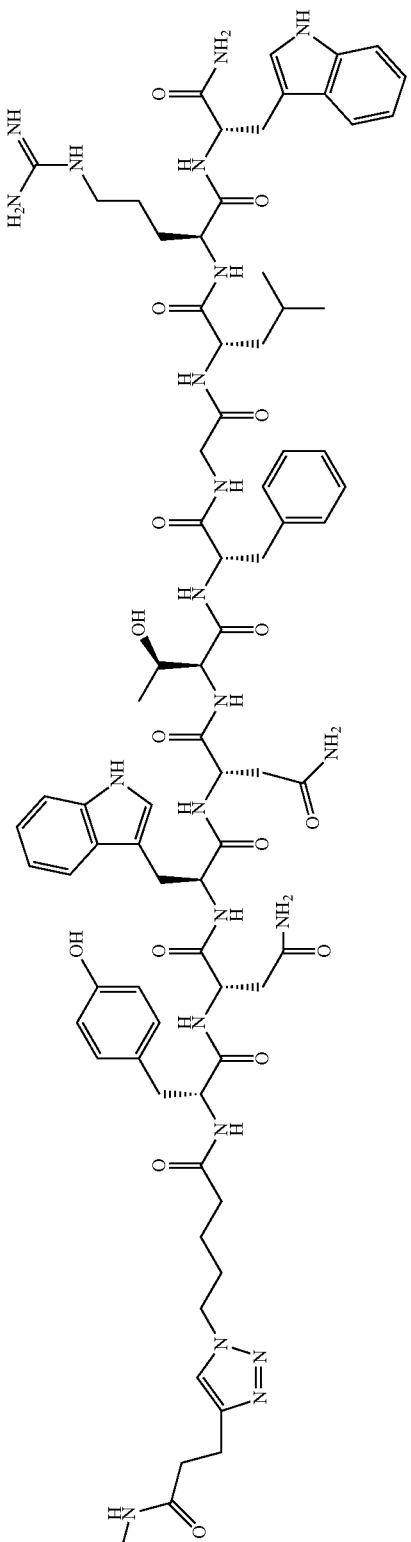
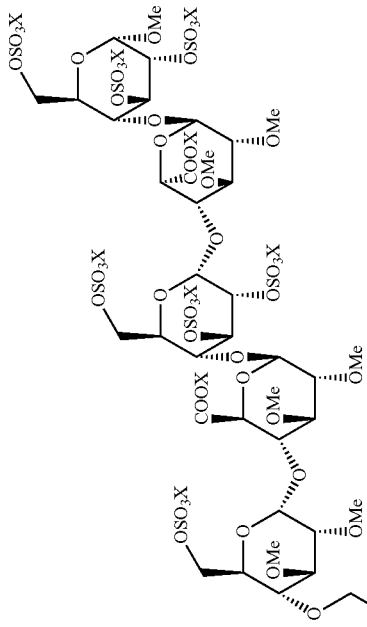
X = Na+

Peptide P10 (5.6 mg, 3.8 umol, 1 equiv.) was conjugated to pentasaccharide 7 (11.2 mg, 5.7 umol, 1.5 equiv.) according to method C. Yield: 4.5 mg (35%). Theoretical mass: 3449. MS results: MIM=3248.8 observed in the form of ammonium adducts for (M2+, M3+, M4+ and [MSO3]n+). Accurate mass and isotope fit are in agreement with structural formula.

Conjugate C18
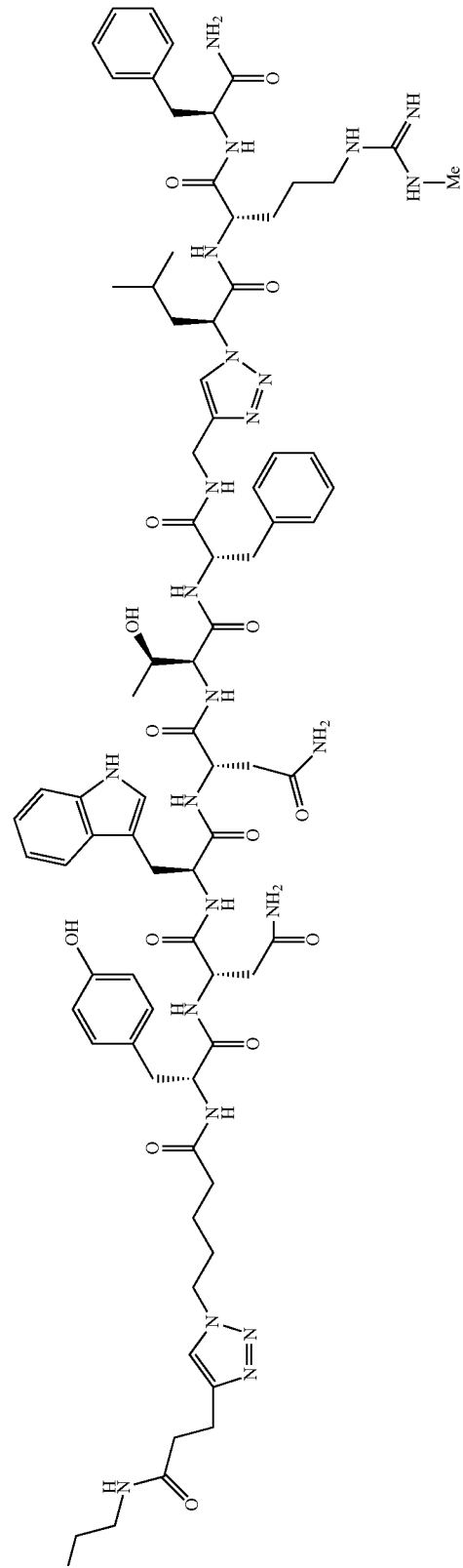
X = Na+
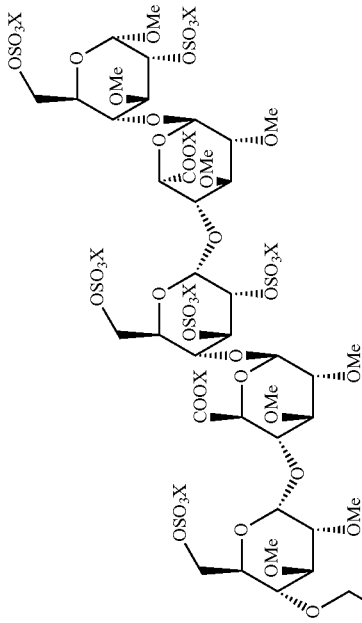

Peptide P11 (18.7 mg, 0.013 mmol, 1 equiv) was conjugated to pentasaccharide 6 (47.5 mg, 0.025 mmol, 2 equiv.) according to method C. Yield: 26 mg (61%). Theoretical mass: 3360. MS results: ammonium adducts of MIM 3181.98 (M-8Na).

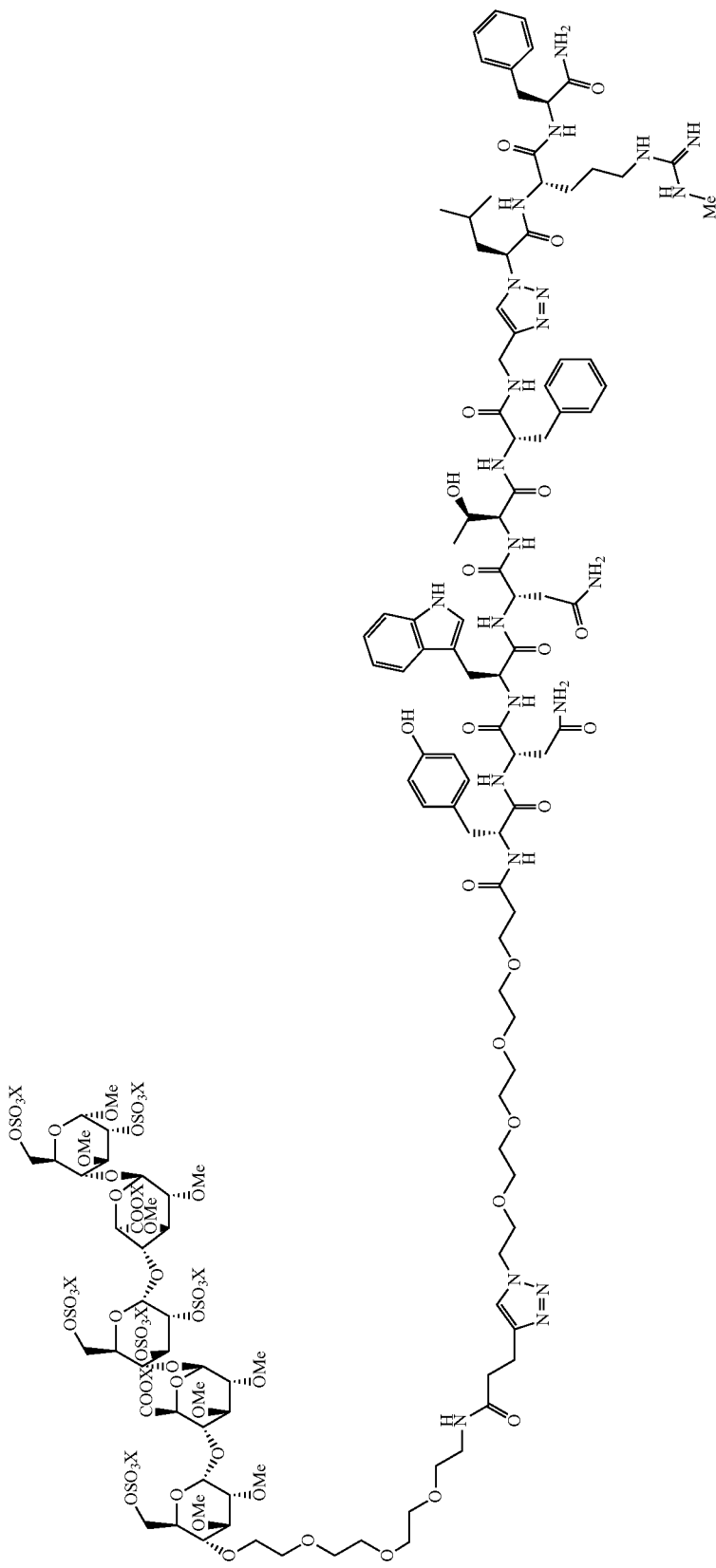

Peptide P12 (10 mg, 6.1 umol, 1 equiv.) was conjugated to pentasaccharide 6 (11.6 mg, 6.8 umol, 1.1 equiv.) according to method C. Yield: 3.04 mg (15%).

Conjugate C20
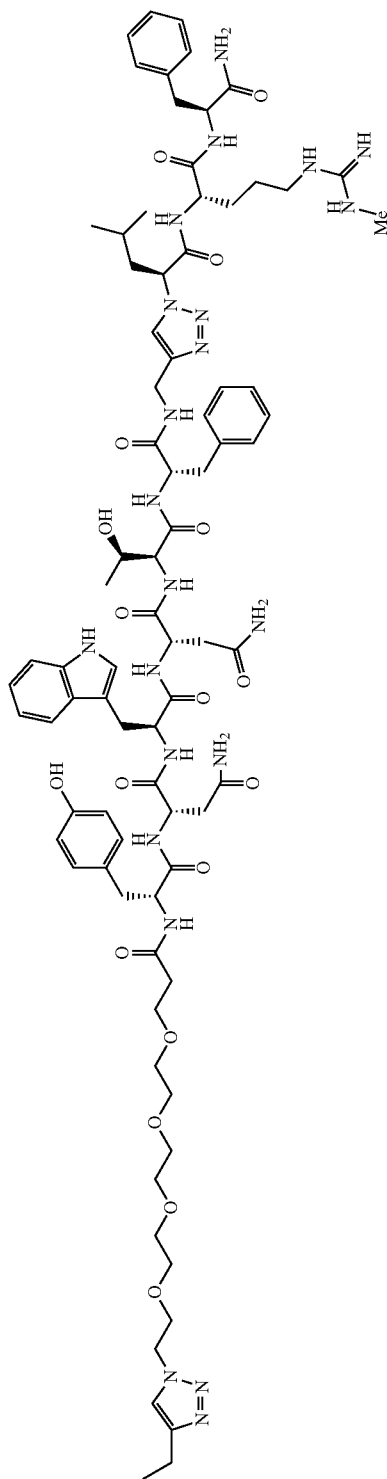
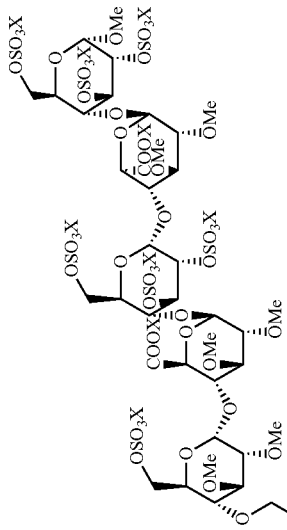
X = Na+

Peptide P12 (10 mg, 6.1 umol, 1 equiv.) was conjugated to pentasaccharide 7 (12.1 mg, 6.8 umol, 1.1 equiv.) according to method C. Yield: 4.16 mg (20%).

Conjugate C21
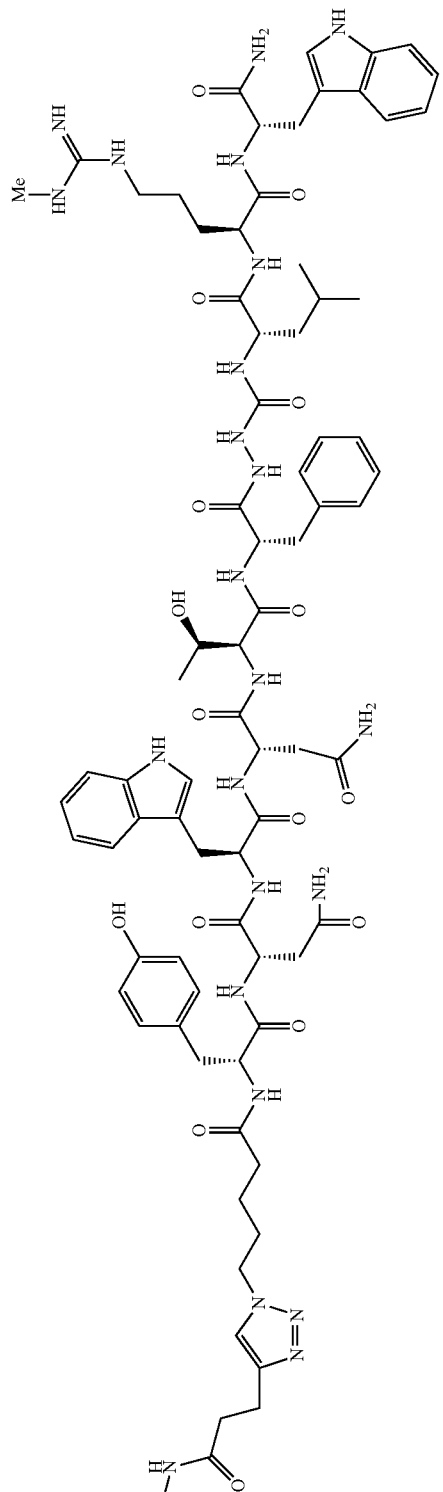
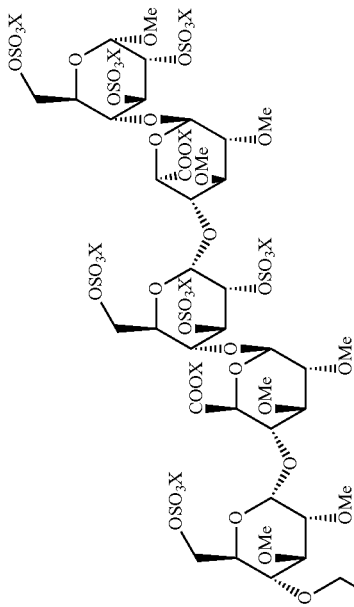
X = Na+

Peptide P13 (4.7 mg, 3.1 umol, 1 equiv.) was conjugated to pentasaccharide 7 (9.2 mg, 4.7 umol, 1.5 equiv.) according to method C. Yield: 2.6 mg (24%). Theoretical mass: 3449. MS results: MIM=3264 observed.

Conjugate C22
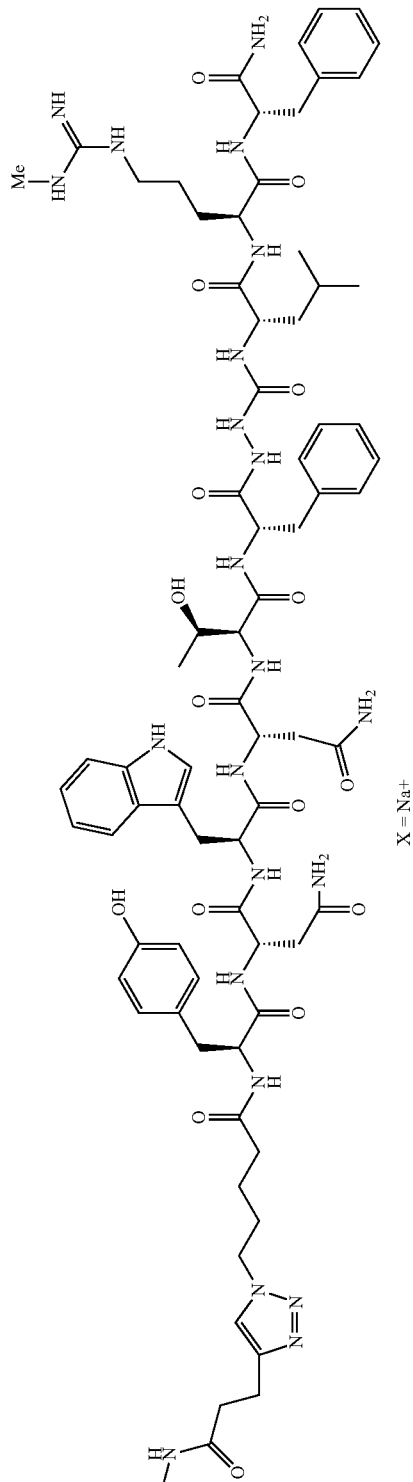
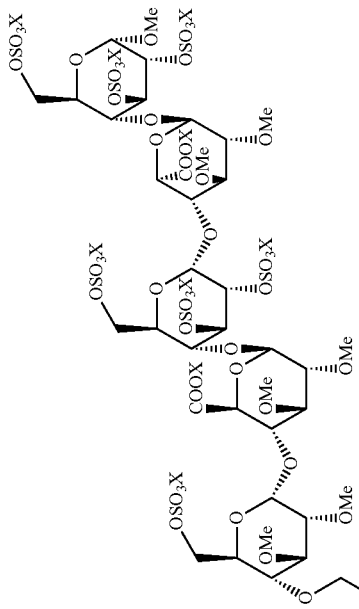
X = Na+

Peptide P14 (9.5 mg, 6 umol, 1 equiv.) was conjugated to pentasaccharide 7 (14.3 mg, 7.3 umol, 1.2 equiv.) according to method C. Yield: 15.2 mg (73%). Theoretical mass: 3425. MS results: MIM=3224.8 observed in the form of ammonium adducts for (M2+, M3+, M4+ and [M-SO3]n+). Accurate mass and isotope fit are in agreement with structural formula.

Conjugate C23
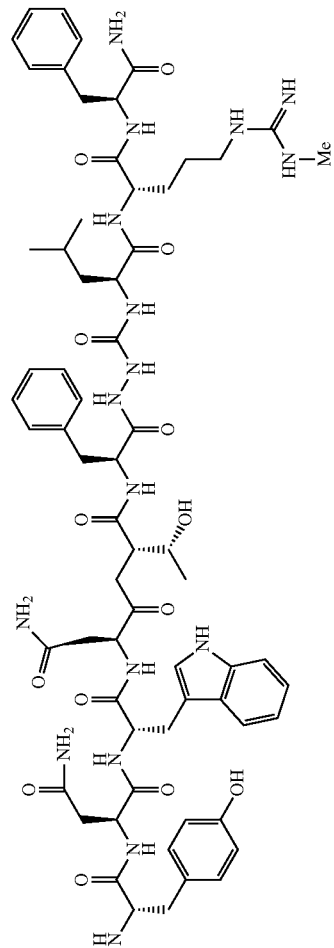
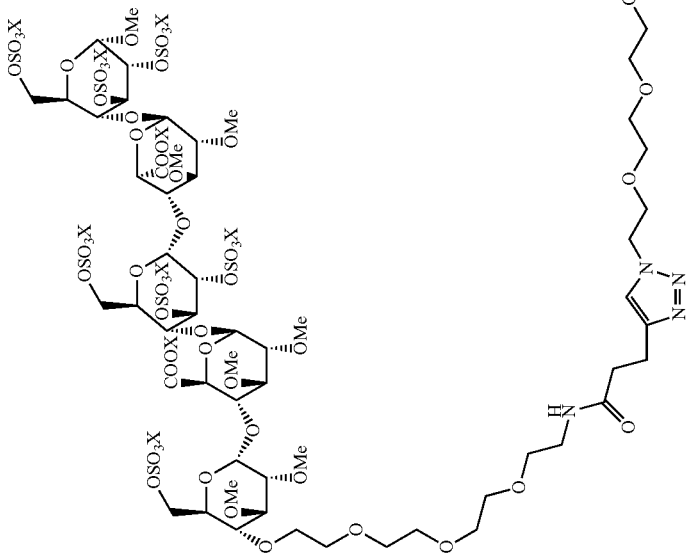
X = Na+

Peptide P15 (3.8 mg, 2.4 mmol, 1 equiv.) was conjugated to pentasaccharide 7 (5.6 mg, 2.9 mmol, 1.2 equiv.) according to method C. Yield: 2.4 mg (28%). Theoretical mass: 3559. MS results: ammonium adducts of MIM 3359 (M-9 Na).

Conjugate C24
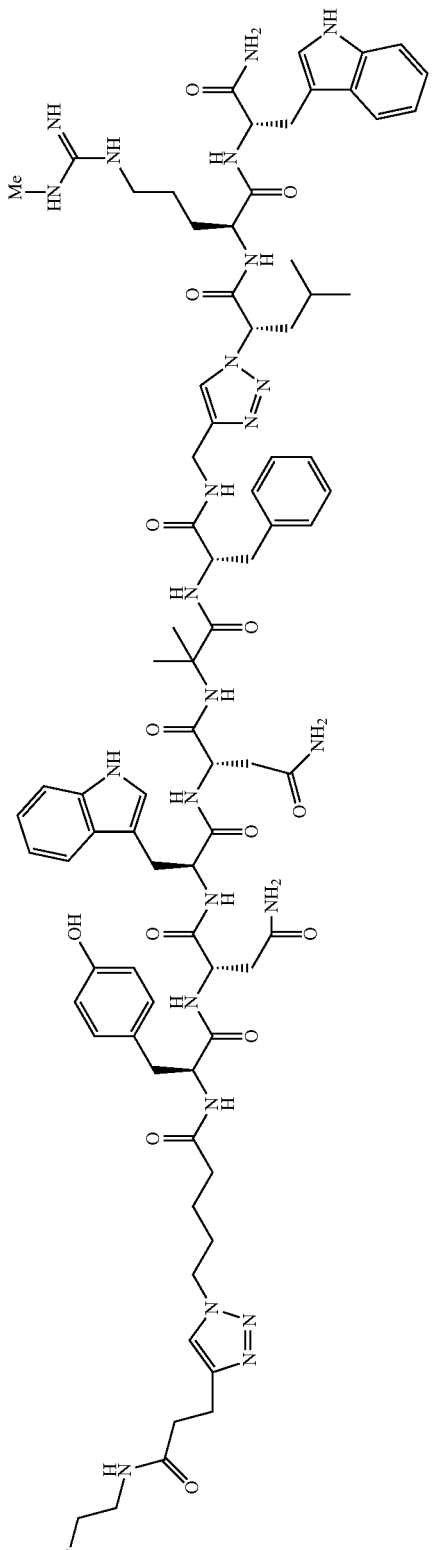
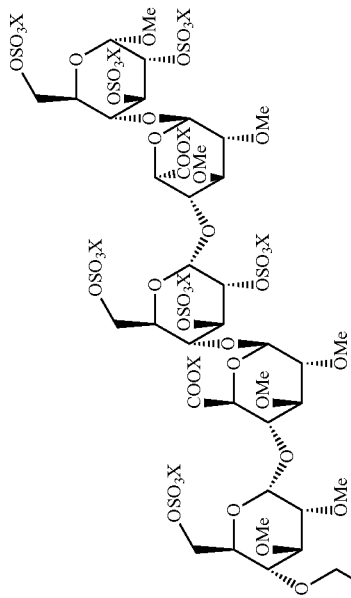
X = Na+

Peptide P16 (4.7 mg, 3.1 umol, 1 equiv.) was conjugated to pentasaccharide 7 (9.2 mg, 4.7 umol, 1.5 equiv.) according to method C. Yield: 7.2 mg (71%).

Conjugate C25
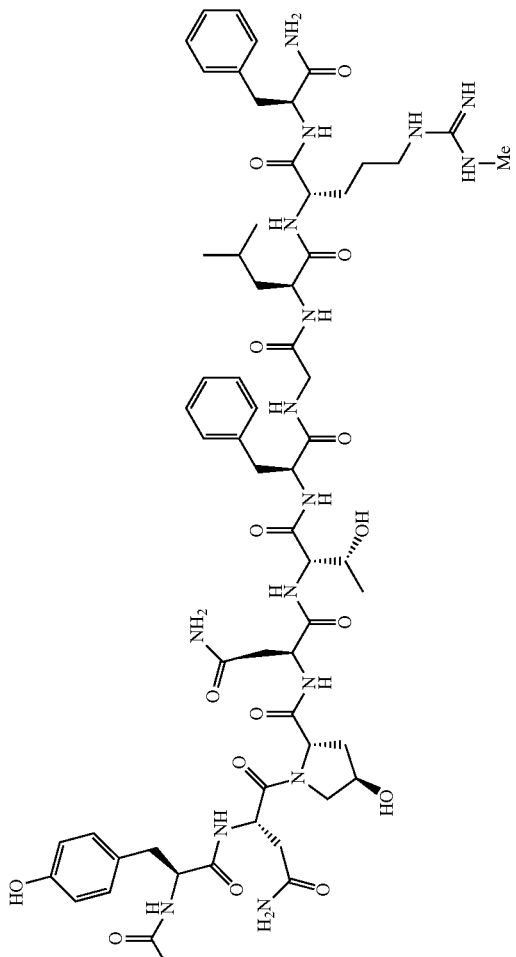
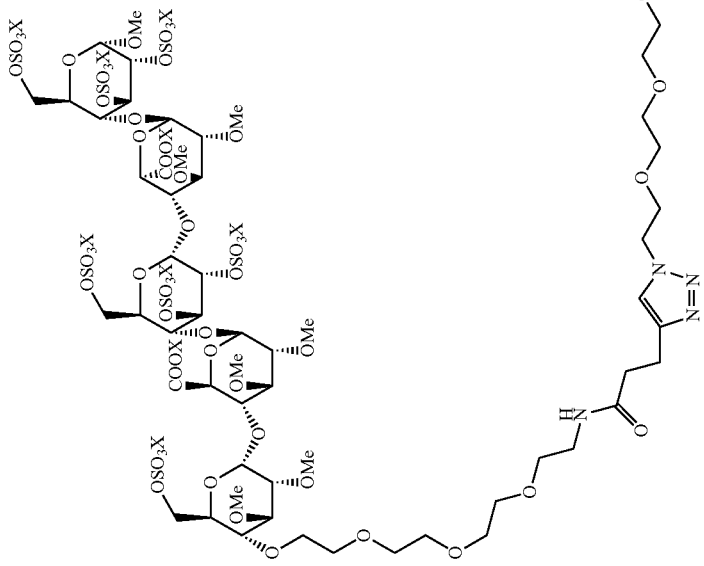
X = Na+

Peptide P17 (11.6 mg, 7.29 umol, 1 equiv.) was conjugated to pentasaccharide 6 (20.6 mg, 10.9 umol, 1.5 equiv.) according to method C. Yield: 8.62 mg (35%). Theoretical mass: 3411. MS results: MIM=3232.95. observed in the form of ammonium adducts for (M2+, M3+, M4+ and [MSO3]n+). Accurate mass and isotope fit are in agreement with structural formula.

Conjugate C26
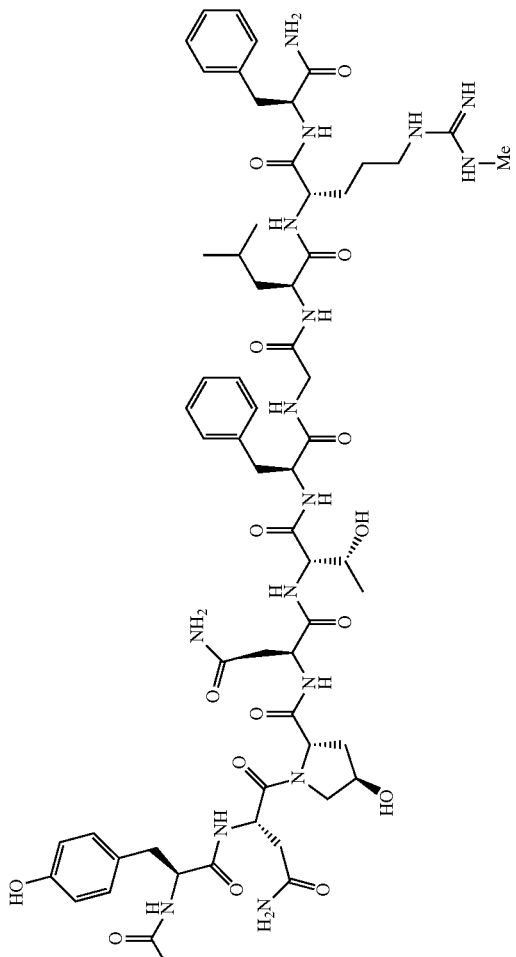
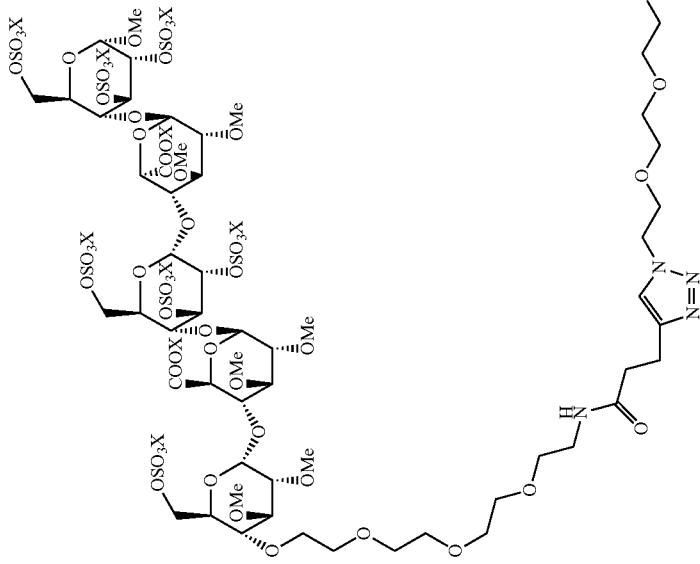
X = Na+

Peptide P17 (11.2 mg, 7.29 umol, 1 equiv.) was conjugated to pentasaccharide 7 (12.5 mg, 10.9 umol, 1.5 equiv.) according to method C. Yield: 8.58 mg (36%). Theoretical mass: 3499. MS results: MIM=3298.8 observed in the form of ammonium adducts for (M2+, M3+, M4+ and [MSO3]n+). Accurate mass and isotope fit are in agreement with structural formula.

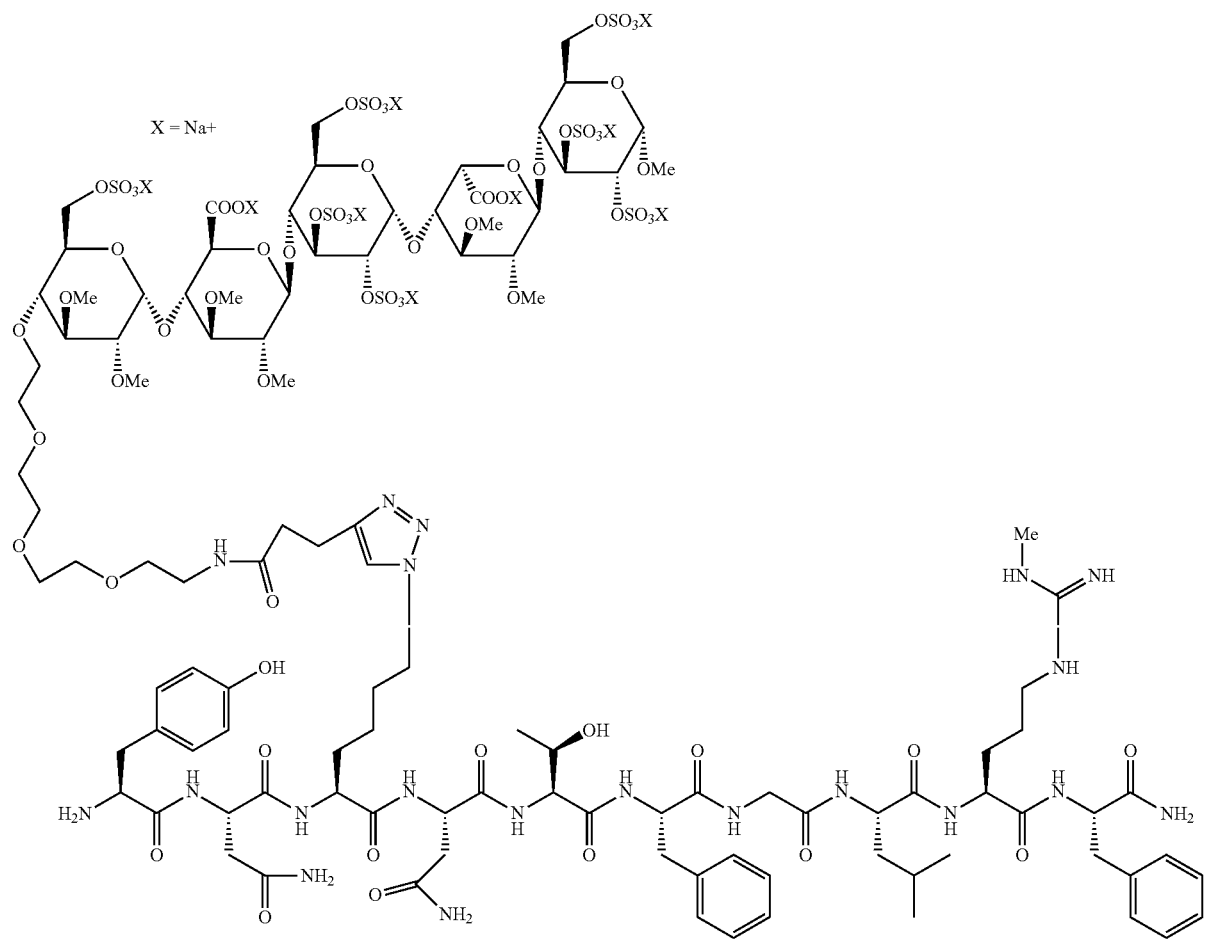

Conjugate C27

Peptide P18 (8 mg, 5.24 umol, 1 equiv.) was conjugated to pentasaccharide 7 (15.5 mg, 7.9 umol, 1.5 equiv.) according to method C. Yield: 7.8 mg (50%). Theoretical mass: 3266.9. MS results: MIM=3066.8 observed in the form of ammonium adducts for (M2+, M3+, M4+ and [MSO3]n+). Accurate mass and isotope fit are in agreement with structural formula.

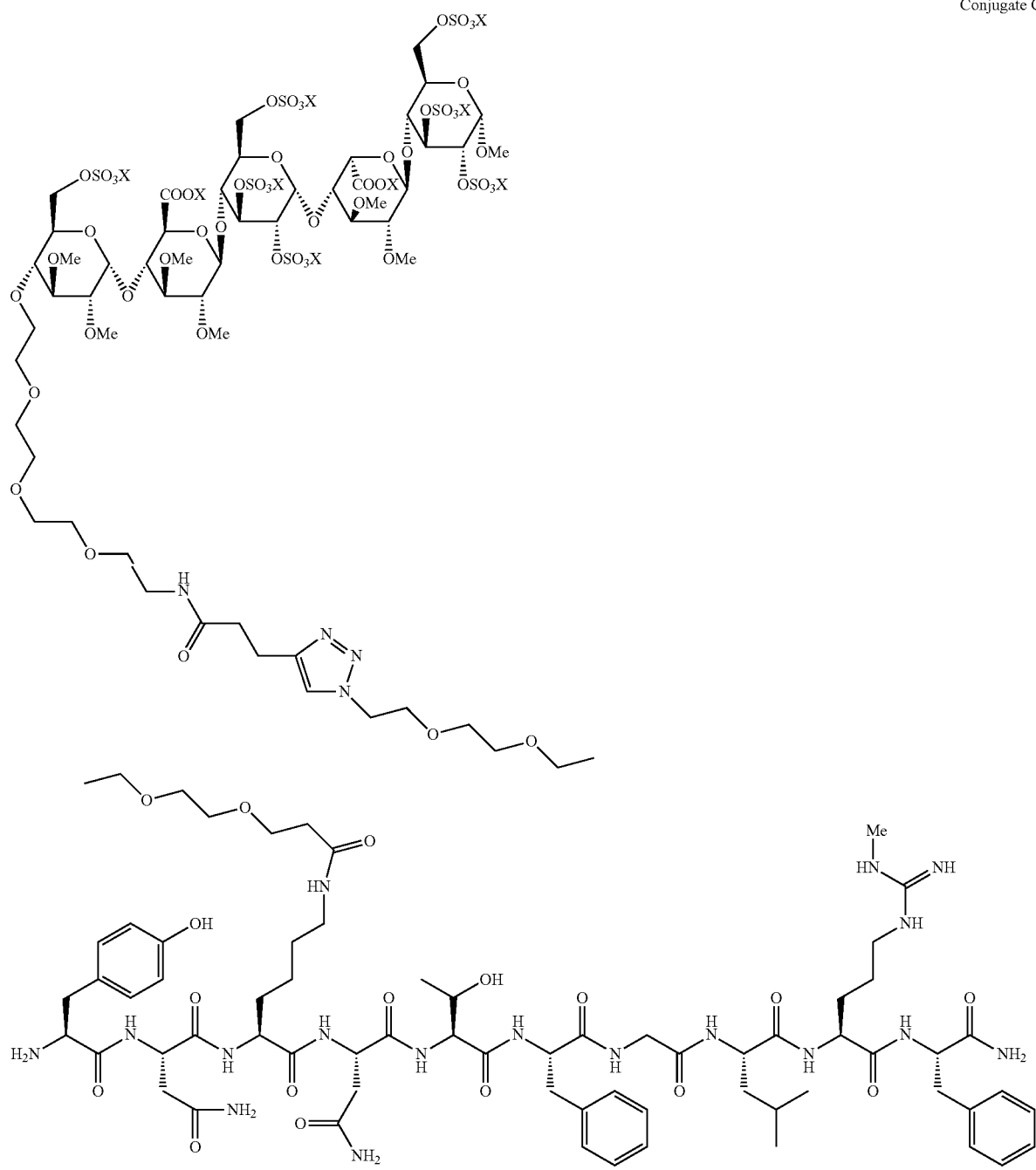
Conjugate C28
X = Na⁺
Peptide P19 (8.5 mg, 5.12 umol, 1 equiv.) was conjugated to pentasaccharide 7 (15.1 mg, 7.7 umol, 1.5 equiv.) according to method C. Yield: 5.8 mg (34%). Theoretical mass: 3514.2. MS results: MIM=3313.9 observed in the form of ammonium adducts for (M2+, M3+, M4+ and [MSO3]n+). Accurate mass and isotope fit are in agreement with structural formula.

Conjugate C29
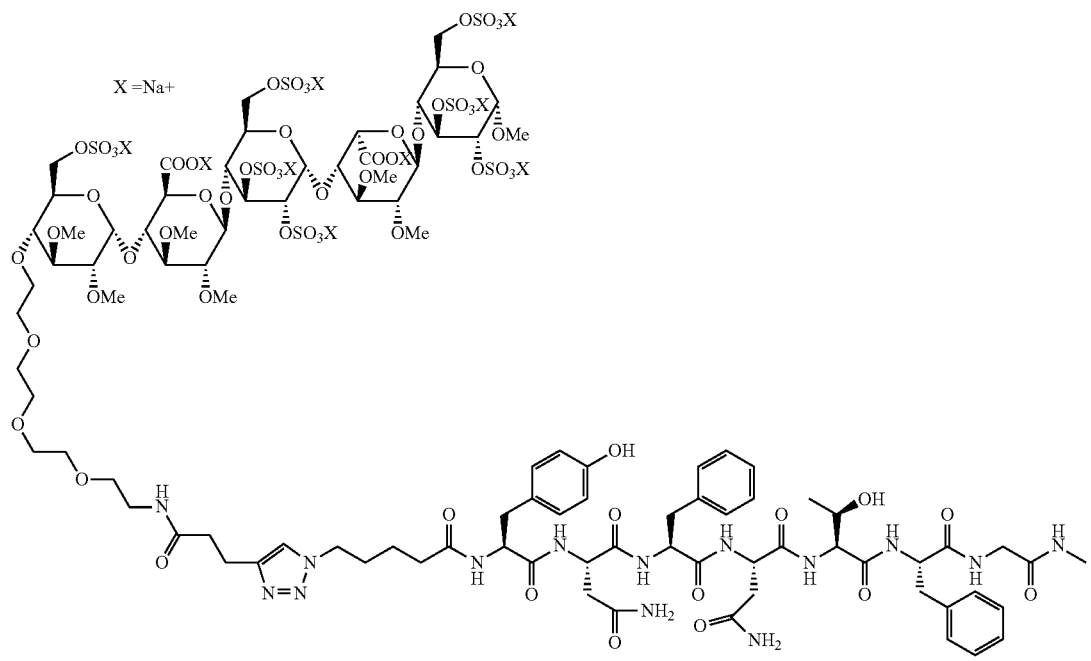
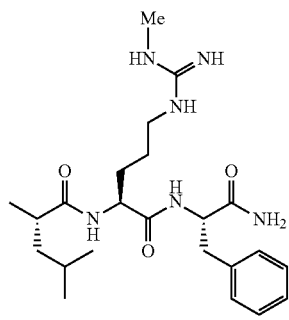
Peptide P20 (5.8 mg, 4.08 umol, 1 equiv.) was conjugated to pentasaccharide 7 (12.1 mg, 6.12 umol, 1.5 equiv.) according to method C. Yield: 5.86 mg (46%). Theoretical mass: 3384.9. MS results: MIM=3184.8 observed in the form of ammonium adducts for (M2+, M3+, M4+ and [MSO3]n+). Accurate mass and isotope fit are in agreement with structural formula.

Conjugate C30
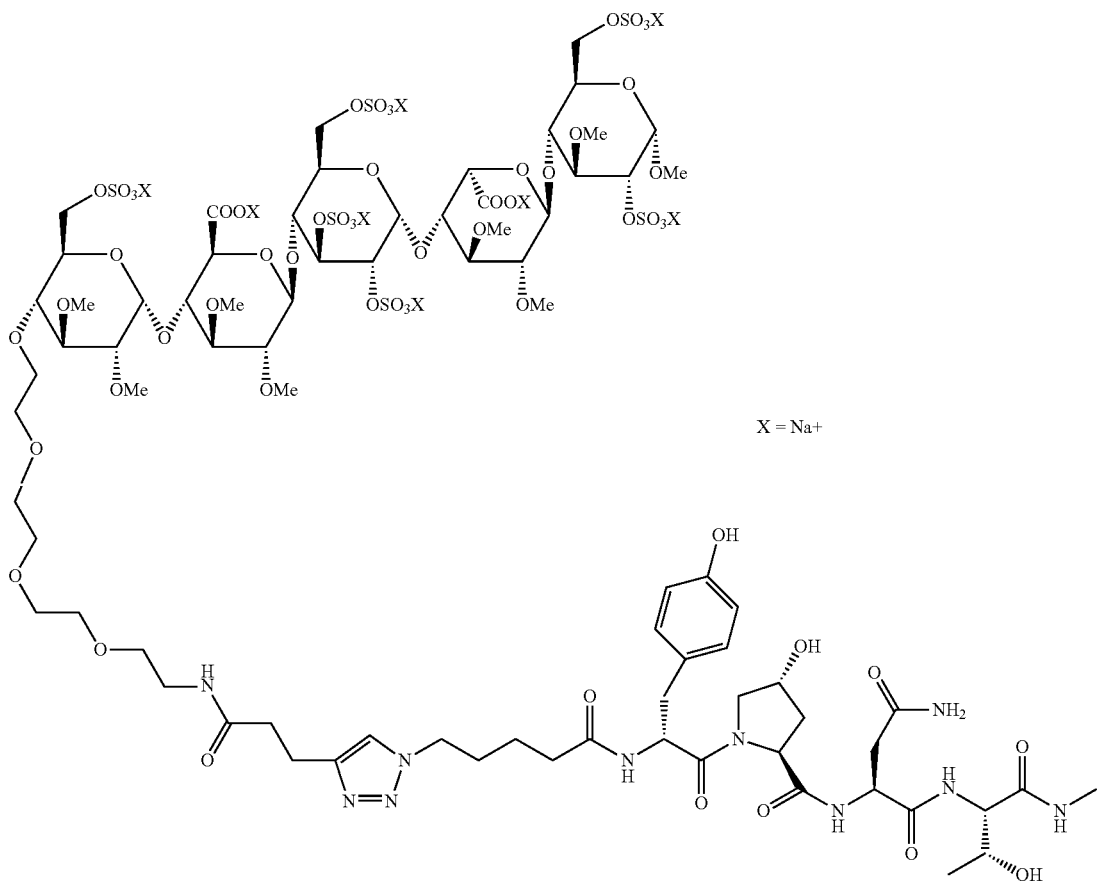
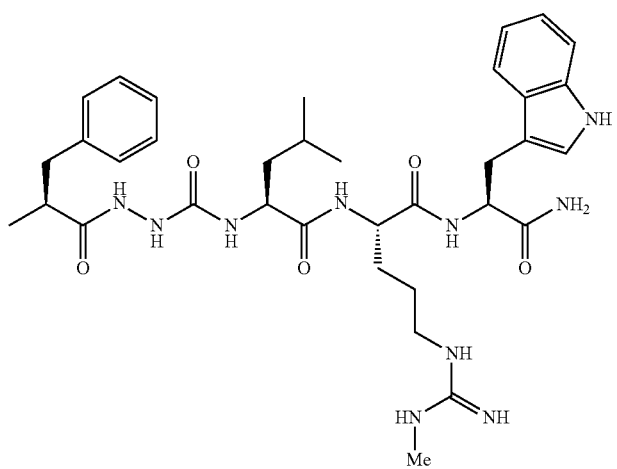
Peptide P22 (9.46 mg, 7.23 umol, 1 equiv.) was conjugated to pentasaccharide 6 (13.6 mg, 7.23 umol, 1.0 equiv.) according to method C. Yield: 5.42 mg (23%).

Conjugate C31
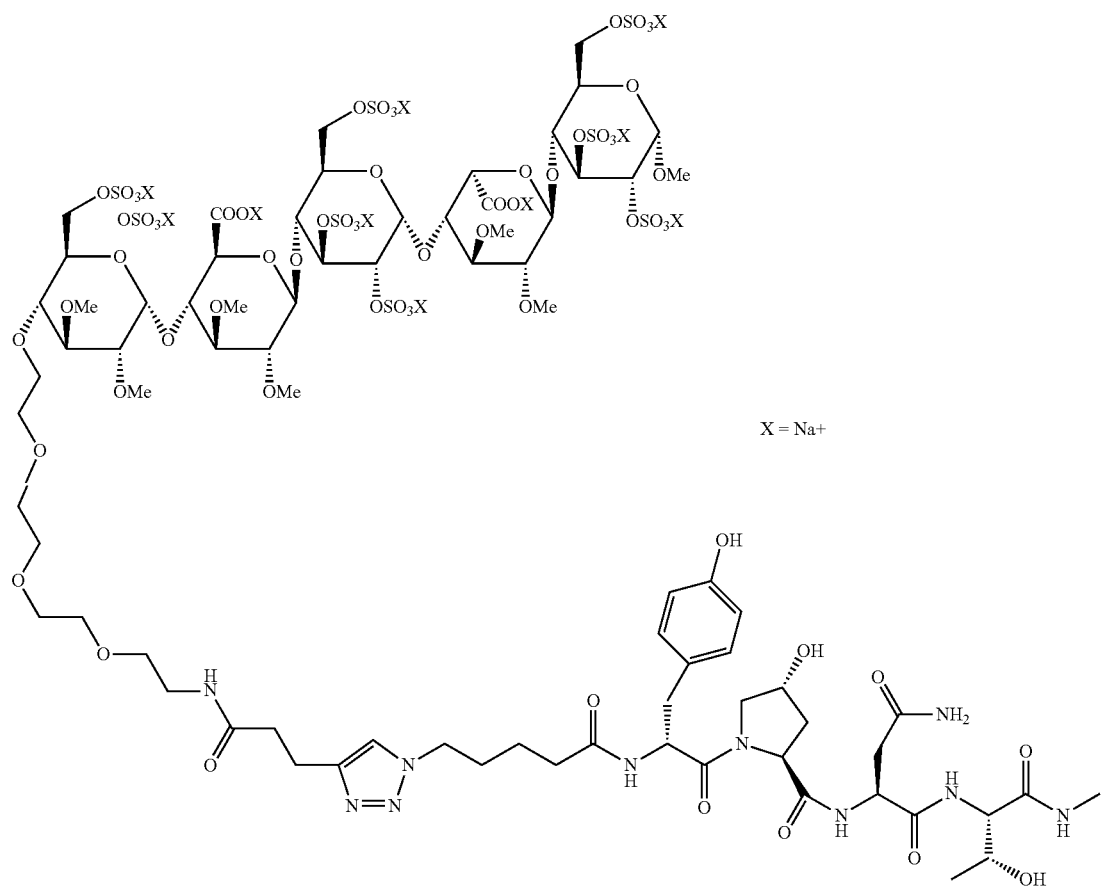
X = Na+
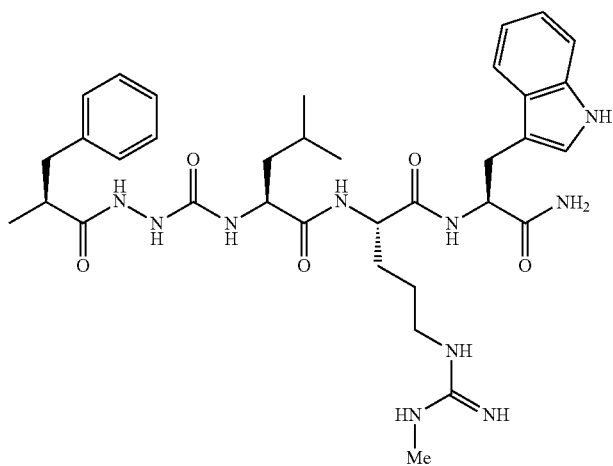
Peptide P22 (45.8 mg, 35 umol, 1 equiv.) was conjugated to pentasaccharide 7 (103 mg, 53 umol, 1.5 equiv.) according to method C. Yield: 93 mg (76%). MIM=3067.8 observed in the form of ammonium adducts for (M2+, M3+, M4+ and [M-SO3]n+). Accurate mass and isotope fit are in agreement with structural formula.

Conjugate C32
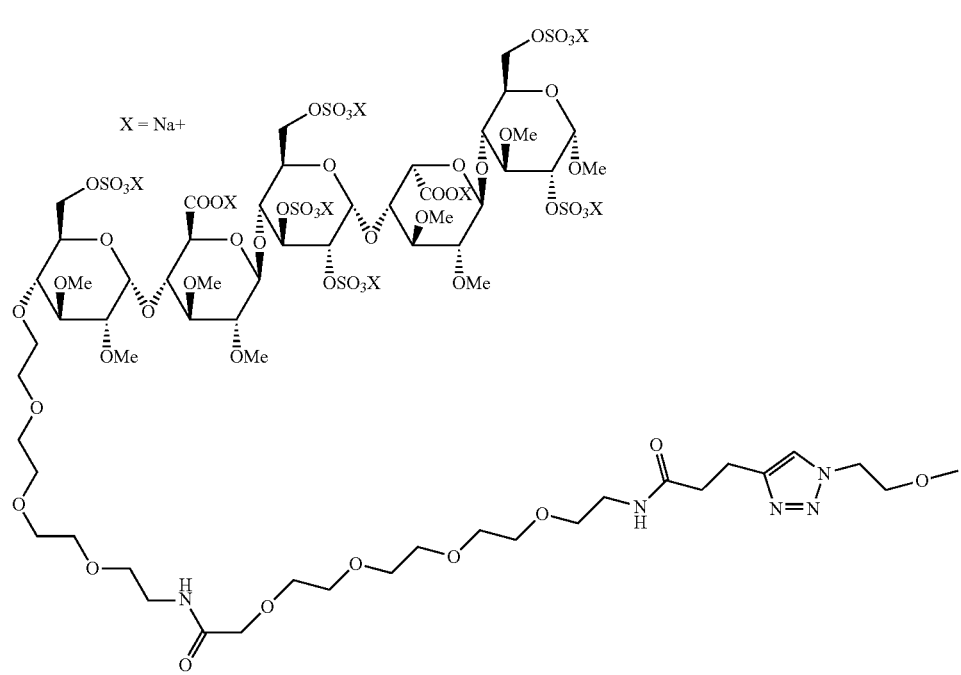
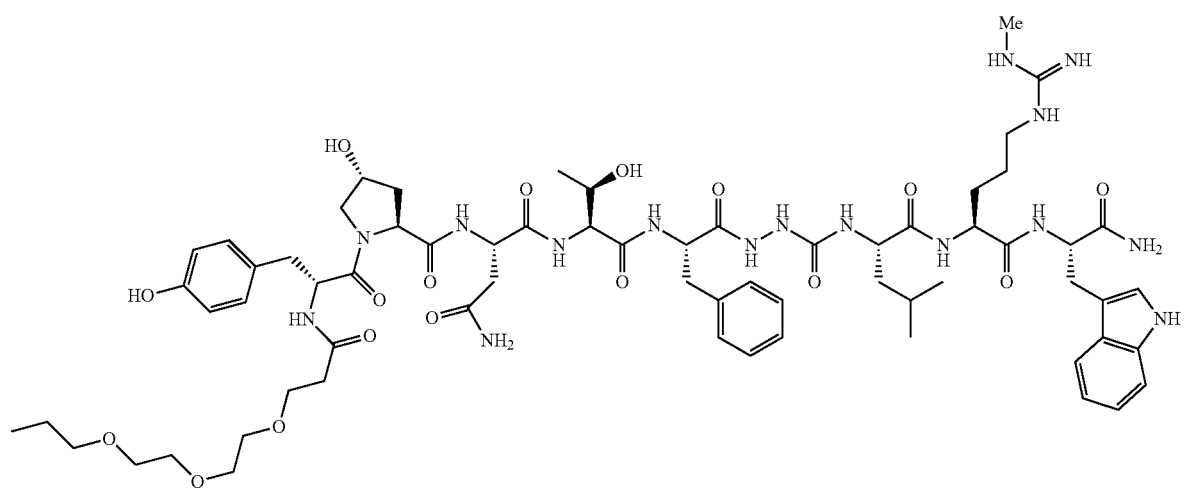
Peptide P23 (23.3 mg, 16 umol, 1 equiv.) was conjugated to pentasaccharide 9 (51.3 mg, 24 umol, 1.5 equiv.) according to method C. Yield: 14.7 mg (26%). Theoretical mass: 3570. MS results: MIM 3392 (product without sodium-salts) observed, no [M+H], but ammonium adducts observed Conjugate C33
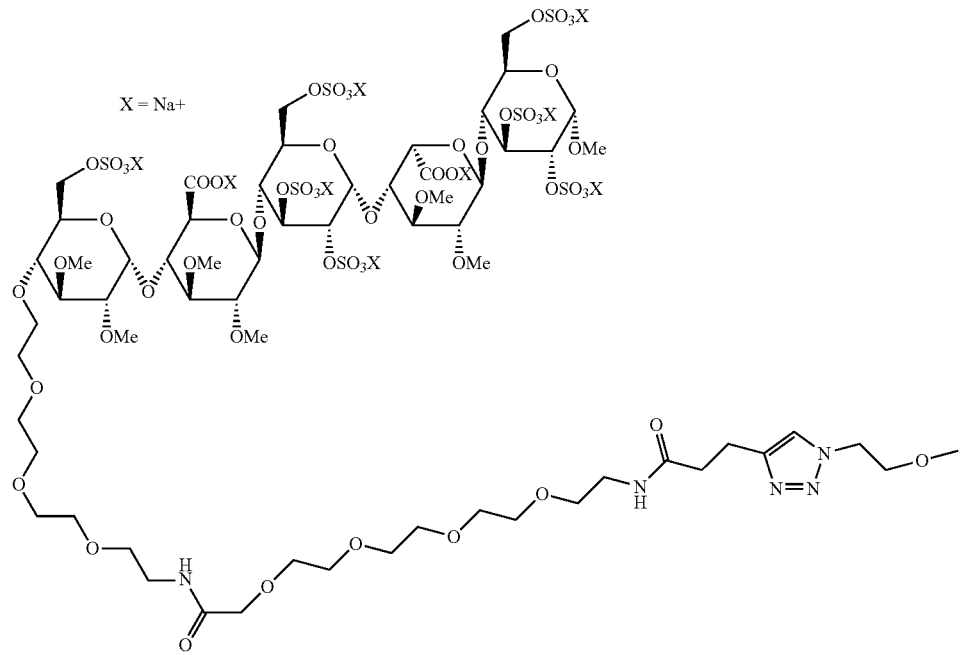
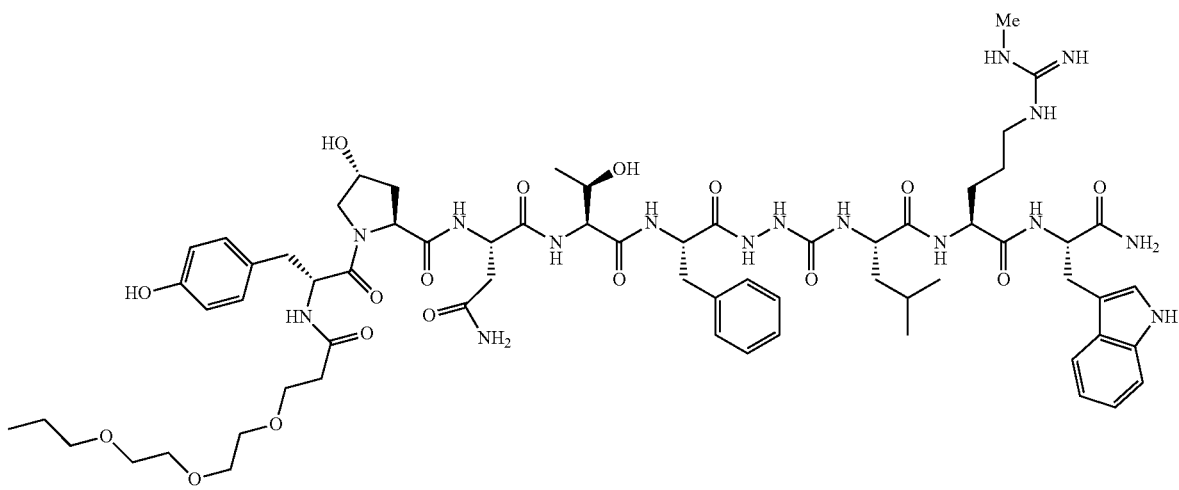
Peptide P23 (4.8 mg, 3.3 umol, 1 equiv.) was conjugated to pentasaccharide 10 (10.0 mg, 5.0 umol, 1.5 equiv.) according to method C. Yield: 5.5 mg (45%). Theoretical mass: 3658. MS results: MIM 3458 (product without sodium-salts) observed, no [M+H], but ammonium adducts observed Conjugate C34
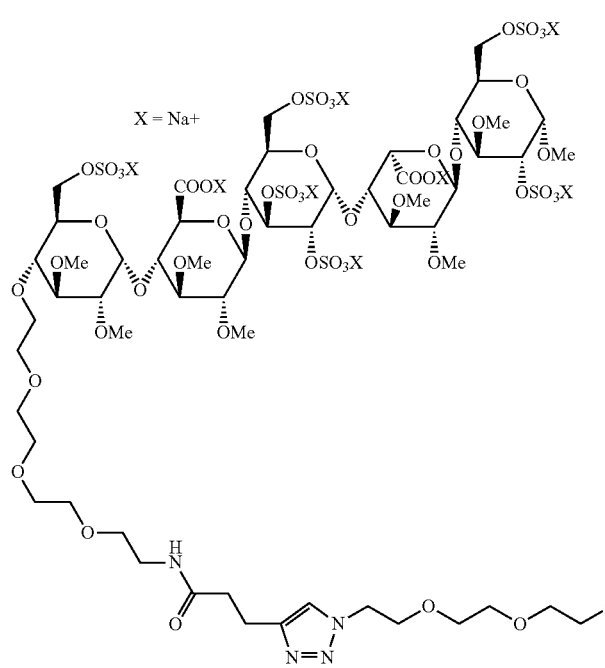
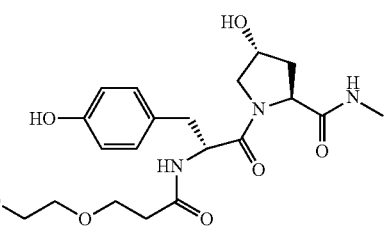
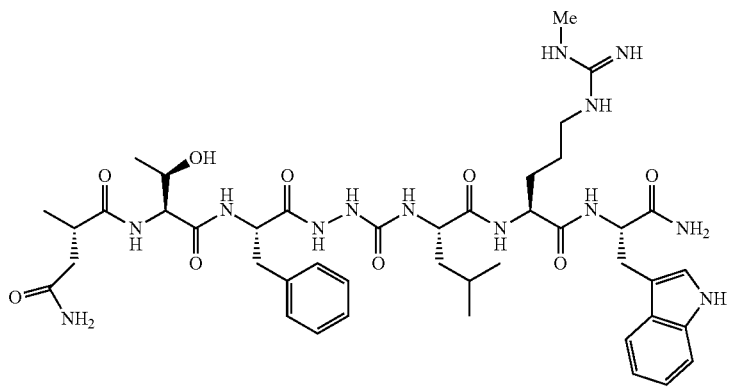
Peptide P23 (20.6 mg, 0.014 mmol, 1 equiv.) was conjugated to pentasaccharide 6 (40 mg, 0.021 mmol, 1.5 equiv.) according to method C. Yield: 30 mg (63%). Theoretical mass: 3337. MS results: ammonium adducts of MIM 3158.9 (M-8 Na).

Conjugate C35
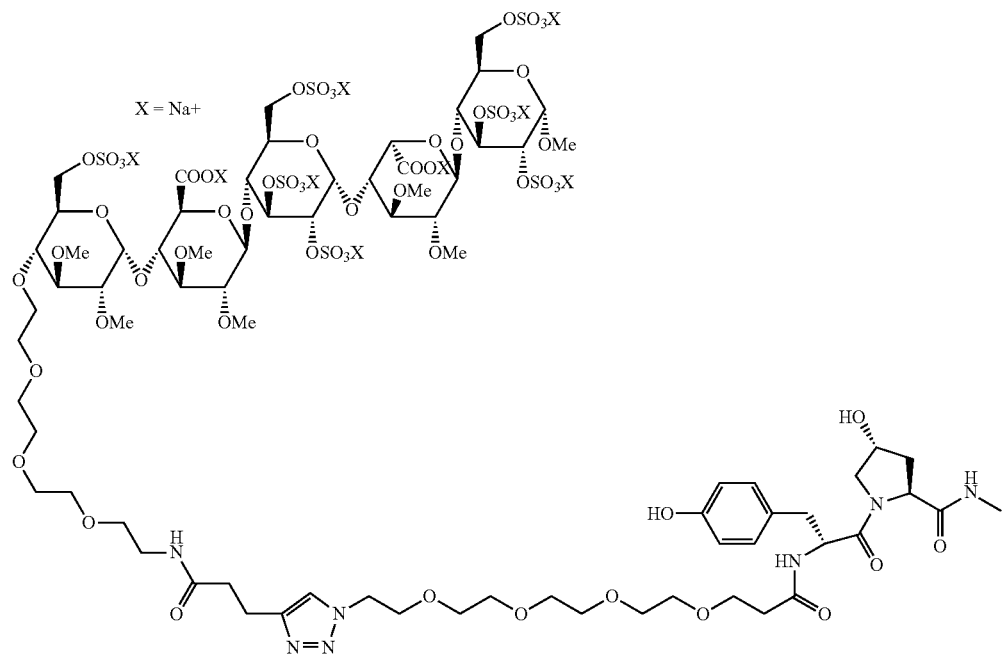
Peptide P23 (20.6 mg, 0.014 mmol, 1 equiv.) was conjugated to pentasaccharide 7 (42 mg, 0.021 mmol, 1.5 equiv.) according to method C. Yield: 25 mg (52%). Theoretical mass: 3425. MS results: ammonium adducts of MIM 3224.8 (M-9Na).

Conjugate C36
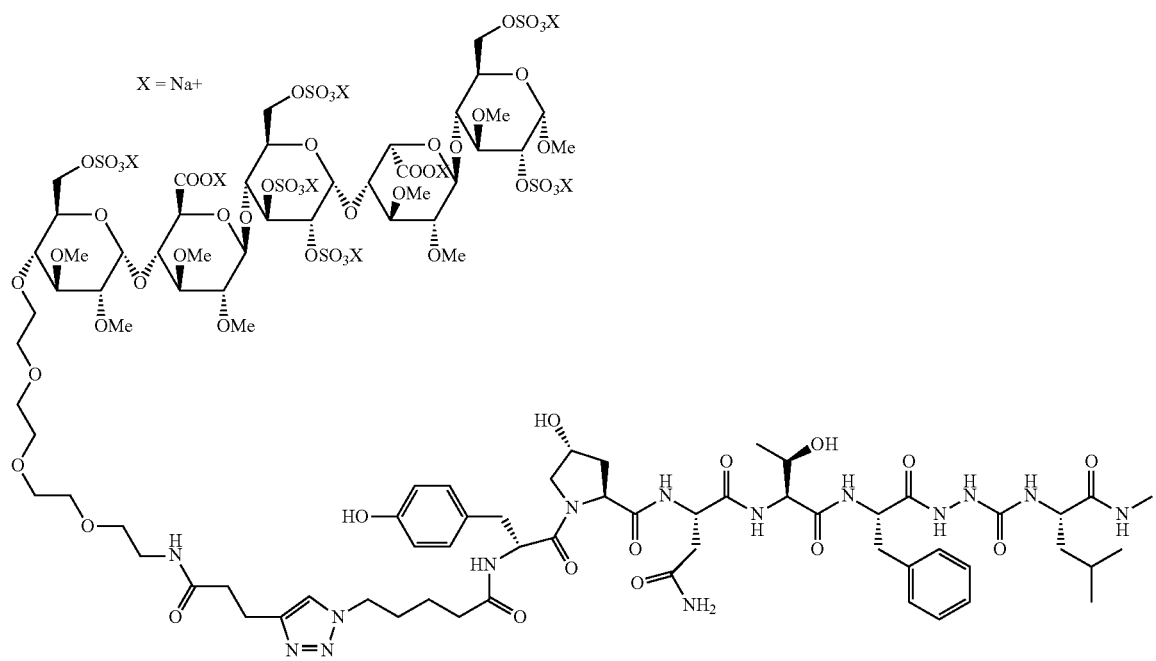
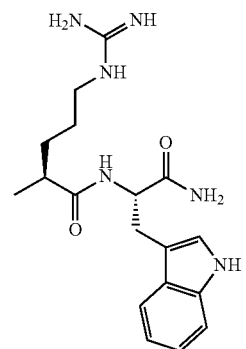
Peptide P24 (4.3 mg, 3.3 umol, 1 equiv.) was conjugated to pentasaccharide 6 (9.3 mg, 4.94 umol, 1.5 equiv.) according to method C. Yield: 4.0 mg (38%).

Conjugate C37
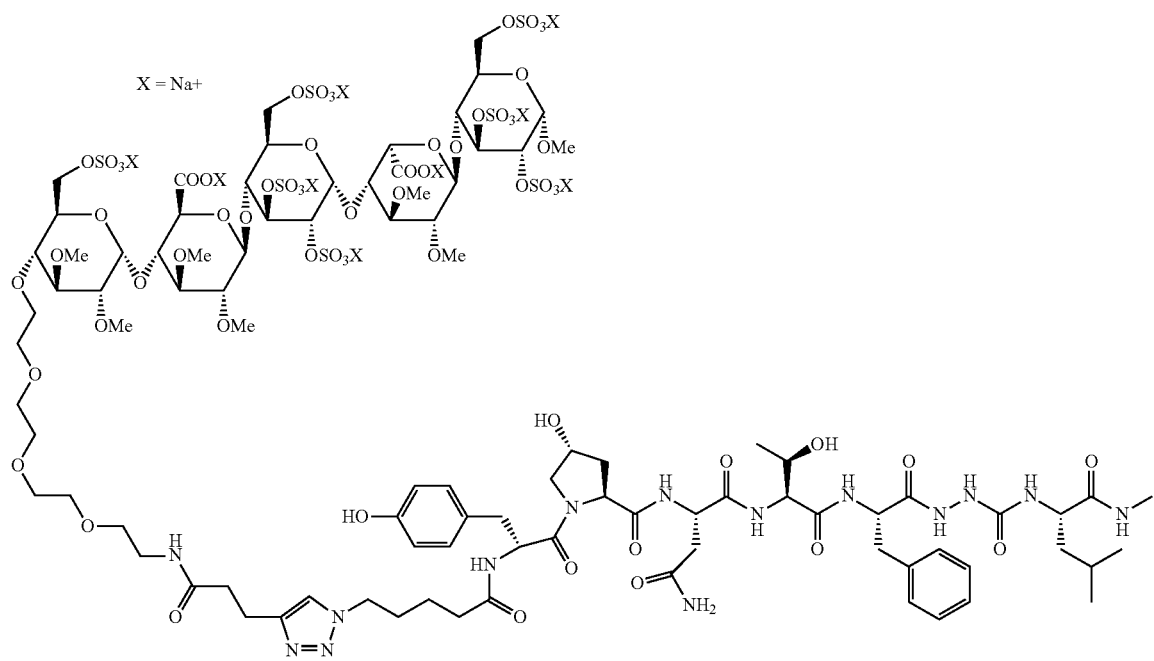
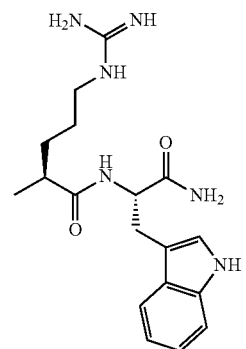
Peptide P24 (4.3 mg, 3.3 umol, 1 equiv.) was conjugated to pentasaccharide 7 (9.7 mg, 4.94 umol, 1.5 equiv.) according to method C. Yield: 2.2 mg (21%).

Conjugate C38
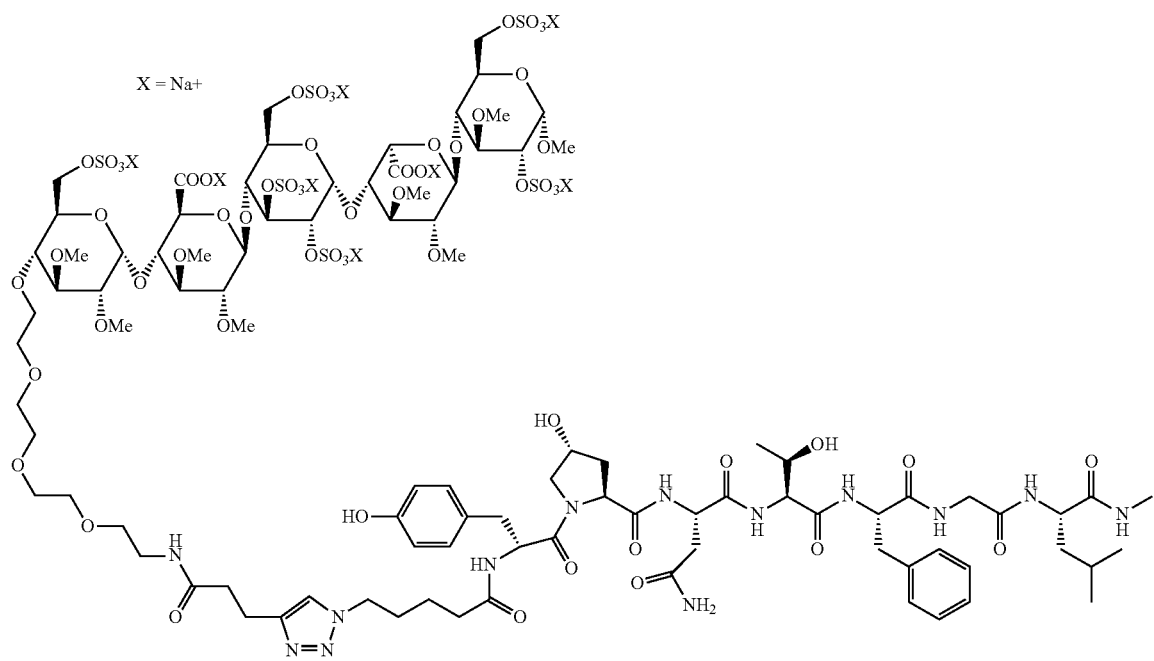
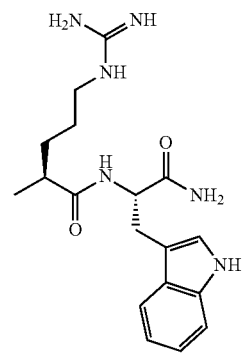
Peptide P25 (10.1 mg, 7.8 umol, 1 equiv.) was conjugated to pentasaccharide 6 (15.3 mg, 8.2 umol, 1.05 equiv.) according to method C. Yield: 12.8 mg (55%).

Conjugate C39
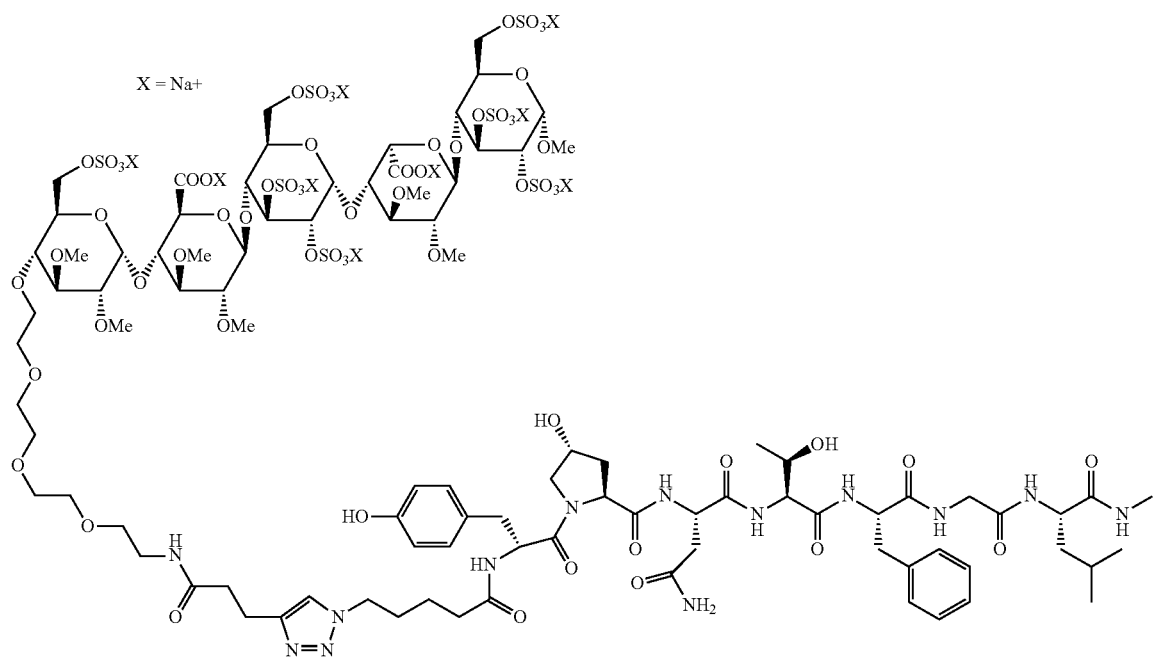
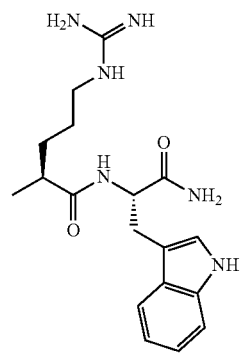
Peptide P25 (10.1 mg, 7.8 umol, 1 equiv.) was conjugated to pentasaccharide 7 (16.1 mg, 8.2 umol, 1.05 equiv.) according to method C. Yield: 15.2 mg (64%).

Conjugate C40
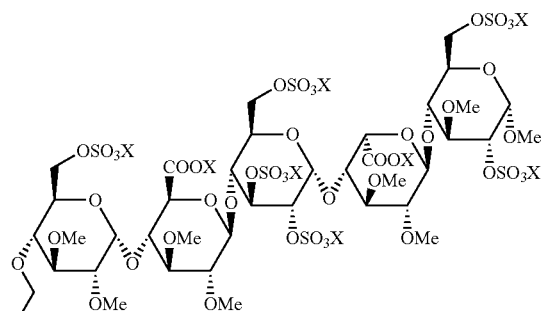
X = Na+
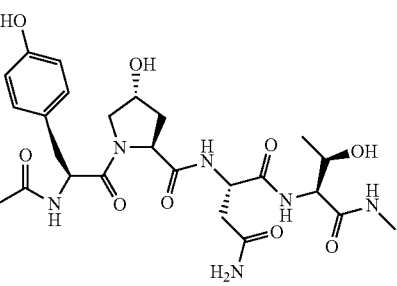
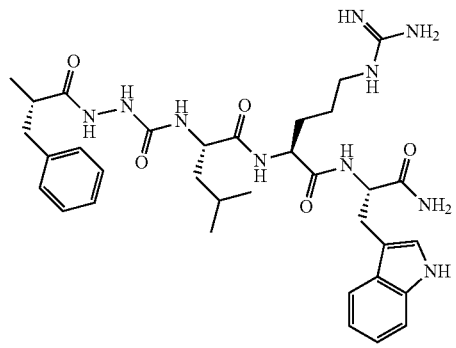
Peptide P26 (2.58 mg, 1.79 umol, 1 equiv.) was conjugated to pentasaccharide 6 (3.53 mg, 1.88 umol, 1.05 equiv.) according to method C. Yield: 1.61 mg (29%).

Conjugate C41
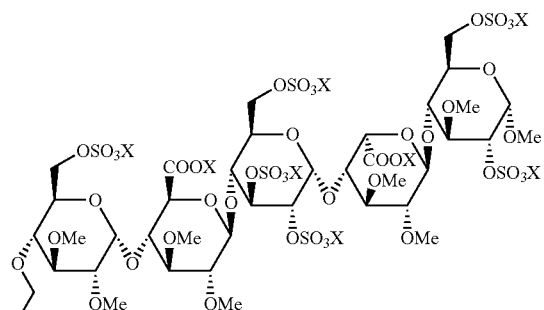
X = Na+
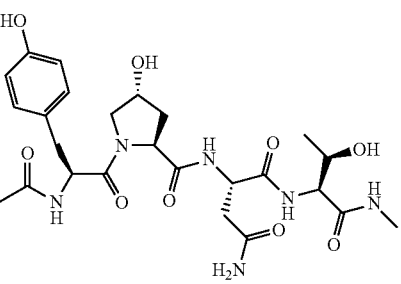
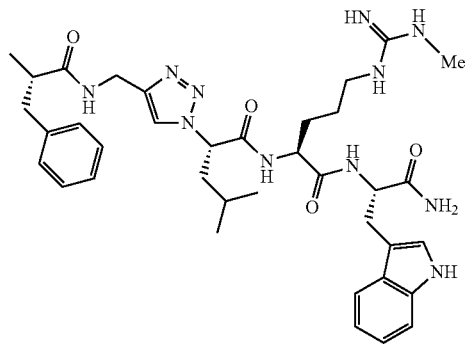
Peptide P27 (1.35 mg, 0.91 umol, 1 equiv.) was conjugated to pentasaccharide 6 (3.1 mg, 1.8 umol, 1.9 equiv.) according to method C. Yield: 0.96 mg (31%).

Conjugate C42

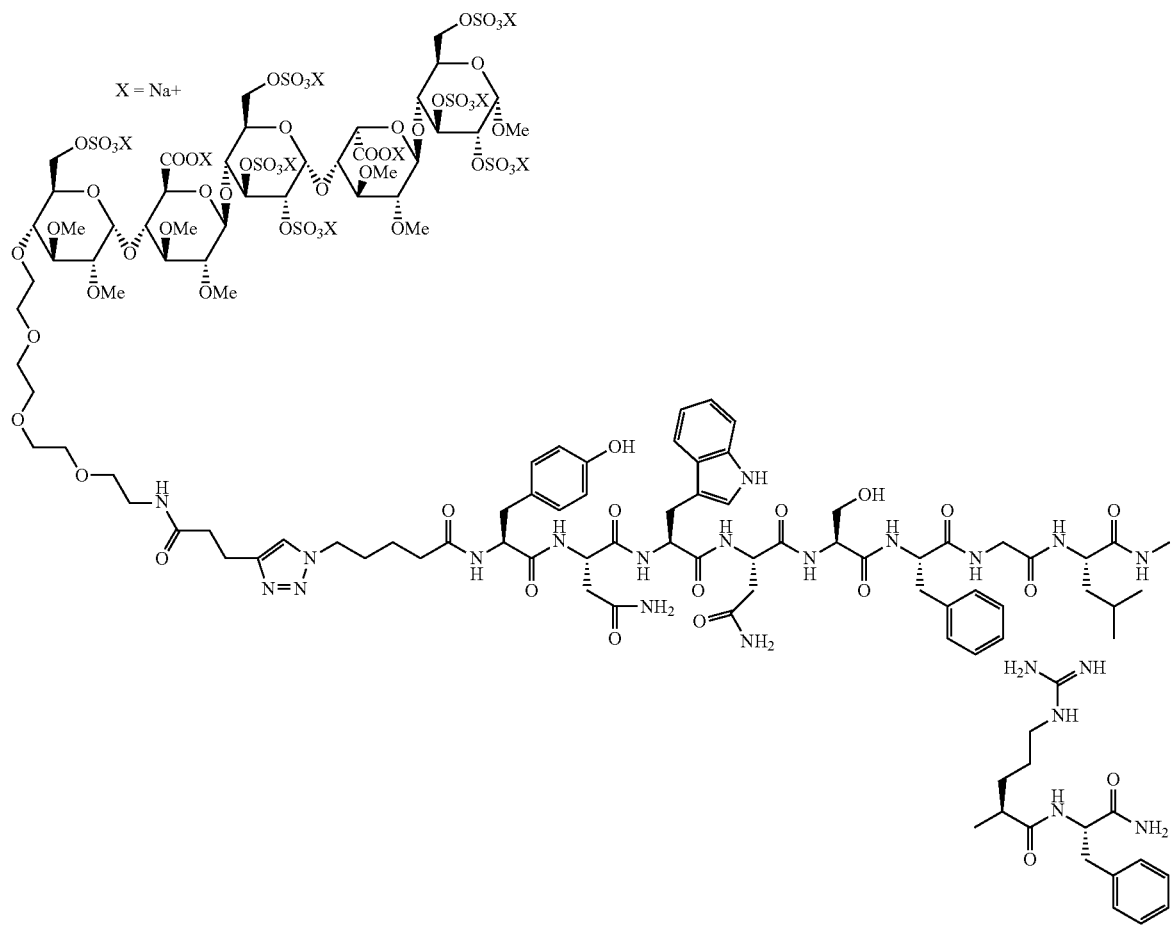

Peptide P21 (11.7 mg, 8.19 umol, 1 equiv.) was conjugated to pentasaccharide 7 (24.2 mg, 12 umol, 1.5 equiv.) according to method C. Yield: 16.3 mg (58%). Theoretical mass: 3396. MS results: MIM=3195.8 observed in the form of ammonium adducts for (M2+, M3+, M4+ and [MSO3]n+). Accurate mass and isotope fit are in agreement with structural formula.

Biological Activity

In Vitro Agonist Activity at the KISS-Receptor.

The in vitro agonistic activity of the kisspeptide-pentasaccharide conjugates of the invention at the $G\alpha_q$-coupled human GPR54-R was measured in the absence and presence of 20% human serum in a NFAT-regulated luciferase reporter gene assays. CHO-k1 cells were used that expressed the mitochondrially targeted aequorine and $G\alpha_{16}$ (from Euroscreen, Brussels, Belgium), a Nuclear Factor of Activated T-cells-responsive element (NFAT) under the control of a promoter directing the expression of a firefly luciferase reporter gene (pNFAT-TALuc obtained from Clontech, Mountain View, Calif.), and the human GPR54-R Hygro(+)-hGPR54WT c4; MSD). These cells were cultured in Dulbecco's Modified Eagle Medium: Nutrient Mixture F-12 (DMEM/F12) (Invitrogen, Carlsbad, Calif.), supplemented with 10% (vol/vol) filtered bovine serum (Hyclone, Thermo Fisher Scientific, Waltham, Mass.), 100 U/ml penicillin G, 100 µg/ml streptomycin, 400 µg/ml Geneticin and 400 µg/ml Hygromycin (Invitrogen). Kisspeptide-pentasaccharide conjugates and Kisspeptin-10 (Metastin 45-54 from Pepnet; Louisville, Ky.) were diluted in assay medium (DMEM/F12 containing 1 µg/ml insulin (Diosynth, Oss, The Netherlands), 5 µg/ml apo-transferin (Sigma-Aldrich, St. Louis, Mo.) and 0.1% (vol/vol) bovine serum albumine (BSA, Sigma Aldrich)) in a 10-point serial dilution. Kisspeptin-10 was used as a standard. 10 µl of kisspeptide-pentasaccharide conjugate and Kisspeptin-10 dilutions were added to a white 384-wells culture plate (Perkin Elmer, Boston, Mass.). When the conjugates were tested in the presence of a final percentage of 20% human serum, 10 µl assay medium containing 60% human serum (Sigma-Aldrich, #H4522) was added to the wells. In the absence of human serum, 10 µl of assay medium was added. Cells were harvested and diluted to a concentration of 7.5E5 cells/ml in assay medium without 0.1% BSA. 10 µl of cell solution was added to the compound wells. After incubation for 4 hours in a humidified atmosphere at 5% $CO_2$ and 37° C., the plate was left at room temperature for 30 minutes. Subsequently, 15 µl of Steadylite™ solution (PerkinElmer, Boston, Mass.) was added and the cells, protected from light, were allowed to lyse for 30 min at room temperature. Luminescence, indicated as relative luminescence units (RLU), was measured on an Envision Multilabel reader (PerkinElmer).

The effect of kisspeptide-pentasaccharide conjugate was calculated as percentage of the maximum effect of Kisspeptin-10 (effect at 1E-6M) and the minimum effect (assay medium). Curves were fit by nonlinear regression using the sigmoidal dose-response equation in GraphPad Prism version 4.03 (GraphPad, San Diego, Calif.), resulting in a $pEC_{50}$ value for the conjugate (Table I).

In Vitro Stability Study of Kisspeptide-Pentasaccharide Conjugates in Human Serum.

Test compound is added to 1.5 mL human serum in a 96-wells deepwell plate in a final concentration of 750 nM. The compound is mixed and immediately thereafter a 100 µl sample is harvested in a 96-wells 2D-tuberack (T=0 sample). The 2 D-tubes are closed with rubber tube caps and the sample plate is stored at −20° CF. in the freezer. The deepwell plate is put into an incubator which was set at humidified (95%) atmosphere at 5-7% CO2 and 37° C. for an incubation period of maximum 240 h. During this incubation period, samples of 100 µl are collected on various time intervals, dependent on the test compound used; time points 0, 1, 2, 3, 6, 24, 48, 72 h in case of Kisspeptides and 0, 3, 6, 24, 48, 72, 168, 240 h in case of kisspeptide-pentasaccharide conjugates. Sample plates are put on ice in case of sampling and stored at −20° C. until analysis by LC/MS/MS.

Determination of Kisspeptide-Pentasaccharide Conjugates in Animal and Human Plasma by LC-MS/MS Kisspeptide-pentasaccharide conjugates are determined by LC-MS/MS after extraction from 20 or 100 µL plasma samples by protein precipitation. Protein precipitation is executed after the addition of heparin and by common acetonitrile precipitation. For LC-MS/MS analysis, the compounds are separated over an XTerra RP8 column and using a gradient mobile phase of ammonium acetate buffer and acetonitrile at a fixed column temperature. MS/MS detection is done with a triple quadrupole mass spectrometer and employing negative ion electrospray ionization. The mass spectrometer is set up to achieve a known degree of in source fragmentation, where the initially formed multiply charged negative ions lose one or more $SO_3$ molecules. The most abundant of these secondary ions are then subjected to a common MS/MS experiment in which a single $SO_3$ loss is monitored. The Q1 and Q3 mass filter settings for this MS/MS experiment have commonly been determined in method development. The Q1 and Q3 masses are highly selective for each individual kisspeptide-pentasaccharide conjugate. Internal standardization is accomplished by adding a different conjugate of approximately the same size to the bioanalytical samples. Although the limit of quantitation may vary for the individual kisspeptide-pentasaccharide conjugates, the observed sensitivity generally supports an assay range of 0.1 nM to 2000 nM sample concentrations.

The obtained concentration data are analyzed from the plasma concentration vs time curve by means of the Non Compartmental Analysis (NCA) module in WinNonlin (Pharsight). The rate of compound loss is expressed as a half-life (plasma $t^{1/2}$). The $t^{1/2}$ for the test compound can be determined by plotting the natural logarithm (ln) of the measured concentrations against time and fitting the line through all data points. The gradient of this line is the first order rate constant (k) for substrate disappearance and is determined by regression analysis. The rate constant is converted to a half-life according to the following equation:

$$\text{In vitro half-life}(t^{1/2}) = -\ln 2/k$$

TABLE I

Agonist potencies of kisspeptide-pentasaccharide conjugates of the invention at the human KISS-receptor in the absence and presence of 20% serum in a NFAT-luciferase assay in CHO cells and in vitro $T_{1/2}$ in human serum.

| Conjugate | $pEC_{50}$ | $pEC_{50}$ serum | $T_{1/2}$ |
|---|---|---|---|
| C1 | 9.91 | 8.09 | >240 h |
| C2 | 10.11 | 8.04 | |
| C3 | 10.11 | 8.20 | |
| C4 | 10.14 | 8.11 | |
| C5 | 9.73 | 8.09 | |
| C6 | 9.83 | 8.25 | |
| C7 | 9.80 | 9.30 | 171 h |
| C8 | 9.80 | 8.14 | >240 h |
| C9 | 9.66 | 8.66 | |
| C10 | 9.91 | 9.28 | 121 h |
| C11 | 9.76 | 8.16 | >240 h |
| C12 | 9.95 | 9.01 | |
| C13 | 9.47 | 8.33 | |
| C14 | 9.35 | 8.08 | |
| C15 | 9.24 | 8.08 | |
| C16 | 9.43 | 8.63 | |
| C17 | 9.11 | 8.07 | |
| C18 | 9.47 | 8.60 | 233 h |
| C19 | 9.48 | 9.13 | 175 h |
| C20 | 9.30 | | >240 h |
| C21 | 9.83 | 8.07 | |
| C22 | 10.14 | 8.41 | >240 h |
| C23 | 9.68 | 8.61 | |
| C24 | 10.17 | 8.21 | |
| C25 | 9.43 | 8.99 | 188 h |
| C26 | 9.53 | 8.01 | >240 h |
| C27 | 9.96 | 8.29 | |
| C28 | 9.85 | 8.37 | |
| C29 | 9.39 | 8.09 | |
| C30 | 10.32 | 9.71 | |
| C31 | 10.30 | 8.70 | >240 h |
| C32 | 9.82 | 9.45 | |
| C33 | 10.23 | 9.04 | |
| C34 | 10.39 | 9.85 | 138 h |
| C35 | 10.37 | 8.86 | >240 h |
| C36 | 10.90 | 10.04 | |
| C37 | 10.90 | 8.94 | |
| C38 | 10.37 | 9.50 | |
| C39 | 10.19 | 8.57 | |
| C40 | 9.46 | 8.78 | |
| C41 | 10.40 | 9.60 | |
| C42 | 8.8 | 7.5 | 121 h |
| Kiss-10 | 9.00 | 9.00 | 0.1 h |
| P28 | | | |
| P29 | 10.00 | 10.30 | 5.4 h |

In Vivo Pharmacokinetic Study in Rat.

The pharmacokinetics of conjugate C8 were determined after administration of 40 nmol/kg IV in male and of 200 nmol/kg SC in female Sprague-Dawley rats. The measured PK parameters (Tables II and III) show that the plasma clearance of the conjugate was very low (0.08-0.012 mL/min/kg) and that the distribution volume in steady state is limited to the blood volume.

The terminal elimination half-life for conjugate C8 was 11.5 hr in rat. Following subcutaneous administration, absorption was rapid ($t_{max}$ 2.7-3.3 hr) and % bioavailability was 94 in rat (Table II).

TABLE II

Pharmacokinetics in rats

| Parameters | Rat |
|---|---|
| Dose IV nmol/kg (µg/kg) | 40 (137) |
| $AUCN_{(0-\infty)}$ (nM · hr · kg/µg) IV | 60.4 |

TABLE II-continued

Pharmacokinetics in rats

| Parameters | Rat |
|---|---|
| $Cl_p$ (mL/min/kg) | 0.08 |
| $Vd_{ss}$ (L/kg) | 0.067 |
| $t_{1/2}$ (hr) IV | 11.5 |
| Dose nmol/kg (μg/kg) | 200 (685) |
| $AUCN_{(0-\infty)}$ (nM · hr · kg/μg) SC, (IM, ewe) | 56.5 |
| F (%) | 93.5 |
| $C_{max}$ (nM) | 2310 |
| $T_{max}$ (hr) | 2.7 |

AUCN = dose-normalized area under the plasma concentration-time curve;
Clp = plasma clearance;
$Vd_{ss}$ = volume of distribution at steady state;
F = bioavailability.
Numbers represent average values from 3 animals per tested treatment and species.
Conjugate C8 was dissolved in 0.1% BSA in saline for IV administration in rats, and in 5% mannitol in 6 mM acetate buffer pH 5.0 for SC administration in female rats.

TABLE III

SC Pharmacokinetics in rats

| Species | Dose (μmol/kg) | $AUC_{(0-\infty)}$ (μM · hr) | $C_{max}$ (μM) | $T_{max}$ (hr) | $C_{24hr}$ (μM) |
|---|---|---|---|---|---|
| Rat (F) (n = 3) | 0.2 | 38.7 | 2.31 | 2.7 | 0.49 |
|  | 0.6 | 90.5 | 5.18 | 1.7 | 1.10 |

The results disclosed in Table I, II and III reveal that the conjugates of the present invention were surprisingly found to be highly potent (pEC50>8 in the presence of human serum) and sufficiently stable (T½>24 h in human serum) to be applied as long acting kisspeptide agonist for treatment of female infertility. Moreover, it was corroborated that the conjugates of the present invention were fully stable in the blood circulation in vivo (i.e. the kisspeptide-pentasaccharide conjugate was not prone to proteolytic degradation and it was excreted as the intact molecule). In contrast, the reference peptides P28 (kisspeptin-10) and P29 (see Table A and Table I) were not sufficiently stable (and they are still prone to fast excretion in vivo due to their small molecular size), while reference conjugate C42 (kisspeptin-10 pentasaccharide conjugate) is not sufficiently potent.

The invention claimed is:

1. A kisspeptide-pentasaccharide conjugate having the formula (I)

$$R_1—Z_1-(Asn)_n-Z_3-Asn-Z_5-Phe-Z_7—Z_8-Arg(R_3)—Z_{10}—NH_2 \quad \text{Formula (I)}$$

wherein $Z_1$ is Tyr or D-Tyr;

$Z_3$ is Trp, Hyp, Phe or Lys($R_2$);

$Z_5$ is Thr, Aib or Ala;

$Z_7$ is Gly or azaGly;

$Z_8$ is Leu; or $Z_7$ and $Z_8$ together represent

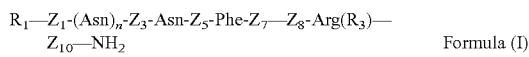

$Z_{10}$ is Phe or Trp;

n is 0 or 1;

$R_1$ or $R_2$ represents a pentasaccharide derivative having the formula (II)

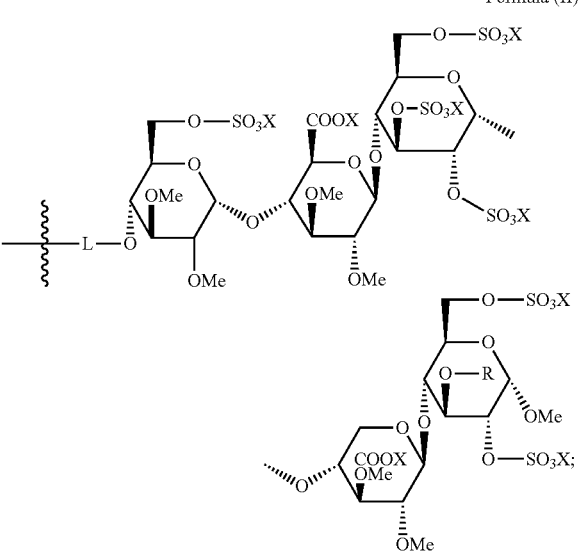

Formula (II)

wherein R is methyl or $SO_3X$;

X is a positively charged counterion;

with the proviso that when $R_2$ is present, $R_1$ is H or $(C_{1-6})$ alkylcarbonyl;

$R_3$ is H or $(C_{1-3})$alkyl; and

L represents a pharmacologically inactive linker moiety having 10-50 atoms; or a pharmaceutically acceptable salt thereof;

wherein said compound or pharmaceutically acceptable salt is further characterized by least one of the following: (a) $Z_5$ is Thr; (b) $R_3$ is methyl; (c) n is 0; $Z_1$ is D-Tyr; $Z_3$ is Hyp and $Z_{10}$ is Trp; or (d) R is methyl.

2. The kisspeptide-pentasaccharide conjugate of claim 1, wherein $Z_5$ is Thr, or a pharmaceutically acceptable salt thereof.

3. The kisspeptide-pentasaccharide conjugate of claim 1, wherein $R_3$ is methyl, or a pharmaceutically acceptable salt thereof.

4. The kisspeptide-pentasaccharide conjugate of claim 1, wherein n is 0; $Z_1$ is D-Tyr; $Z_3$ is Hyp and $Z_{10}$ is Trp, or a pharmaceutically acceptable salt thereof.

5. The kisspeptide-pentasaccharide conjugate of claim 2, wherein n is 1 and $Z_{10}$ is Phe, or a pharmaceutically acceptable salt thereof.

6. The kisspeptide-pentasaccharide conjugate of claim 1, wherein R is methyl, or a pharmaceutically acceptable salt thereof.

7. The kisspeptide-pentasaccharide conjugate of claim 1 which is selected from

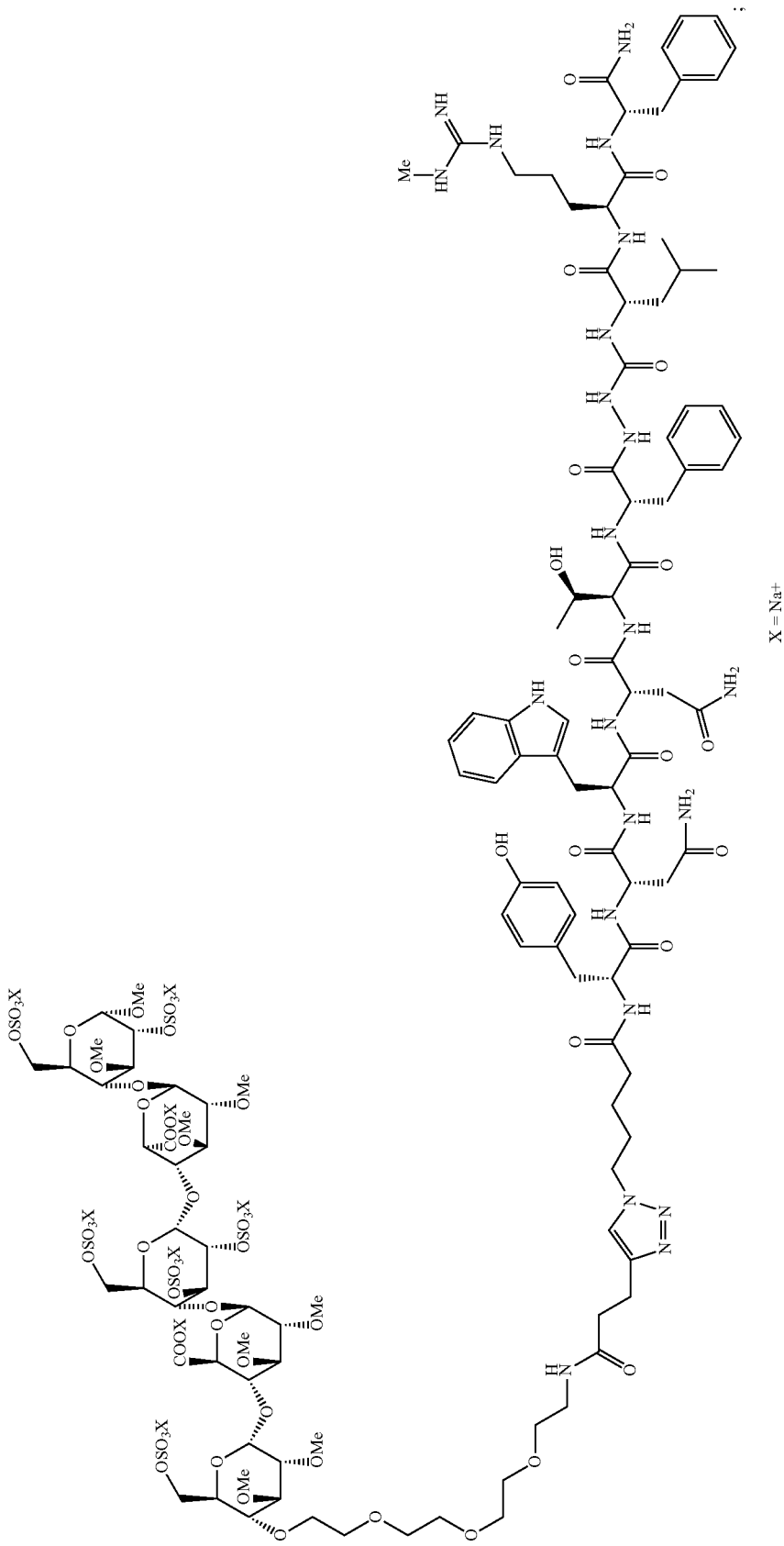

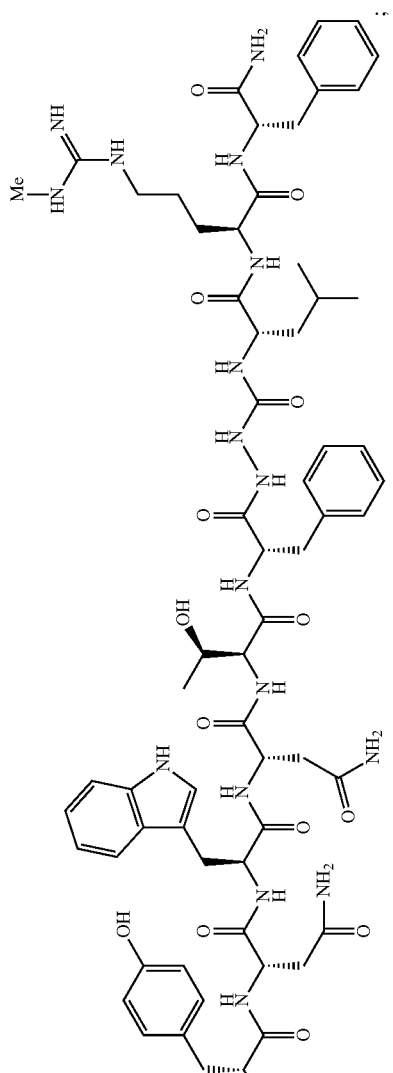
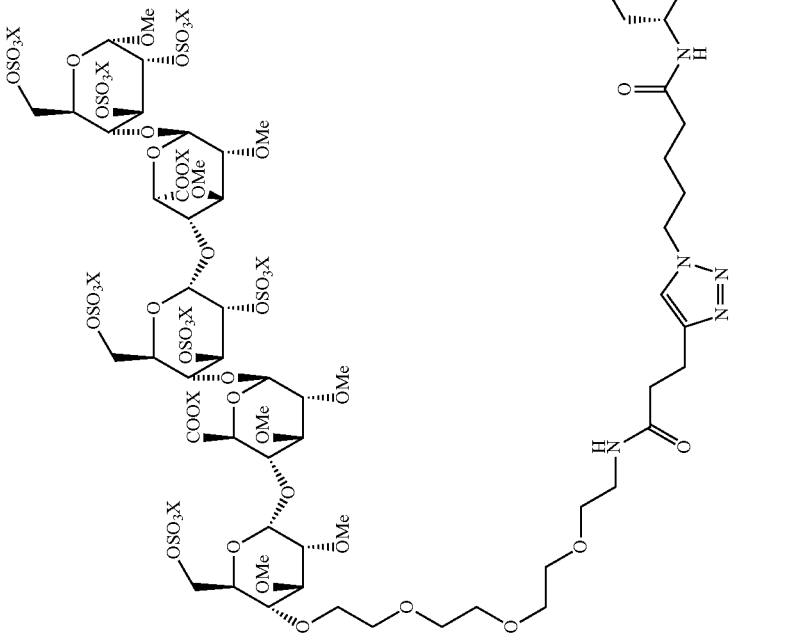

-continued
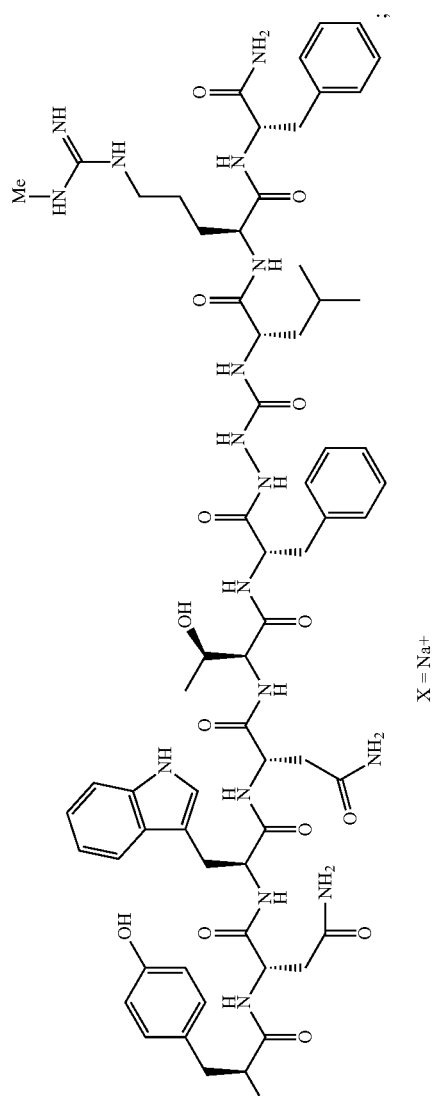
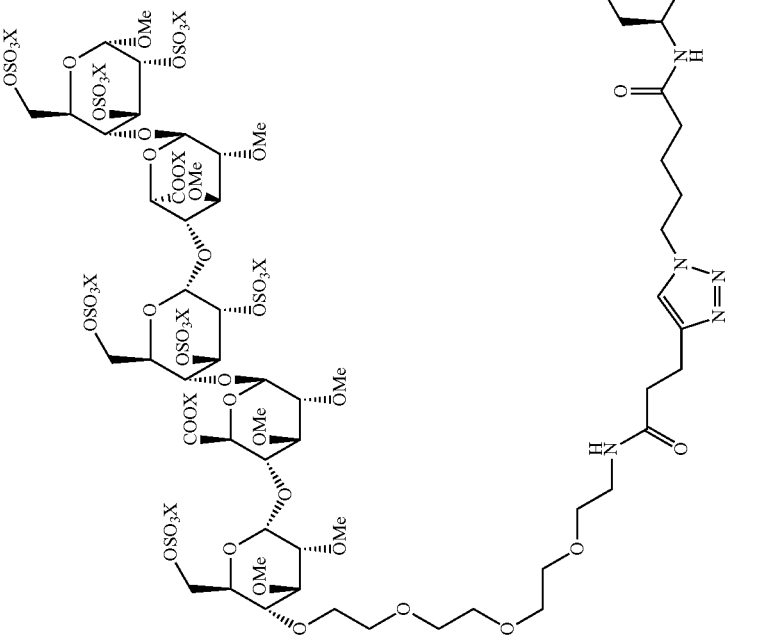
X = Na+

-continued
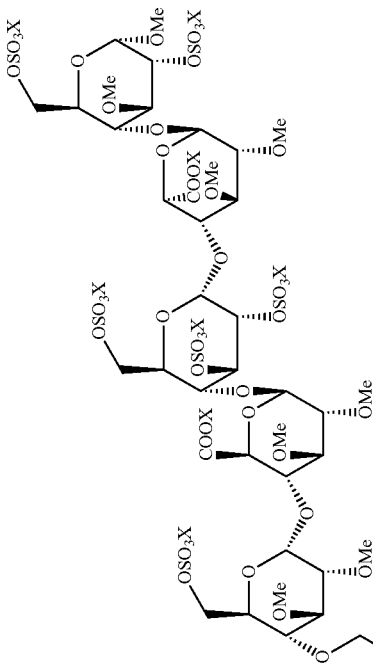
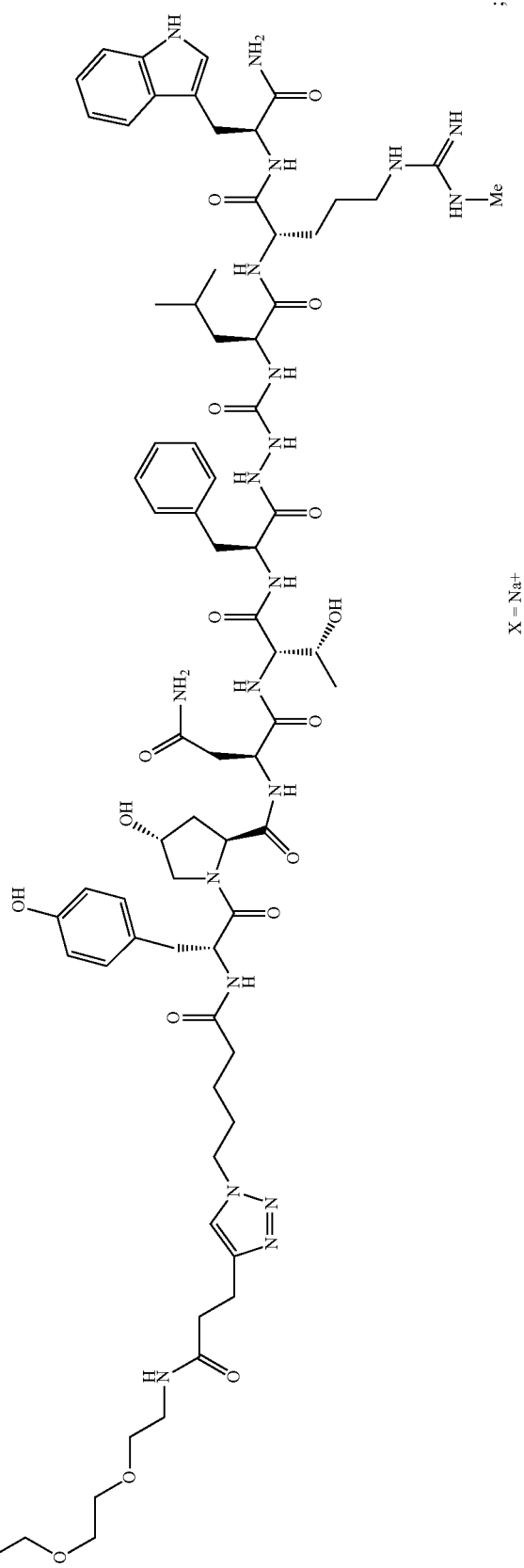

-continued
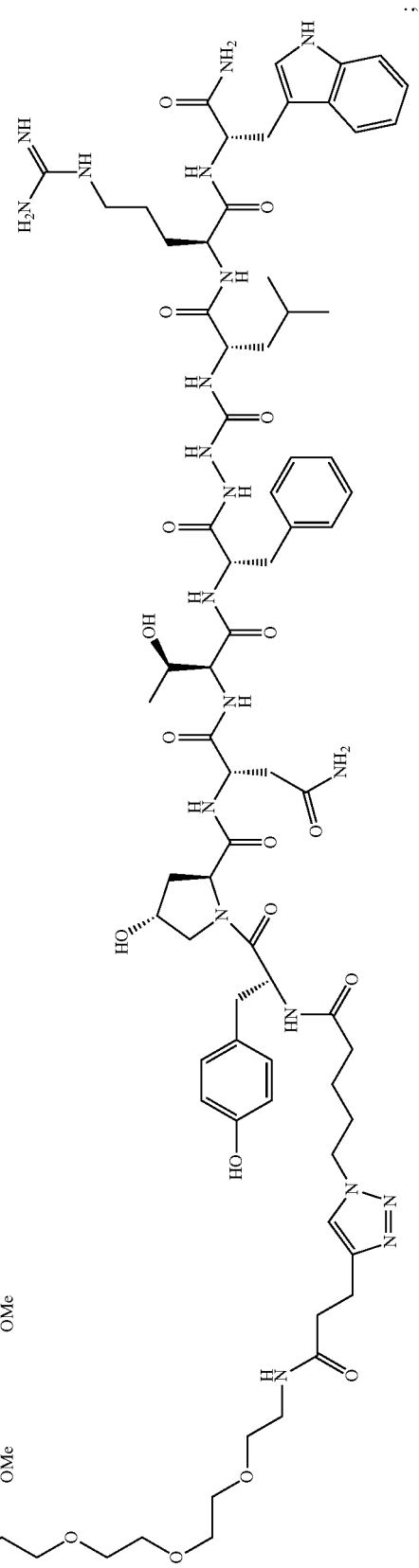

-continued
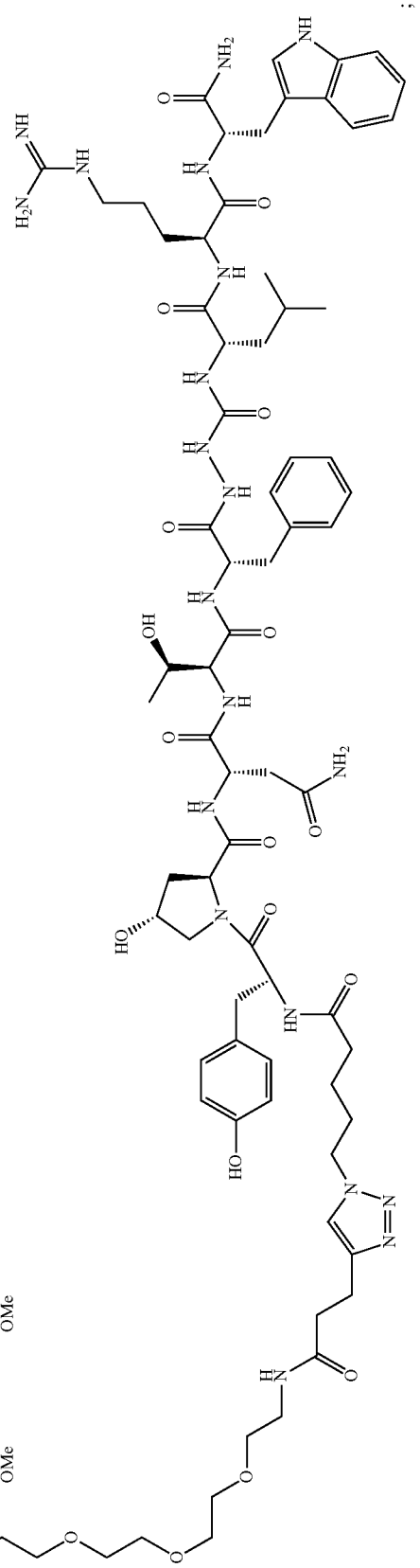
X = Na+

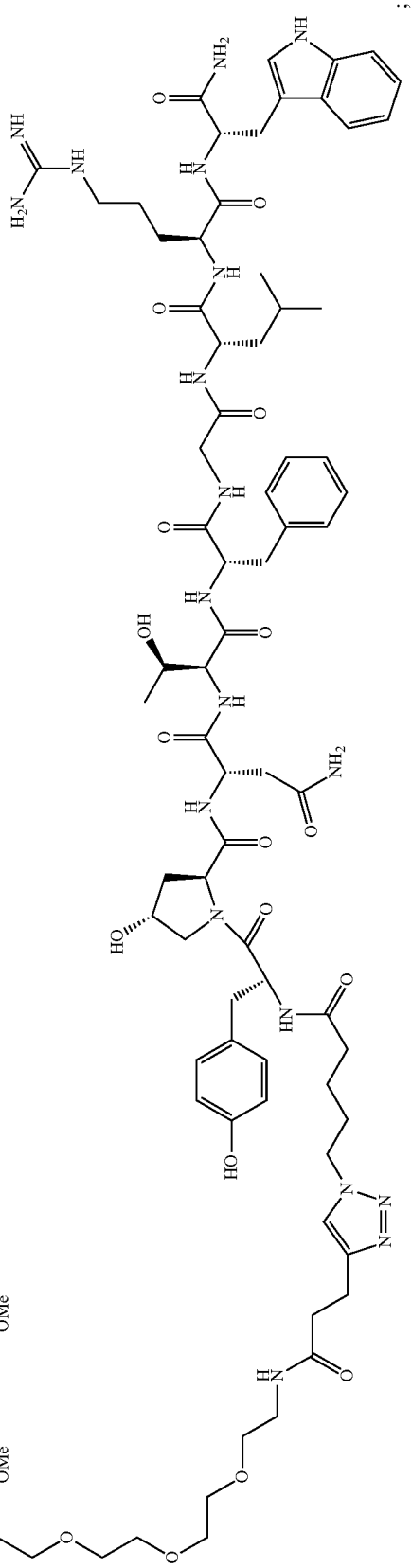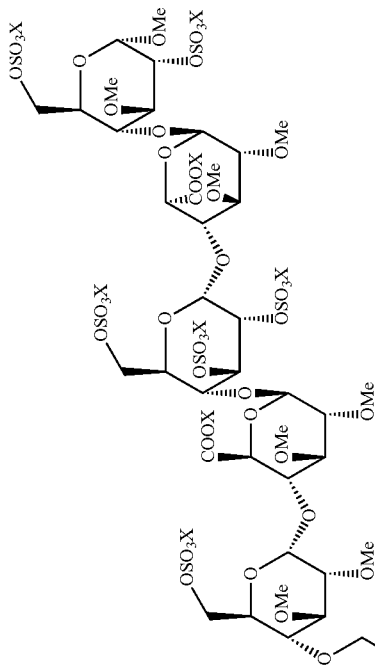

-continued
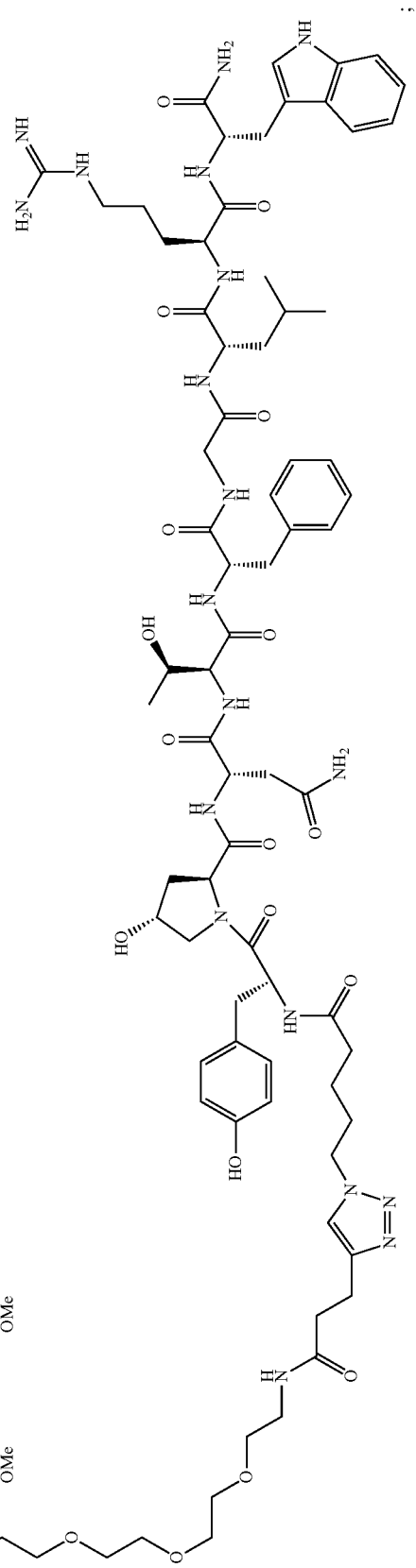
X = Na+

-continued
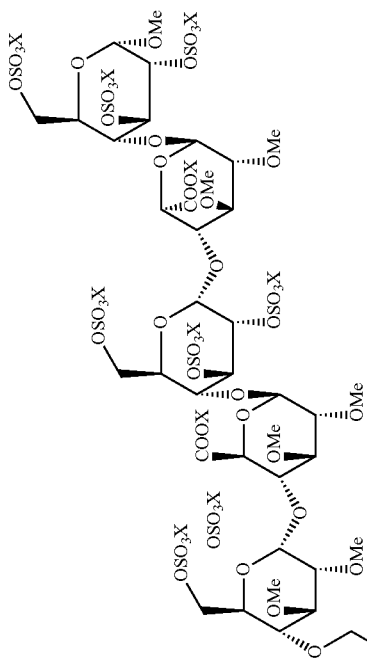
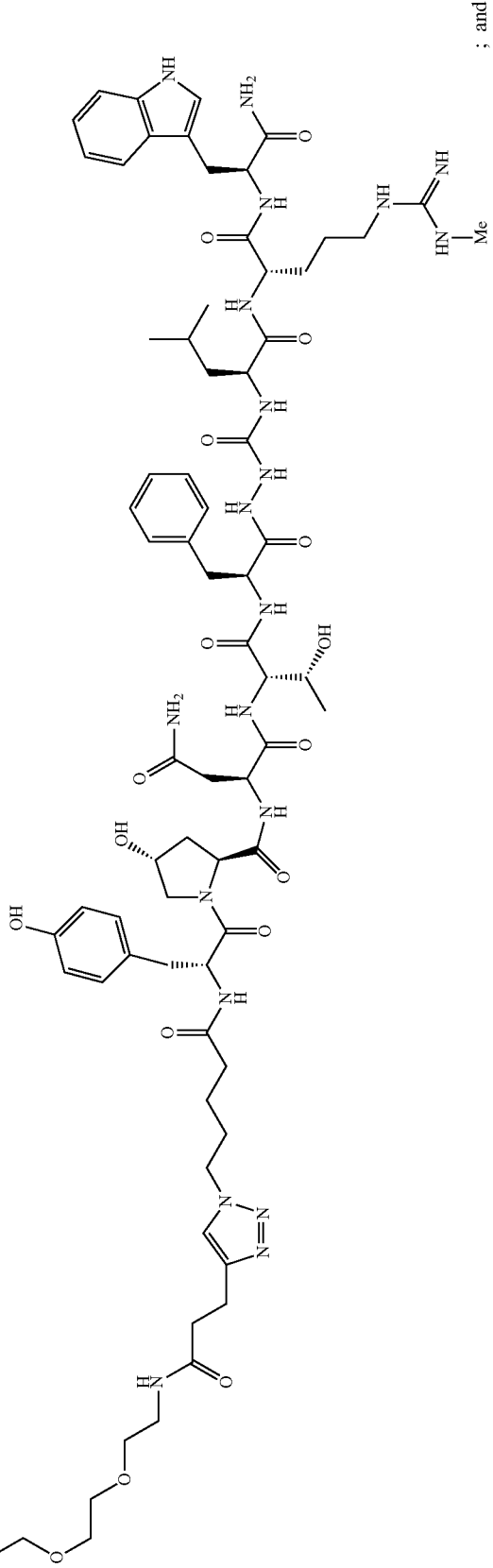
X = Na+
; and

-continued
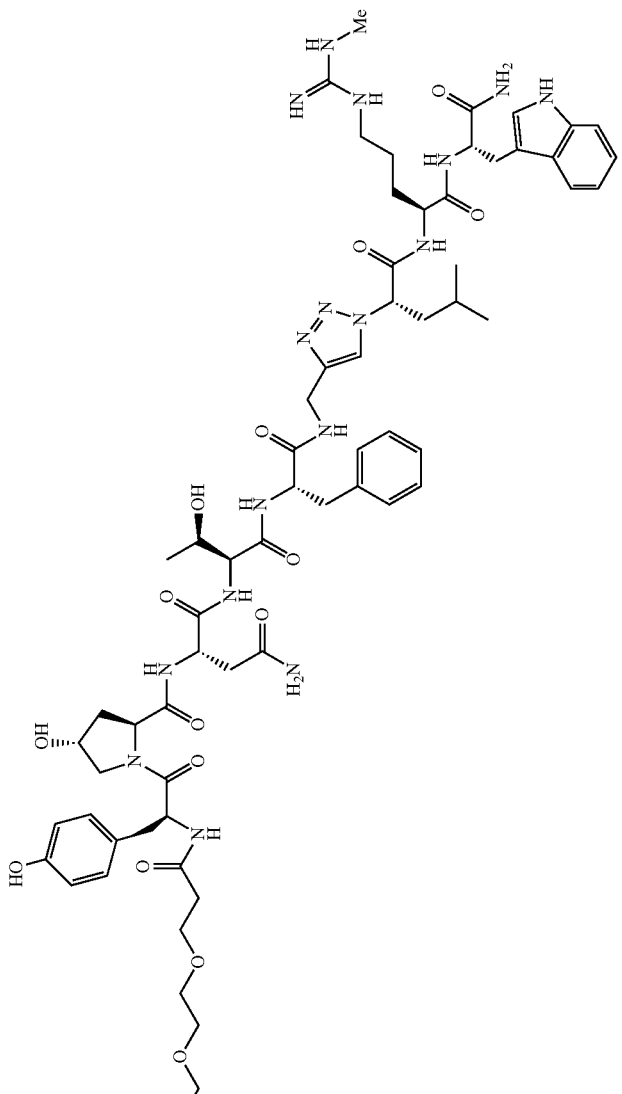
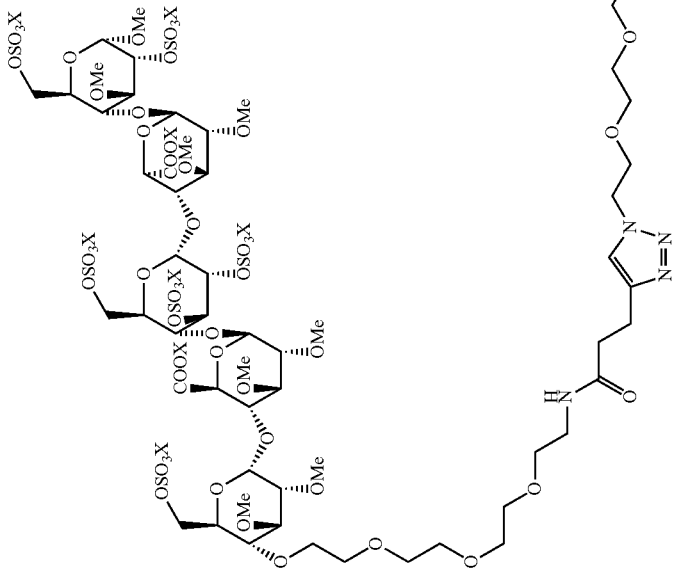
X = Na+ or a pharmaceutically acceptable salt thereof.

8. A method of treating female infertility which comprises administering a kisspeptide-pentasaccharide conjugate of claim 1, or a pharmaceutically acceptable salt thereof.

9. A pharmaceutical composition comprising a kisspeptide-pentasaccharide conjugate of claim 1 or a pharmaceutically acceptable salt thereof, in admixture with pharmaceutically acceptable auxiliaries.

10. The kisspeptide-pentasaccharide conjugate of claim 3, wherein n is 1 and $Z_{10}$ is Phe, or a pharmaceutically acceptable salt thereof.

* * * * *